: US 6,562,055 B2
(45) Date of Patent: May 13, 2003

(12) United States Patent
Walen

(54) CUTTING ATTACHMENT FOR A SURGICAL HANDPIECE DESIGNED TO BE SELECTIVELY COUPLED TO THE HANDPIECE

(75) Inventor: James G. Walen, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/788,278

(22) Filed: Feb. 17, 2001

(65) Prior Publication Data

US 2002/0058958 A1 May 16, 2002

Related U.S. Application Data

(60) Provisional application No. 60/183,766, filed on Feb. 18, 2000.

(51) Int. Cl.$^7$ ................................................ A61B 17/14
(52) U.S. Cl. ...................................... 606/180; 606/167
(58) Field of Search ................................. 606/180, 167, 606/170, 166; 30/337–339, 340, 348, 162

(56) References Cited

U.S. PATENT DOCUMENTS

| 1,862,337 | A | | 6/1932 | Emrick |
| 3,489,422 | A | | 1/1970 | Selowitz |
| 4,279,598 | A | | 7/1981 | Scheicher |
| 5,061,238 | A | | 10/1991 | Shuler |
| 5,634,933 | A | * | 6/1997 | McCombs et al. ......... 408/226 |
| 5,782,836 | A | | 7/1998 | Umber et al. |
| 5,888,200 | A | | 3/1999 | Walen |
| 5,924,864 | A | | 7/1999 | Logé et al. |
| 5,928,241 | A | | 7/1999 | Menut et al. |

FOREIGN PATENT DOCUMENTS

| DE | 21 20 320 A | 11/1972 |
| DE | 26 30 400 A | 1/1978 |
| DE | 297 20 616 | 10/1998 |
| EP | 0 928 599 | 7/1999 |
| WO | 96/10962 | 4/1996 |
| WO | WO 96 10962 A | 4/1996 |

OTHER PUBLICATIONS

PCT App. No. PCT/US01/05378 Initial Preliminary Examination Report, May 2002.
PCT App. No. PCT/US01/05378 Final Preliminary Examination Report, Jun. 2002.

* cited by examiner

Primary Examiner—John J. Calvert
Assistant Examiner—Katherine Moran
(74) Attorney, Agent, or Firm—Flynn, Thiel, Boutell & Tanis, P.C.

(57) ABSTRACT

A cutting accessory (40a) for use with a powered surgical tool. The cutting accessory includes a head (42) with a cutting surface that is applied to a surgical site and a shaft (44a) that extends from the head. A plurality of retention features (530) are formed on the shaft. This makes it possible to longitudinally adjust the position of the cutting accessory relative to the tool with which the accessory is used. The interstitial sections of the shaft located between the retention features have an-asymmetric profile relative to the longitudinal axis of the shaft. This facilitates the auto-alignment of the cutting accessory to a handpiece when clamping members integral to the handpiece are pressed against the accessory.

31 Claims, 35 Drawing Sheets

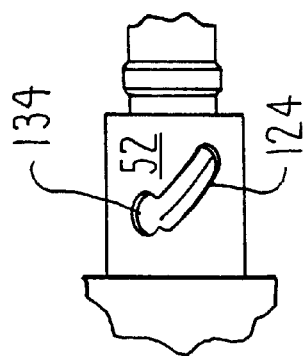
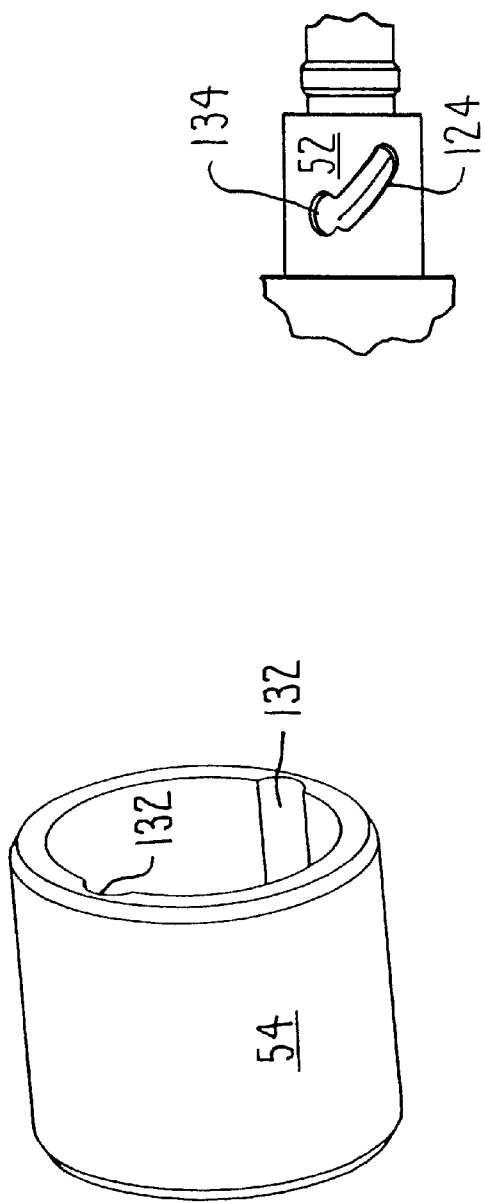
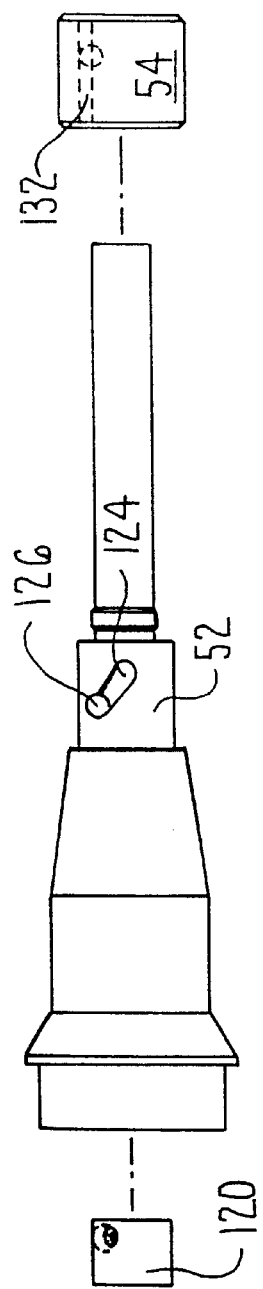
FIG. 8A
FIG. 8
FIG. 8B

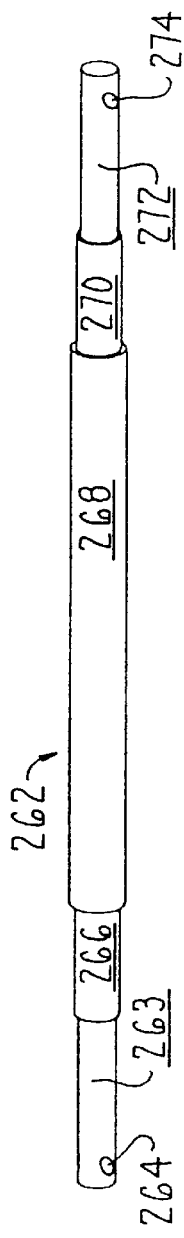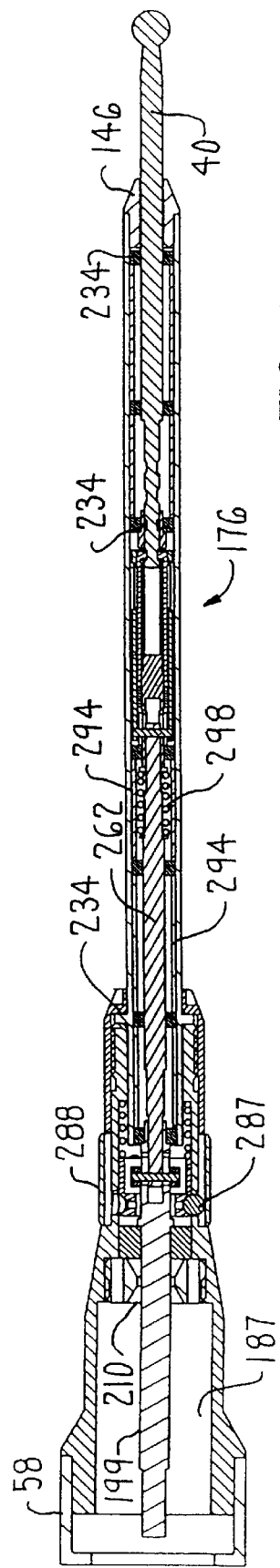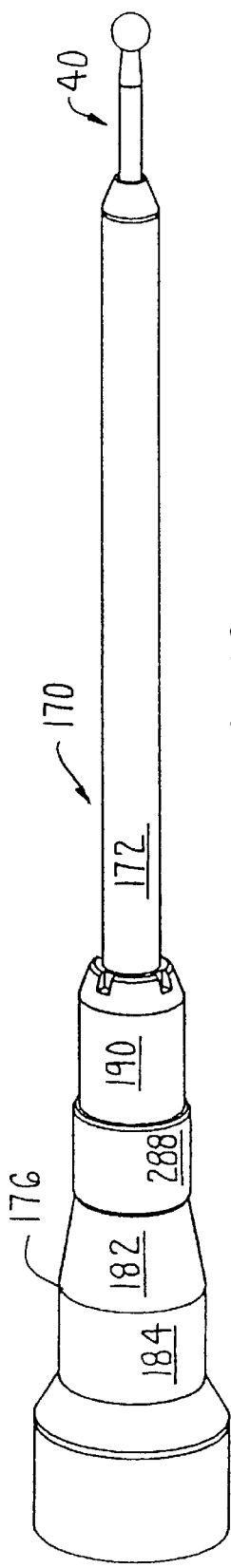

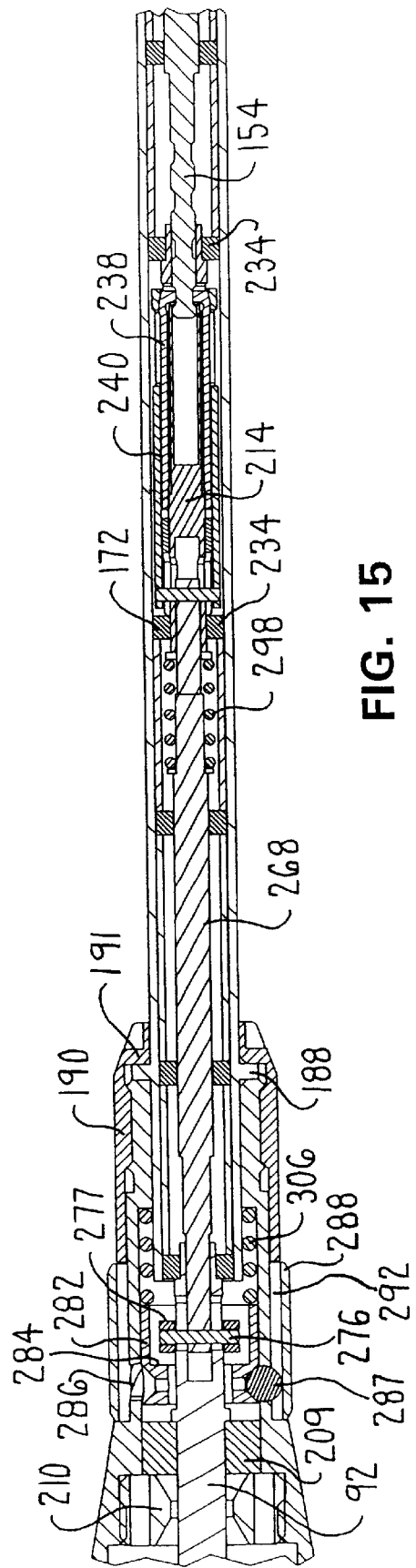

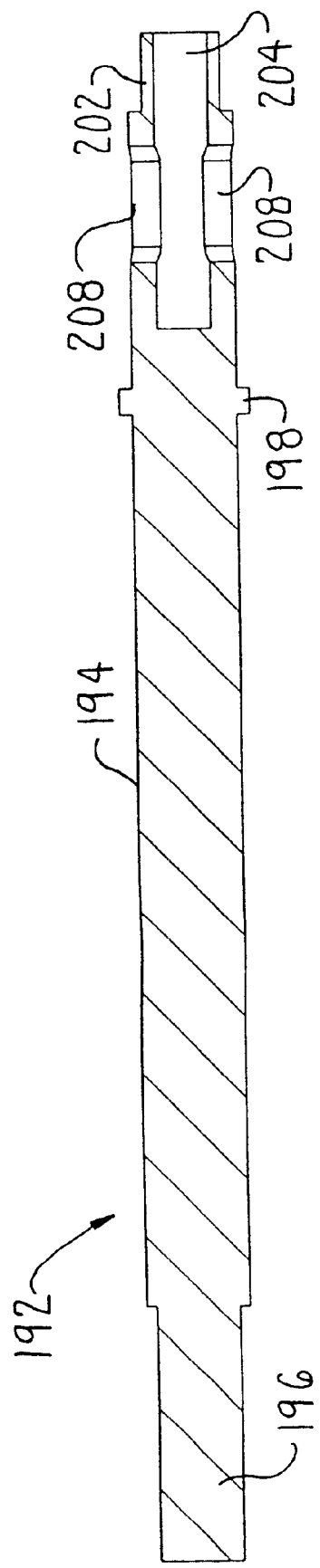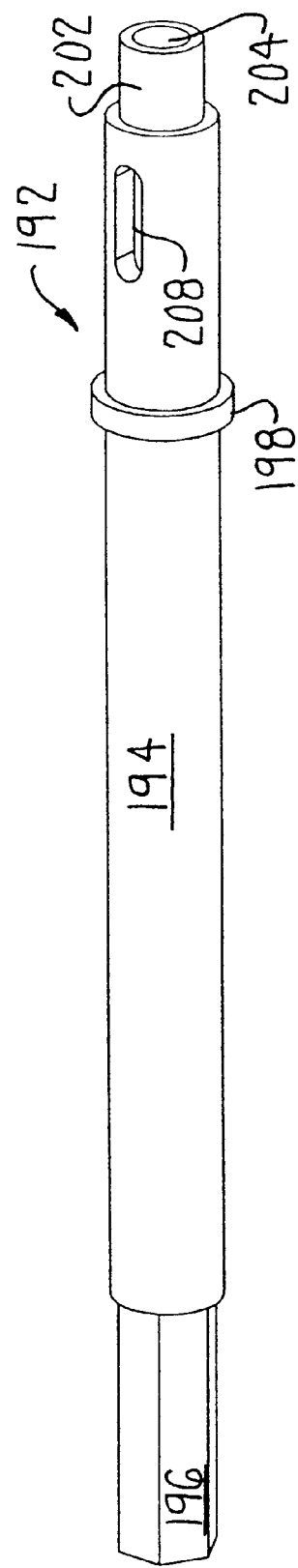
FIG. 16B
FIG. 16A

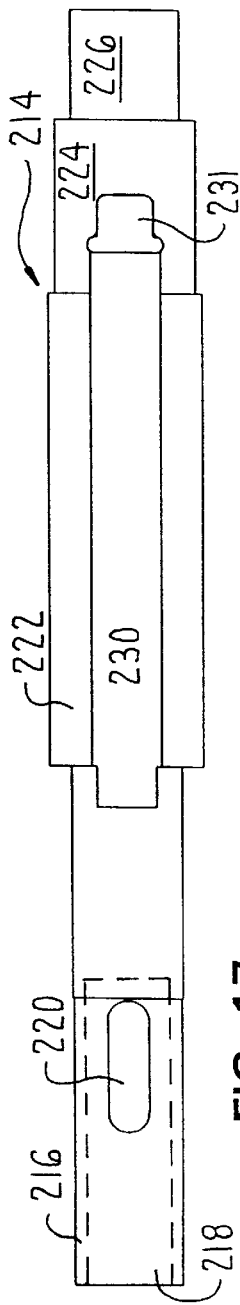
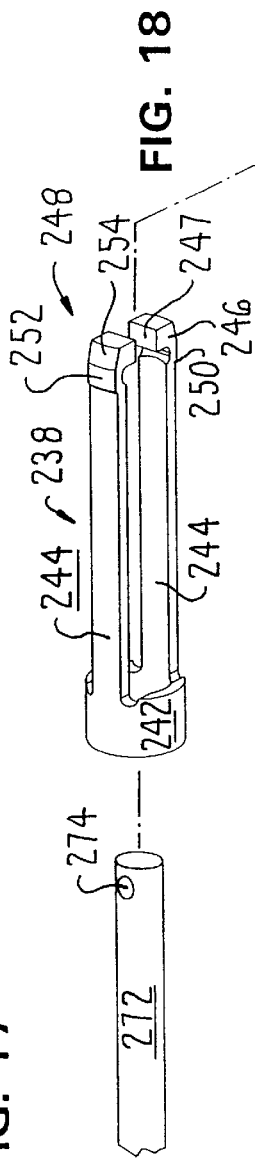
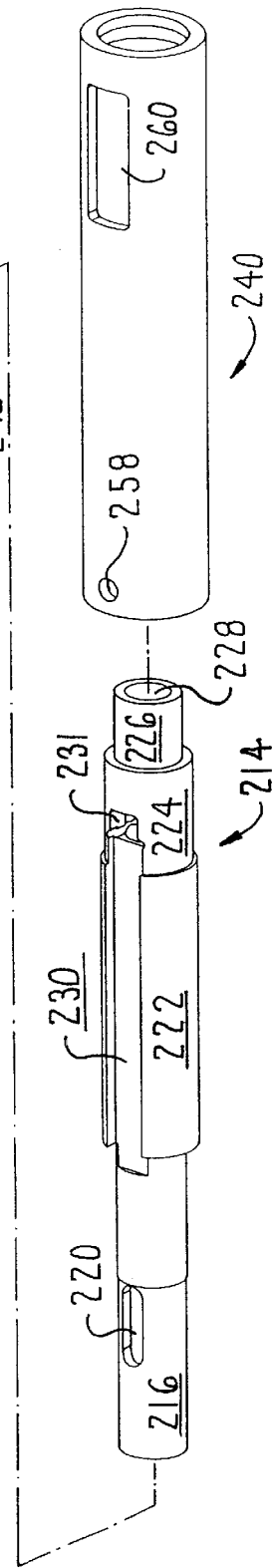
FIG. 17
FIG. 18
FIG. 19

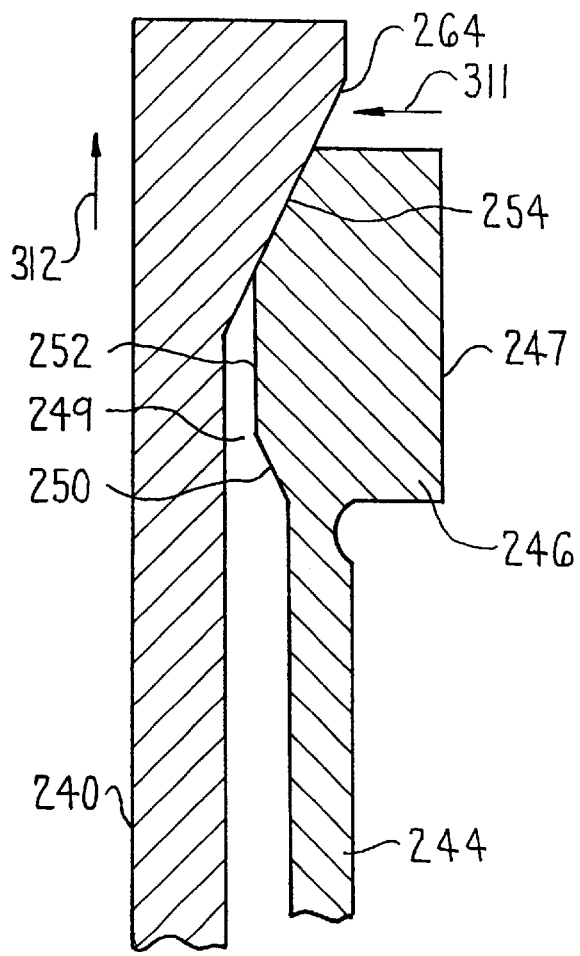
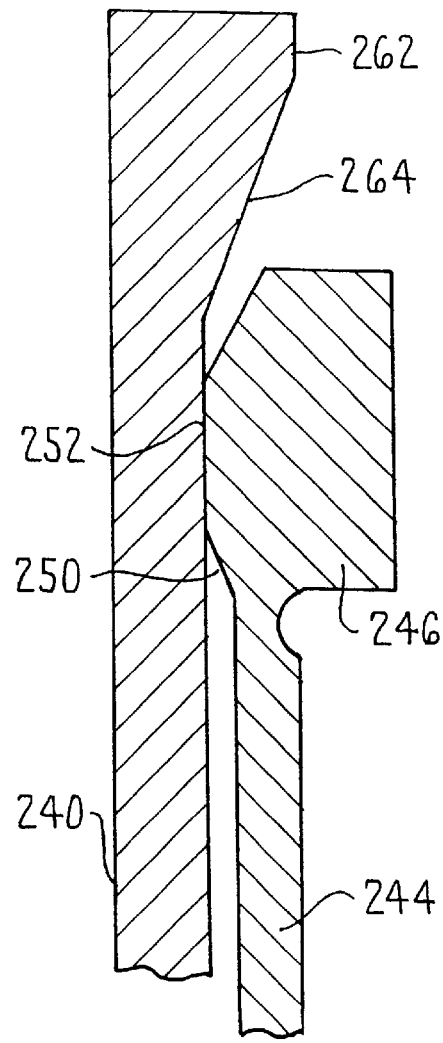
FIG. 21A     FIG. 21B

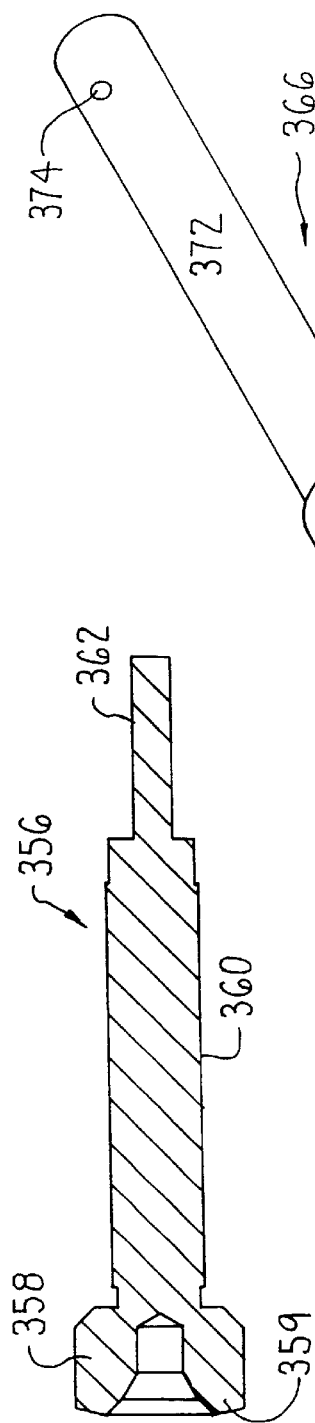

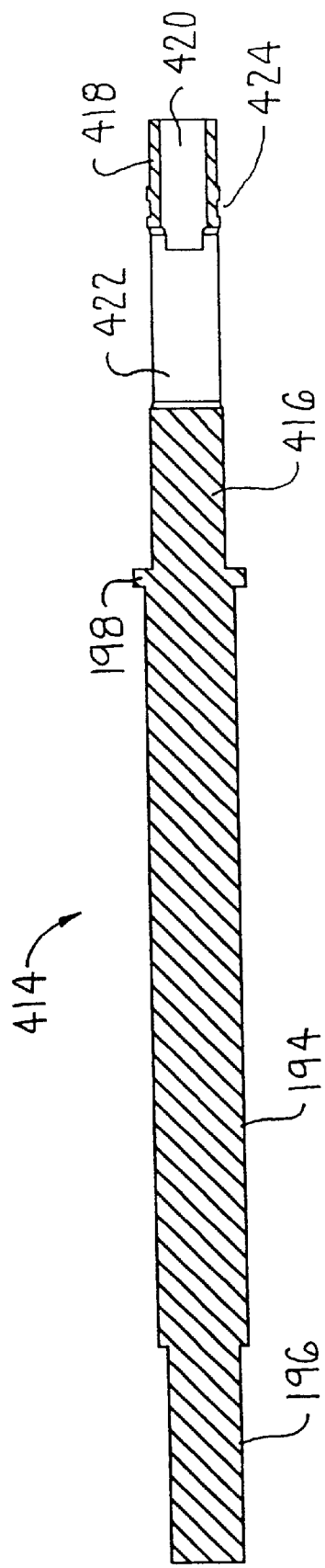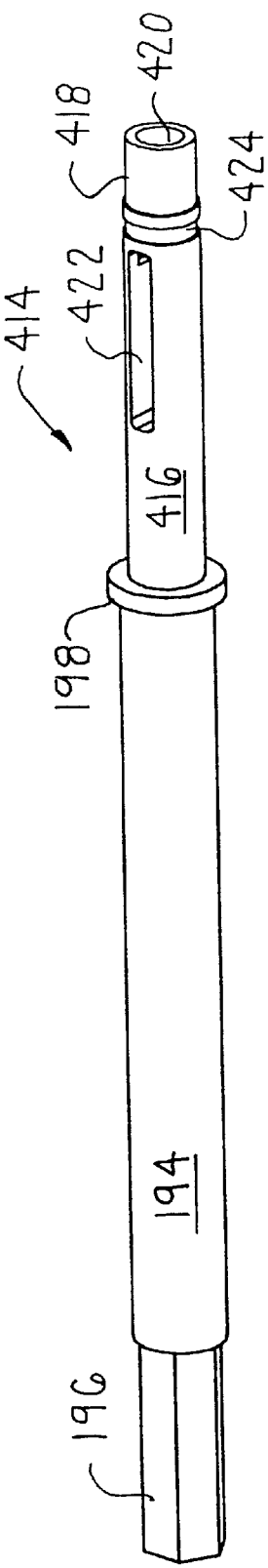
FIG. 30B
FIG. 30A

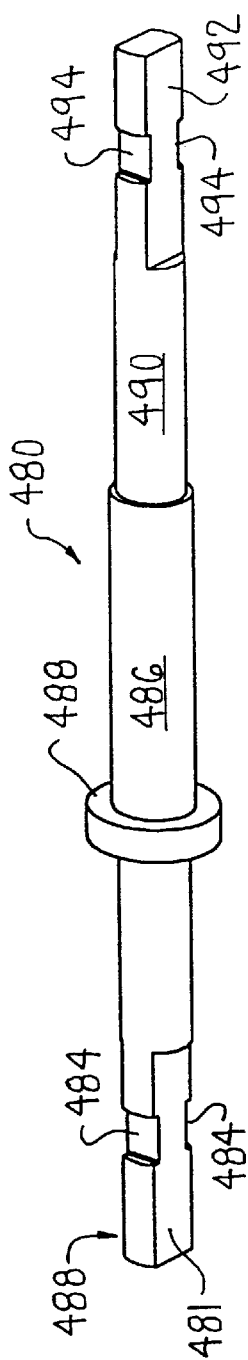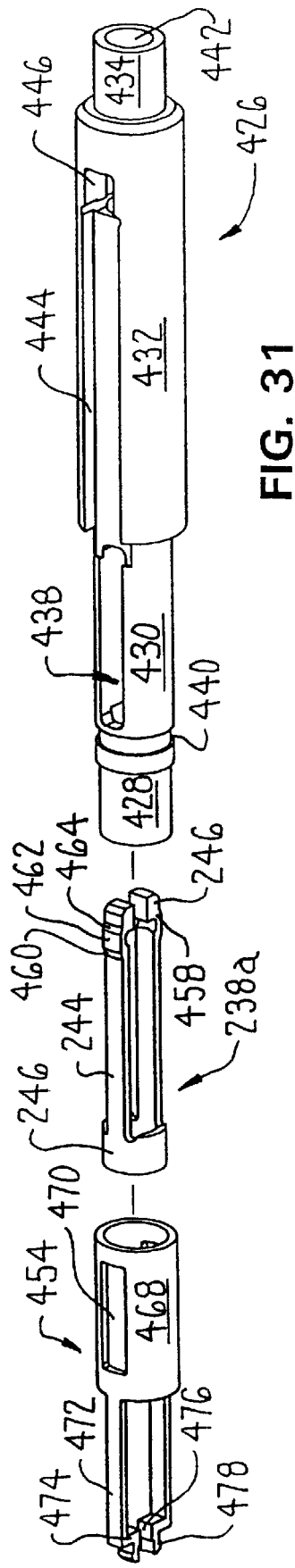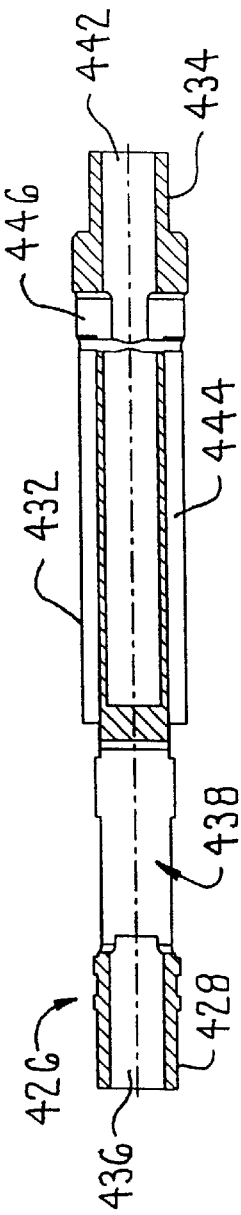

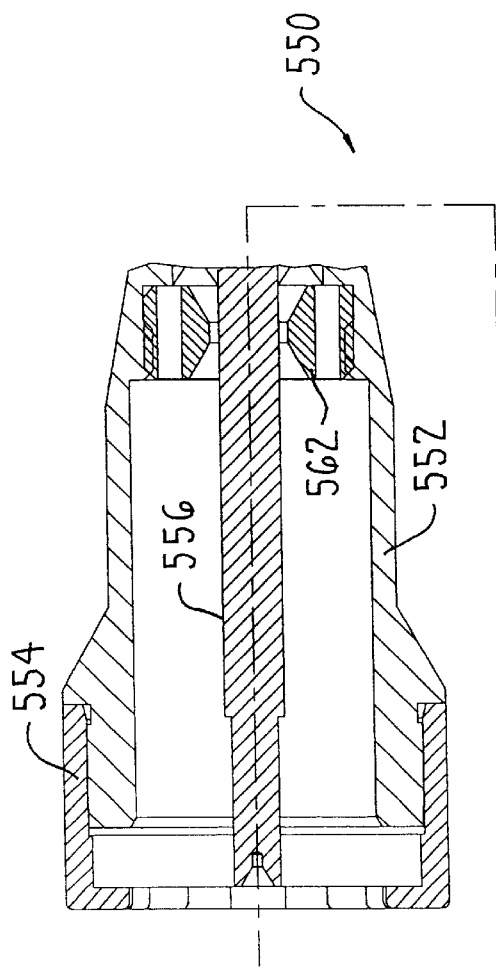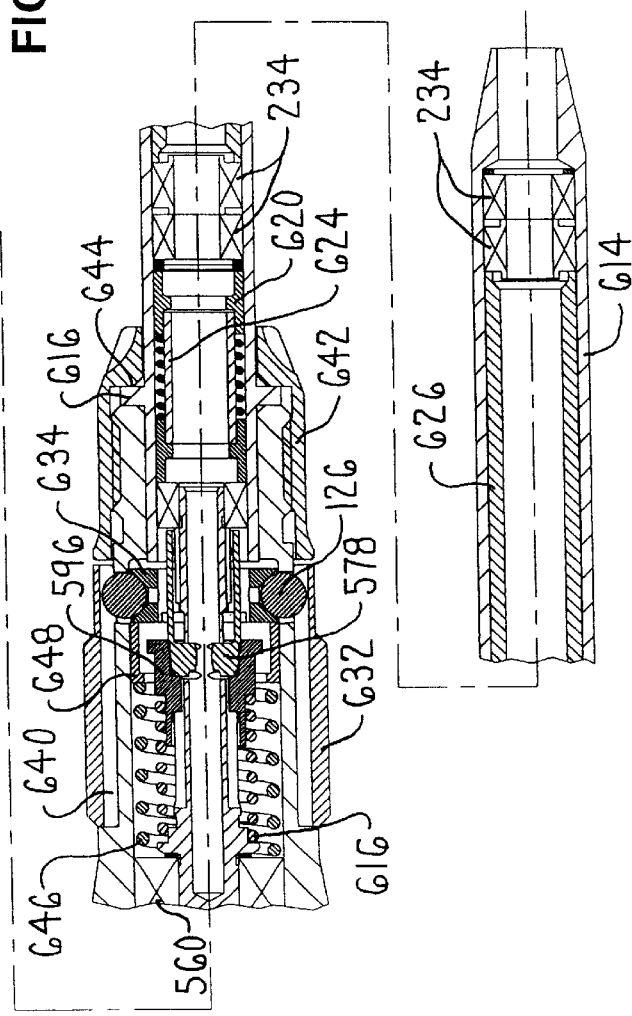
FIG. 43

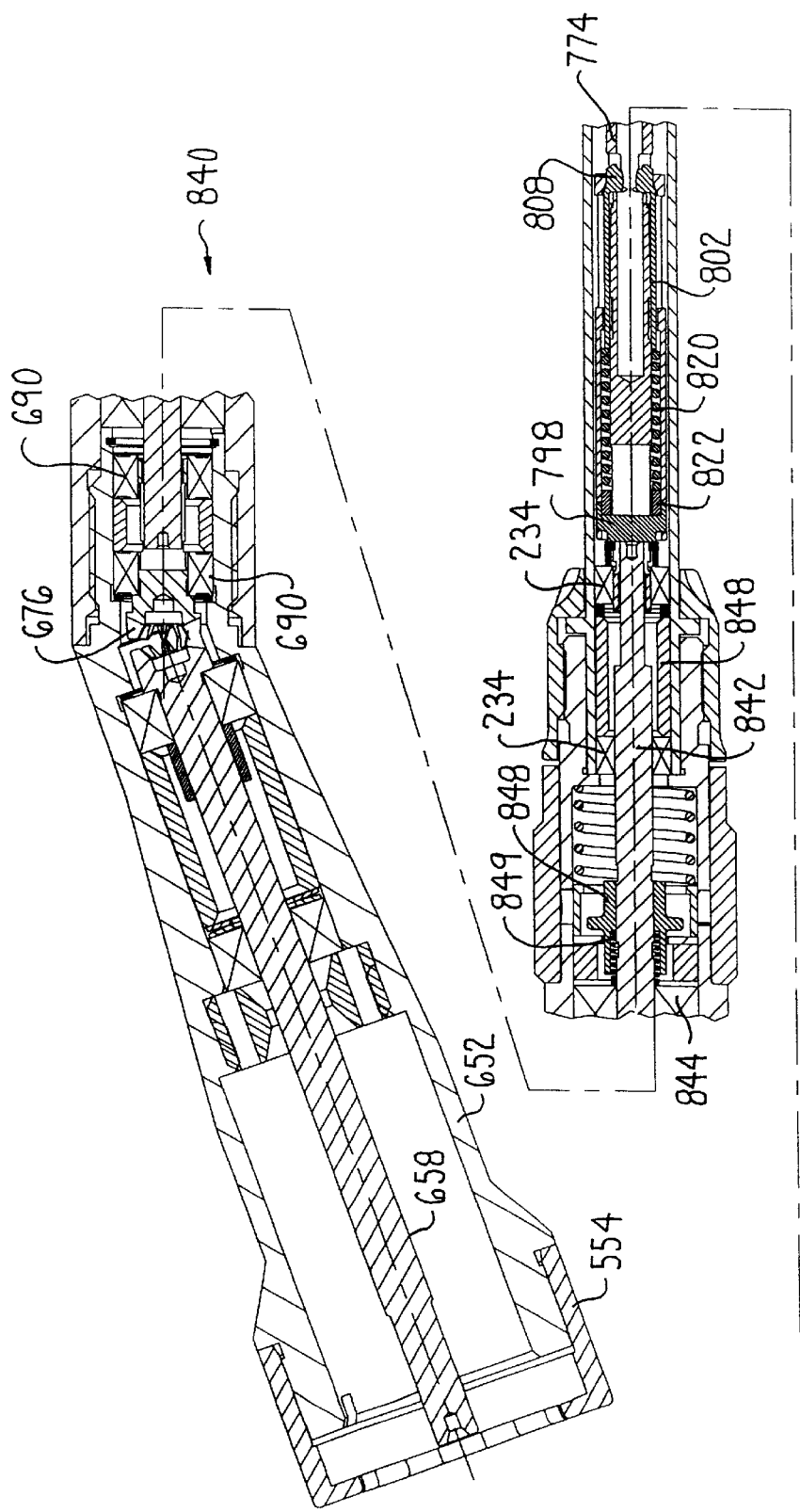
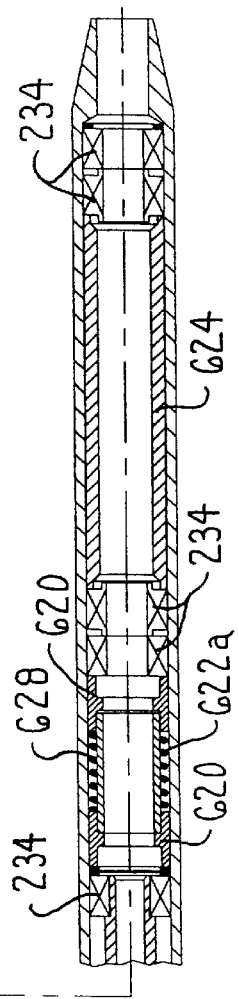
FIG. 62

CUTTING ATTACHMENT FOR A SURGICAL HANDPIECE DESIGNED TO BE SELECTIVELY COUPLED TO THE HANDPIECE

RELATIONSHIP TO EARLIER FILED APPLICATION

This application claims priority under 35 U.S.C. Sec. 119 from United States Provisional Application No. 60/183 766, filed Feb. 18, 2000. This application is a continuation-in-part of the '766 Application.

FIELD OF THE INVENTION

This invention relates generally to a surgical tool system to which cutting accessories are selectively attached. More particularly, this invention relates to a surgical tool system and a complementary cutting accessory that are collectively configured to allow the longitudinal position of the cutting accessory relative the handpiece to be selectively set.

BACKGROUND OF THE INVENTION

In modern surgery one of the most important instruments available to medical personnel is the powered surgical tool. Typically, this tool comprises some type of handpiece in which a motor is housed. Secured to the handpiece is a cutting accessory designed for application to a surgical site on a patient in order to accomplish a specific medical task. Some powered surgical tools are provided with drills or burrs for cutting bores into hard tissue or for selectively removing the hard tissue. Still other powered surgical tools are provided with saw blades as cutting accessories. These tools are used for separating large sections of hard and/or soft tissue. The ability to use powered surgical tools on a patient has lessened the physical strain of physicians and other medical personnel when performing procedures on a patient. Moreover, most surgical procedures can be performed more quickly, and more accurately, with powered surgical tools than with the manual equivalents that preceded them.

The Applicant's U.S. Pat. No. 5,888,200, entitled, MULTI-PURPOSE SURGICAL TOOL SYSTEM, issued Mar. 30, 1999, incorporated herein by reference, discloses a surgical tool system designed for a number of different applications. This tool system includes a handpiece in which a motor is housed. The handpiece also includes a first coupling assembly for selectively coupling the shaft of a cutting accessory to the motor shaft. This handpiece also includes a second coupling assembly. The second coupling assembly is used to selectively secure an attachment to the front end of the handpiece. This attachment may include its own drive shaft and accessory coupling assembly. These attachments are elongated attachments, angled attachments and/or able to actuate saw blades. Thus, an advantage of providing this type of tool system is that a single handpiece can be used to drive a large number of different cutting accessories and facilitate the positioning of the accessories at the surgical site in a manner that is either required or desired for a particular surgical procedure.

Popular cutting accessories that are used with this type of surgical tool system include drills and burs. Each of these cutting accessories typically has a head that forms the actual tissue removal member of the accessory. A shaft extends rearwardly from the head. The shaft is the component of the cutting accessory against which the coupling assembly locks.

There is a limitation associated with the above-described system. The coupling assembly of this system is designed so that a cutting accessory can only be secured to it in a single, fixed location relative to the handpiece. A disadvantage of this arrangement is that surgeons frequently find it useful to have some degree of flexibility in positioning the head of the cutting accessory relative to the handpiece. To date, to offer this flexibility, it is necessary to provide a set of cutting accessories that have identical cutting heads. The difference between the accessories is the length of their complementary shafts. When a surgeon wants the head of the accessory to be positioned relatively close to the handpiece, he/she installs in the handpiece a cutting accessory with a shaft that is relatively short in length. If the surgeon wants the head of the accessory to be spaced a distance from the handpiece, he/she installs in the handpiece a cutting accessory that has a relatively long shaft.

Moreover, during a surgical procedure, a surgeon may want to use different tools to access different locations at the surgical site. Alternatively, surgeons have individual preferences regarding how they want to view a surgical site and/or handle their surgical tools. In order to accommodate these variations, surgical tool systems are provided with members that vary in only the geometry and/or dimensions of the components employed to transfer the power developed by the handpiece motor to the associated cutting accessory. For example, the tool system described in the above-referenced U.S. Pat. No. 5,888,200 has different length attachments and attachments that have distal end sections that are straight and angled from the associated handpiece housing. If surgeon has to access a surgical site located close to the skin of the patient he/she has available a medium length attachment. Alternatively, if the surgeon has to access a surgical site deep within the patient, the surgeon has available a long attachment. This attachment, in comparison to the medium length attachment, holds the head of the cutting accessory a relatively long distance away from handpiece. Angled attachments are also available. These attachments are used to hold the cutting accessory at an angle that is offset to the longitudinal axis of the handpiece. Angled attachments are used to position the cutting accessory at surgical sites that are difficult to reach and/or to provide a surgeon with an alternative field of view of the surgical site.

Clearly, having these different attachments available is beneficial to the surgeon. However, the coupling assemblies internal to these attachments are often located different longitudinal distances from their head ends, theirs distal ends, the ends from which the shaft of the accessory emerges. In order to use these attachments, it is necessary to provide cutting accessories with the same head but that have different length shafts. Accessories with short length shafts are fitted into attachments in which the coupling assemblies are positioned relatively short distances from their distal end openings. Accessories with long length shafts are fitted into attachments in which the coupling assemblies are positioned longer distances from their distal end openings. This is another reason why it is sometimes necessary to have a number of different cutting accessories available for use in a single surgical procedure that vary only in their shaft length.

Another limitation associated with cutting accessories such as drills and burs is related to the fact that sometimes a number of different accessories are packaged as a set. These accessories are so packaged together because a surgeon, during a procedure, may want to view the complete set of accessories he/she has available for use. Alternatively, prior to the beginning of a surgical procedure, a number of individual accessories are each unpackaged and arranged as a set for the surgeon. Again, this is to allow the surgeon to both view and have easy access to a number of different accessories.

However, often, during a procedure, the surgeon does not use all of the cutting accessories that have been unwrapped from their sterile packaging. The accessories that are used are typically discarded. This is because the cutting heads of these accessories are at least partially worn. However, after the procedure, there may be one or more exposed cutting accessories that were not used. These accessories can be used in a new procedure, if prior to reuse they are sterilized to remove any contaminates they may have picked up as a result of their exposure to the environment. In a procedure used to sterilize these accessories they are heated to a temperature of approximately 132° C., and subjected to saturated water vapor at a pressure of 2.1 bars. These accessories are formed of tool steel because cutting surfaces formed from this material tends to wear at a slower rate cutting surfaces formed from stainless steel. Also, tool steel is less expensive than an alternative material, carbide steel. However, during the above-described sterilization process, the tool steel tends to discolor. This discoloration is disconcerting to medical personnel. Consequently, medical personnel are reluctant to use these unused autoclave-sterilized accessories even though their quality and the degree of sterilization is the same as accessories that have just been removed from the manufacturer's packaging. Thus, there is tendency to discard these unused accessories even though, with proper sterilization, that can be available for use in a later procedure. The discarding of these cutting accessories, even though they have not even been used, is a waste of resources.

SUMMARY OF THE INVENTION

This invention relates to a new and useful surgical tool system. The surgical tool system of this invention includes a handpiece with a coupling assembly and complementary cutting accessories that are designed to fit the handpiece. Collectively, the coupling assembly and the cutting accessories are designed so that the longitudinal extent to which the cutting accessories extend out of the coupling assembly can be selectively set. Still a further feature of the surgical tool system of this invention is that though system has different length attachments, the coupling assemblies internal to these attachments are collectively designed so that a cutting accessory having a single length shaft, a common length shaft, can be used with each attachment.

Another feature of the surgical tool system of this invention is that the cutting accessories are fabricated so that, as long as the accessories are not used in a surgical procedure, the accessories can be exposed to autoclave sterilization without corroding.

BRIEF DESCRIPTION OF THE DRAWINGS

The invention is pointed out with particularity in the claims. The above and further features of this invention may be better understood by reference to the following description taken in conjunction with the accompanying drawings, in which:

FIG. 8 is an exploded view of the outer component of the coupling assembly;

FIG. 8A is a plan view depicting the shape of one of the slots formed in the attachment housing;

FIG. 8B is a perspective view of a collar;

FIG. 13 is a perspective view of an alternative attachment of the system of this invention;

FIG. 14 is a cross-sectional view of the attachment of FIG. 13;

FIG. 15 is an enlarged cross-sectional view of the attachment of FIG. 13 in which the components forming the coupling assembly internal to the attachment are depicted;

FIGS. 16A and 16B are, respectively, perspective and cross-section views of the input drive shaft of the attachment of FIG. 13;

FIG. 17 is a plan view of the output drive shaft of the attachment of FIG. 13;

FIG. 18 is an exploded view of how the forward components of the coupling assembly of the drive shaft of FIG. 12 cooperate;

FIG. 19 is a cross-sectional view of the collet sleeve of the coupling assembly of FIG. 13;

FIG. 20 is a plan view of the push rod of the coupling assembly of FIG. 12;

FIGS. 21A and 21B are cross-sectional views depicting how, as a result of an initial radial displacement of the collet legs and feet of the coupling assembly of FIG. 12, the collet sleeve blocks further displacement of the collet legs and feet;

FIG. 24 is a cross-sectional view of the intermediate drive shaft of the attachment of FIG. 22;

FIG. 25 is a perspective view of the push rod of the attachment of FIG. 22;

FIG. 26 is a perspective view of the alignment sleeve of the attachment of FIG. 22;

FIGS. 30A and 30B are, respectively, perspective and cross-sectional views of the input drive shaft of the attachment of FIG. 27;

FIG. 31 is an exploded view depicting the arrangement of the output drive shaft of the attachment of FIG. 27, and the collet and collet sleeve that are fitted around the drive shaft;

FIG. 31A is a cross sectional view of the output drive shaft of the attachment of FIG. 27;

FIG. 32 is a perspective view of the push rod of the attachment of FIG. 27;

FIG. 43 is a multi-section cross sectional view of an alternative attachment of this invention.

FIG. 62 is a multi-section cross sectional view of an alternative long attachment of this invention.

DETAILED DESCRIPTION

Figure 1:
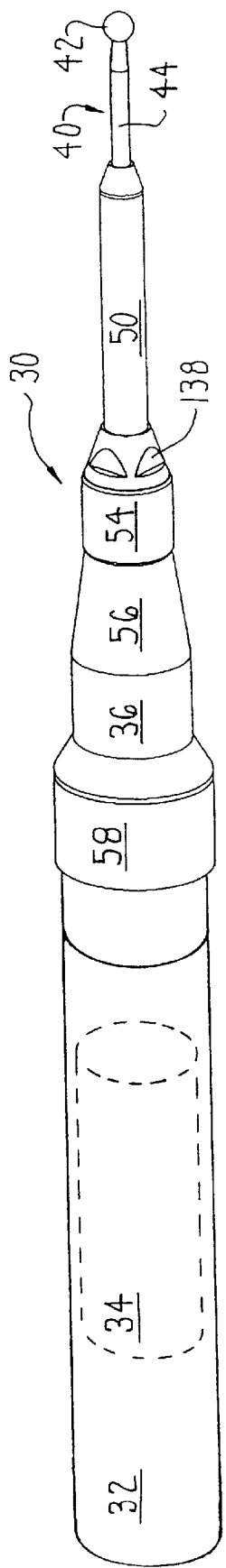
FIG. 1 is plan view of the basic components of the tool system of this invention.
Figure 2:
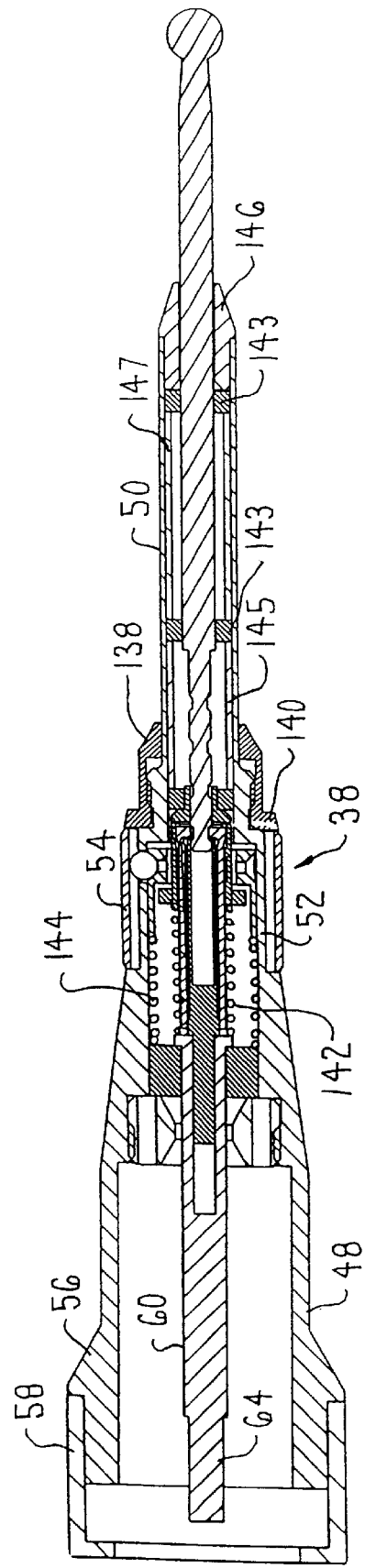
FIG. 2 is a cross-sectional view of the attachment of the tool system of this invention that contains the coupling assembly.

FIGS. 1 and 2 illustrate the basic components of the surgical tool system 30 of this invention. The system 30 includes a handpiece 32 in which a motor 34 (shown in phantom) is housed. An attachment 36 is removably fitted to the front, distal end of the handpiece. A coupling assembly 38 is disposed inside the attachment 36. Coupling assembly 38 releasably holds a cutting accessory 40 to the rest of the system 30. The coupling assembly 38 also transfers the rotational power developed by the handpiece motor 34 to the cutting accessory 40. One suitable handpiece 32 that can be employed as the handpiece of this system is described in the Applicant's U.S. Pat. No. 5,888,200, which is incorporated herein by reference. This handpiece 32 has two coupling assemblies. A first one of the handpiece coupling assemblies releasably couples a drive shaft to the rotor of motor 34 so that the drive shaft will rotate in unison with the motor rotor. A second handpiece coupling assembly integral with handpiece 32 releasably couples the attachment 36 over the proximal end of the handpiece. This second handpiece coupling assembly consists of spring feet that engage over feet that are integrally formed with and extend inwardly from the base of the attachment. A detailed description and illustrations of the coupling assemblies integral with the handpiece 32 are contained in U.S. Pat. No. 5,888,200.

The cutting accessory 40 includes a head 42. The head 42 is the portion of the cutting accessory 40 that is applied to the surgical site. A shaft 44 is formed integrally with the head 42 and extends rearwardly from the base of the head. The attachment coupling assembly 38 is releasably locked onto the cutting accessory shaft 44 to transfer the rotational power developed by the handpiece motor 34 to the cutting accessory 40. Coupling assembly 38 and shaft 44 are also collectively designed so that the extent to which the shaft extends forward of the coupling assembly can be selectively set. This selectively allows the surgeon to regulate the extent to which the cutting accessory head 42 extends forward of the handpiece 32.

Throughout this application, it should now be understood that "forward", "front" and "distal" shall mean in a direction towards the head 42 of a cutting accessory 40. "Rearward", "rear" and "proximal" shall mean in a direction towards the end of the handpiece 32 furthest from the accessory head 42.

Figure 3:
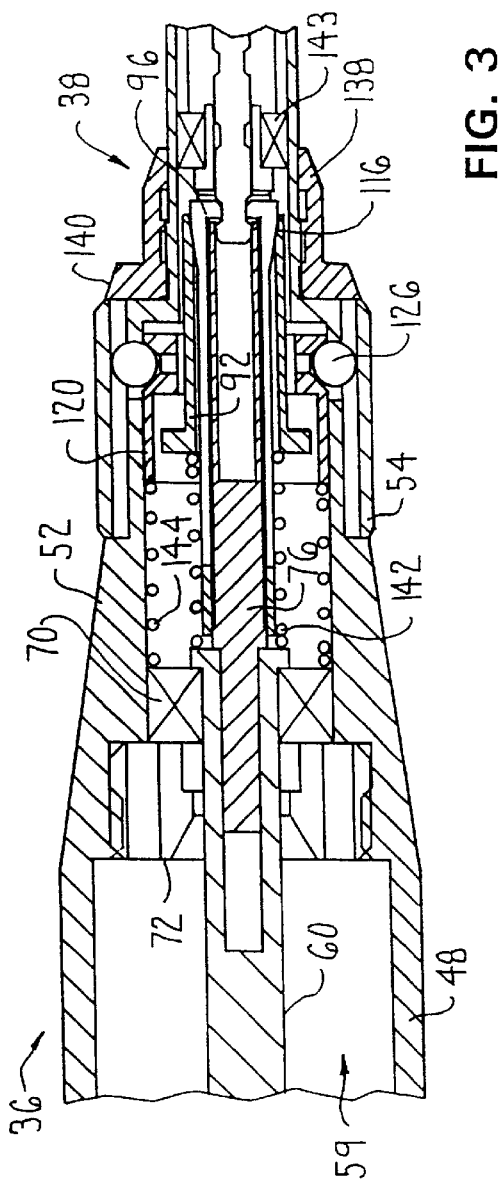
FIG. 3 is an enlarged cross-sectional view of the coupling assembly.

A detailed understanding of the structure of the attachment 36 and coupling assembly 38 is obtained by initial reference to FIGS. 2 and 3. The attachment 36 includes a housing 48 that forms the outer body of the attachment. Attachment housing 48 has a front end 50 that has an elongated tube shape. Located rearwardly of the front end 50 attachment housing 48 has an intermediate section 52. Intermediate section 52 is the portion of the attachment housing 48 in which the coupling assembly 38 is seated. A collar 54 is rotatably fitted around the intermediate section 48. The collar 54 is manually displaced to move the coupling assembly 38 between the run state in which the assembly is locked onto the cutting accessory 40 and the load state in which the cutting accessory 40 can be removed from or installed into the attachment 36. Also when the coupling assembly 38 is in the load state, the longitudinal position of the cutting accessory 40 can be selectively set. Attachment housing 48 has a base section 56 located rearward of intermediate section 52. Base section 56 is generally in the shape of an open ended tube. A ring-shaped retainer 58 is fitted around the outside of the open end of the base section 56. Retainer 58 is the portion of the attachment 36 that carries the teeth against which the second coupling assembly integral with the handpiece 32 engages. A multi-section bore 59 extends axially through housing 48.

Figure 4B:
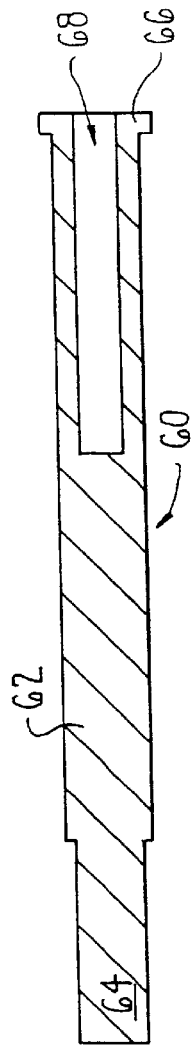
FIGS. 4A and 4B are, respectively, perspective and cross-sectional views of the input drive shaft.
Figure 4A:
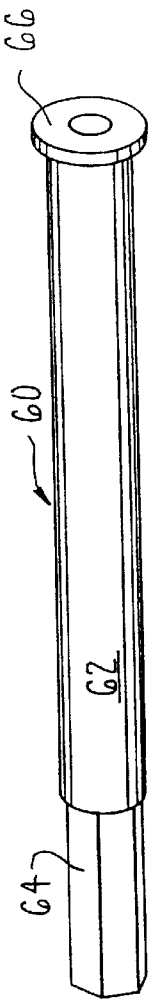

As seen in FIGS. 3, 4A and 4B, an input drive shaft 60 is rotatably fitted in housing bore 59. The input drive shaft 60 has a cylindrically shaped main section 62. A hex-shaped stem section 64 extends rearwardly from main section 62. The input drive shaft 60 is further formed to have a lip 66 that extends radially outwardly and circumferentially around the front end of main section 62. An axially extending bore 68 extends from the front end of the input drive shaft 60 through the main section 62 a distance slightly less than one-half the length of the main section. Input drive shaft 60 is located in the rear half of the housing intermediate section 52 and extends through base section 56. A bearing assembly 70 which extends between the outside of shaft main section 62 and an adjacent inner circumferential wall of housing intermediate section 52 rotatably couples input drive shaft 60 to attachment housing 48. The rearward directed face of shaft lip 66 rests against an inner race of the bearing assembly 70, (bearing assembly races not identified). A bearing retainer 72 is threadedly secured into the attachment housing 48 around the outside of shaft main section 62 immediately behind the bearing assembly 70. Bearing retainer 72 prevents longitudinal movement of the input drive shaft 60. The stem section 64 of the input drive shaft 60, it should be understood, is shaped to be locked into the first coupling assembly internal to the handpiece 32. Thus, the engagement of these two components is what transfers the rotational power developed by the handpiece motor 34 to the input drive shaft 60.

Figure 5A:
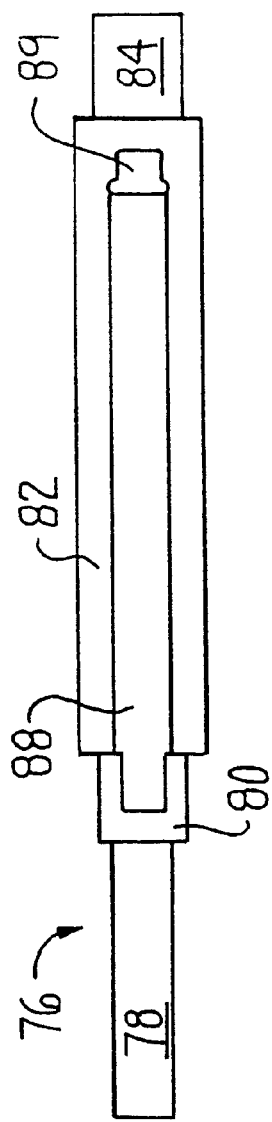
FIGS. 5A and 5B are, respectively top and cross-sectional views of the output drive shaft.
Figure 5B:
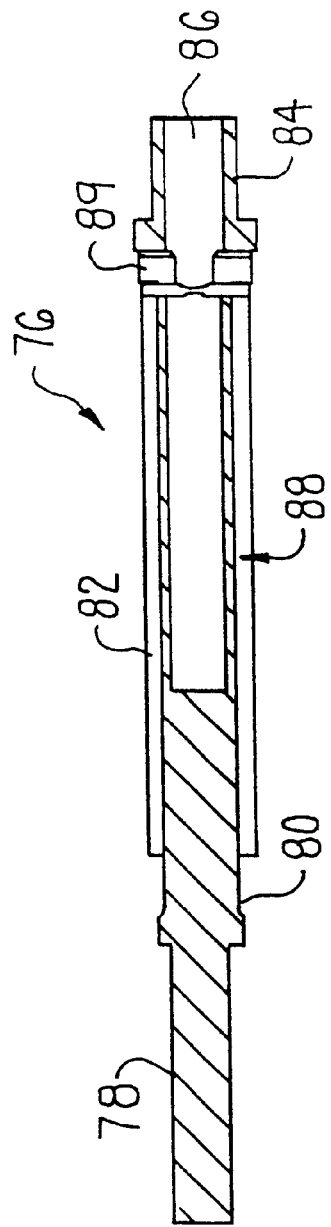

An output drive shaft 76, now described by reference to FIGS. 3, 5A and 5B, is securely fitted to input drive shaft 60. Output drive shaft 76 is formed out of a single piece of metal that is shaped to have a cylindrical, solid stem section 78. The stem section 78 of the output drive shaft 76 is press fit into the bore 68 of the input drive shaft 60 so that the two drive shafts 60 and 76 rotate in unison. Output drive shaft 76 is further formed to have a transition section 80 and a main section 82 both of which are located forward of stem section 78. Transition section 80 is located between stem section 78 and main section 82. Both transition section 80 and main section 82 are formed to have circular cross-sectional profiles. The output drive shaft 76 is formed so that main transition section 80 has a diameter greater than that of the adjacent stem section 78; main section 82 has a diameter greater than that of transition section 80. A cylindrically shaped head section 84 extends forward from the front, distal end of shaft main section 82. Head section 84 has a diameter less than that of the main section 82.

Output drive shaft 76 is formed with an axially extending bore 86 that extends rearward from the front end of head section 84. Bore 86 extends completely through head section 84 and more than half way through main section 82. The bore 86 is the space internal to the coupling assembly 38 in which the proximal, rear end of the cutting accessory shaft 44 is fitted. The output drive shaft 76 is further shaped to have two diametrically opposed, longitudinally extending slots 88. Each slot 88 is formed in both the outer surface of the transition section 80 and the adjacent surface of the main section 82. Slots 88 overlap the rear section of bore 86 but are not in communication with the bore. The output drive shaft 76 is further formed with a through channel 89 that extends diametrically through the bore main section 82. Channel 89 is contiguous with the front ends of slots 88 and extends through bore 86. Channel 89 has generally a rectangular cross-sectional profile. The width of channel 89 is less than the width of the adjacent slots 88 for a reason that will be explained hereinafter. In some versions of the invention, this difference in width is approximately 0.010 inches.

Figure 6:
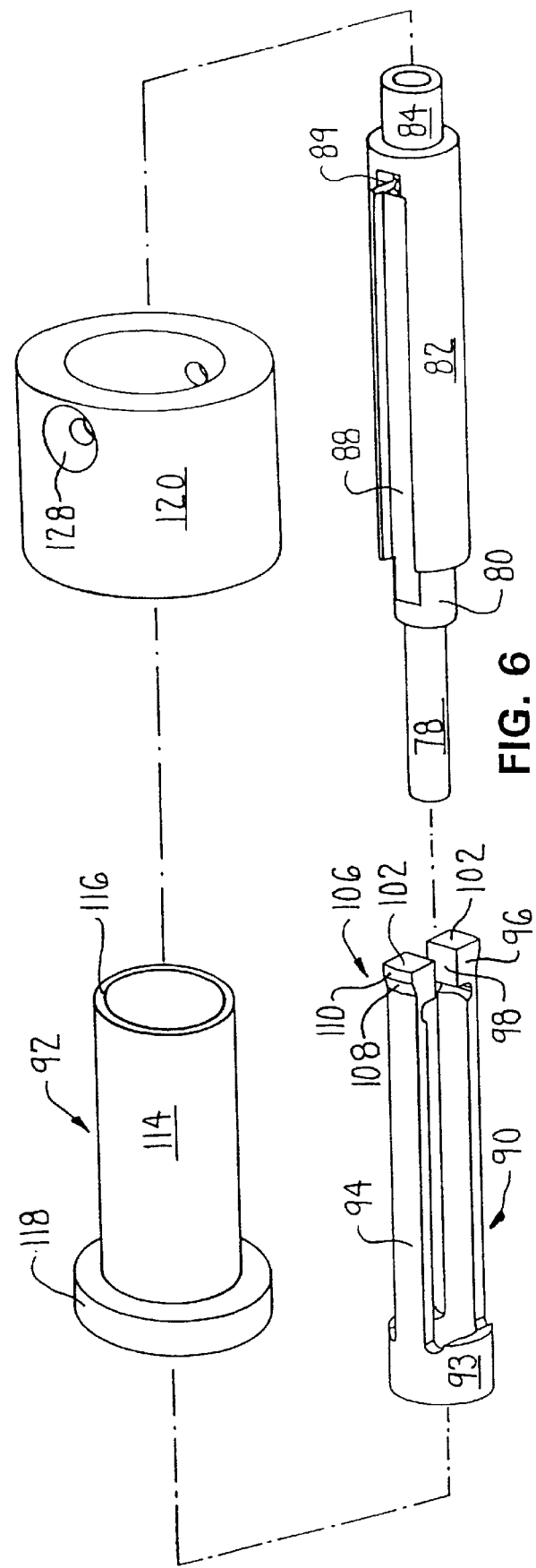
FIG. 6 is an exploded view of the inner components that form the coupling assembly.

FIGS. 3 and 6 illustrate how a collet 90 and a collet sleeve 92 cooperate to releasably lock the proximal end of the cutting accessory 40 into the output drive shaft 76. The collet 90 is fitted over the output drive shaft 76. The collet 90 is formed out of a single piece of metal such as flexible stainless steel. Collet 90 is shaped to have a ring-shaped base section 93. Two diametrically opposed legs 94 extend forward from base section 93. A foot 96 extends perpendicularly inwardly from the end of each leg 94. The feet 96 are formed to have opposed gripping surfaces 98 that are parallel with the longitudinal axis of the collet. Each foot 96 is formed to have a bottom surface 102 that is perpendicular to the longitudinal axis of the collet 90.

Collet 90 is further formed so that a multi-surfaced heel 106 is located at the end of each leg 94. Each heel 106 is shaped to have a transition surface 108 that angles outwardly away from the outer surface of the adjacent leg 94. A butt surface 110 that is parallel with and spaced outwardly away from the adjacent leg 94 forms the bottom of each heel 106. Thus, heels 106 provide thickness and structure strength to the adjacent collet feet 96. The illustrated collet 90 is shown to have semi-circular cuts that extends inwardly from the inner surfaces of the legs 94 adjacent the feet 96, (cuts not identified). These cuts are formed as a consequence of the manufacture of the collet 90 and do not form any functional part of the invention.

Collet 90 is fitted over the output drive shaft 76 so that the base section extends closely around the shaft transition section 80. Collet legs 94 seat in shaft slots 88. The collet feet 96 fit in through channel 89 and extend into shaft bore 86. Collectively, the collet 90 and shaft 96 are shaped so that collet legs 94 fit loosely in the slots 88 and collet feet 96 fit relatively tightly in the through bore 89. The loose fit of the collet legs 94 in slots 88 facilitates the seating of the feet in the slots. As will be discussed more hereinafter, the collet feet 96 engage the proximal end of the cutting accessory shaft 44 to hold the cutting accessory 40 to the output drive shaft 76.

Figure 12A:
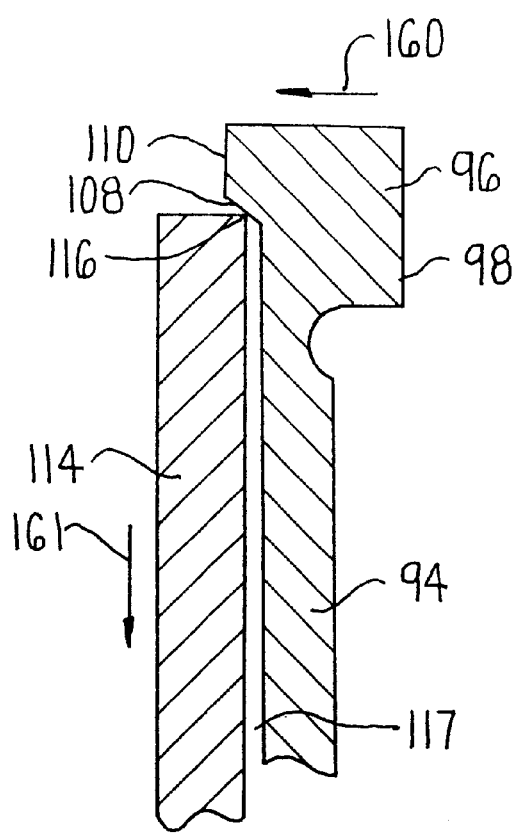
FIGS. 12A and 12B are cross-sectional views depicting how, as a result of an initial radial displacement of the collet legs and feet, the collet sleeve blocks further displacement of the collet legs and feet.

As seen in FIG. 6, the collet sleeve 92 has a generally tube-shaped body 114. The collet sleeve 92 is further formed to have an outwardly extending flange 118 that extends circumferentially around the rear, distal end of the body 114. Collet sleeve 92 has an annular edge surface 116 that is an interface between the ring-shaped front face of the sleeve and its cylindrical inner wall. The collet sleeve 92 surrounds both collet 90 and output drive shaft 76. Normally, when the coupling assembly 38 is in the run state, the collet sleeve 92 is positioned so that the collet heel transition surfaces 108 abut the edge surface 116 of the sleeve. As seen in FIG. 12A, as a result of this alignment of the components, there is a small gap 117 between the outer surface of the collet legs 94 and the adjacent inner wall of the collet sleeve 92. As a result of the dimensioning of the components, the collet sleeve 92 urges the collet feet 96 into and holds the feet in the outer drive shaft bore 86.

Figure 7:
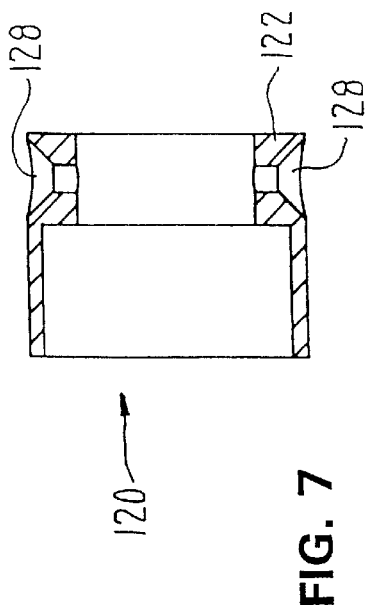
FIG. 7 is a cross-sectional view of the actuator of the coupling assembly.

An actuator 120, now described by reference to FIGS. 6 and 7, selectively displaces the collet sleeve 92 rearwardly. Actuator 120 is a generally ring-shaped member. The front end of the actuator 118 is shaped to have an inwardly directed circumferentially extending lip 122. As seen in FIG. 3, the actuator 120 is fitted over collet sleeve 92 so that the front end of the actuator, including lip 122, is located immediately forward of sleeve flange 118.

An understanding of how the actuator 120 is itself displaced is obtained by reference to FIGS. 3, 7, 8 and 8A. As seen in these figures, the actuator 120 is fitted in the attachment housing 48 so as to be closely located to the inner wall of housing intermediate section 52. This portion of the housing intermediate section 52 is formed with two opposed slots 124. A ball bearing 126 sits in each slot 124 and extends beyond the opposed outer and inner walls of the adjacent section 52 of the attachment housing 48. The portion of each ball bearing 126 that projects inwardly of the inner wall of the attachment housing 48 seats in an indentation 128 formed in the outer circumferential wall of the actuator 120. Indentations 128, it will be noted, are opposite each other and have a cross-sectional profile equal to that of a slice through a cone. (In FIG. 7 the pilot holes formed in the actuator 120 to form indentations 128 are illustrated.)

Collar 54, seen best in FIG. 8B, extends over the portion of housing intermediate section 52 in which slots 124 are formed. The inner wall of the collar 54 is formed to have two diametrically opposed grooves 132, (one shown in phantom). Grooves 132 have an arcuate cross-sectional profile and extend longitudinally along the length of the inner wall of collar 54. When the collar 54 is fitted over the attachment housing 48, the outer exposed sections of ball bearings 126 each seat in a separate one of the grooves 132. Collar 54 is dimensioned so that it is able to rotate around the attachment housing 48.

From FIG. 8A it can be seen that each slot 124 is formed to have a generally helically shaped profile. Each slot 124 is further formed to have a tail section 134 that extends upwardly diagonally away from the proximal end of the slot.

Returning to FIGS. 2 and 3, it can be observed that a nut 138 is threaded over the forward end of the housing intermediate section 52. The base of nut 138 has an outwardly directed lip 140. Lip 140 extends over the forward end of collar 54 to hold the collar to the attachment 38. A first spring 142 is located around the output drive shaft 76. More particularly spring 142 extends between the forward-directed face of inner drive shaft lip 66 and the rearwardly directed face of flange 118 of the collet sleeve 92. A second spring 144 is located around the first spring 142. Spring 144 extends between the static outer race of bearing assembly 70 and the aligned, rearwardly directed end surface of actuator 120.

Inside the front section 50 of the housing it will be observed that there are three bearing assemblies 142. A first one of the bearing assemblies is fitted around the outer drive shaft head section 84. This bearing assembly 143 provides a rotating fit between the outer drive shaft 76 and the inner wall of housing front section 50. A first tube-shaped spacer 144 separates the second bearing assembly 142 described bearing assembly 143. A second spacer 147 separates the second bearing assembly from the third, and most forward located, bearing assembly 143. A nose cap 146 is press fitted or welded into the open end of the front section 50 of attachment housing 48. Nose cap 146 is formed with an axially extending through bore, (not identified) through which the cutting accessory shaft 44 is inserted into the attachment 36.

Figure 11:
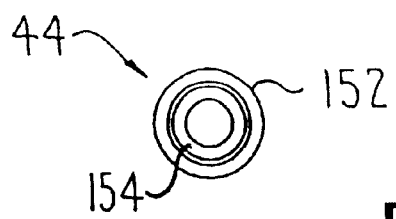
FIG. 11 is an end view of the shaft of FIG. 9.
Figure 10:
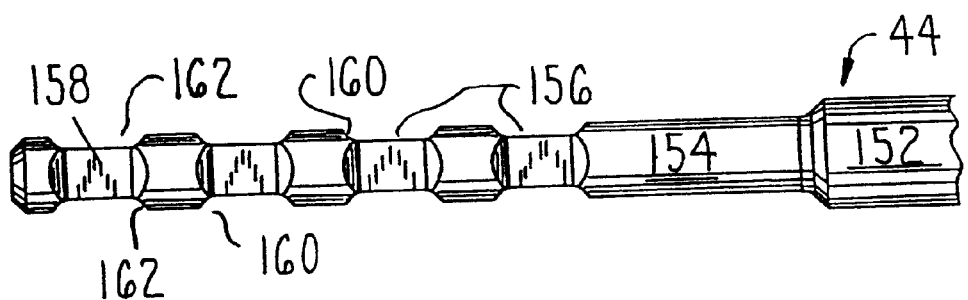
FIG. 10 is a plan view of the shaft of FIG. 9.
Figure 9:
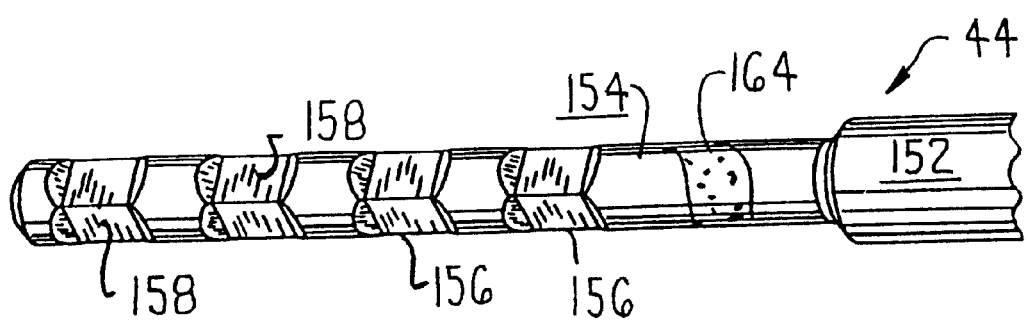
FIG. 9 is a perspective view of the shaft of a cutting accessory of this invention.

FIGS. 9, 10 and 11 illustrate the shaft 44 of the cutting accessory 40. The shaft is formed with a cylindrically shaped main body 152 that extends rearwardly from attachment head 42. In some preferred versions of the invention attachment head 42 and shaft 44 are formed out of a single piece of tool steel. Main body 152 has a constant cross-sectional diameter. In some versions of the invention, the diameter of the main body 152 is between 0.032 and 0.500 inches. In still more preferred versions of the invention, the diameter of the main body 152 is between 0.062 and 0.125 inches. Accessory shaft 44 is further formed to have a stem 154 that is formed integrally with the main body 152 and that extends coaxially rearwardly from the main body. Stem 154 is generally cylindrical and has an outer diameter that is less than the outer diameter of the adjacent shaft main body 152. In some versions of the invention, the diameter of the stem 154 is between 0.010 and 0.375 inches. In still more preferred versions of the invention, the diameter of the stem 154 is between 0.032 and 0.093 inches.

Shaft stem 154 is further formed to define a plurality of longitudinally spaced apart retention features 156. In the depicted version of the invention, each retention feature 156 consists of 4 planar faces 158 that are formed in the stem and located inwardly of the outer circumferential surface of the stem. The adjacent faces 158 intersect at 90° angles. Thus, the faces 158 collectively provide the main portion of the retention feature that they form with a square cross-sectional profile. It will further be observed that, in the illustrated version of the invention, each retention feature 156 has lower and upper beveled surfaces 160 and 162, respectively, that extend between each face and the adjacent portions of the outer circumferential surface of the shaft stem 154.

The cutting accessory 40 of this invention is coated with an anti-corrosive, sterilizable, medically innocuous material, represented by stippling 164 in FIG. 10. Some potential materials that can be applied to the cutting accessory are: titanium nitride; titanium aluminum nitride; and titanium carbonitride. The above coatings are available from BryCoat Inc. of Safety Harbor, Fla. An alternative titanium nitride coating that may be suitable is sold as ION-BOND® coating 7-22 by Multi-Arc Inc. of Rockaway, N.J., United States. Another potentially suitable coating is a chromium nitride coating sold as ION-BOND® coating 7-24 by Multi-Arc. Another potentially suitable coating is a zirconium nitride coating sold as ION-BOND® coating 7-40 by Multi-Arc. Silicon nitride may also be a suitable coating. It is believed is used, it should be applied to the cutting accessory according to the SILCOSTEEL® process employed by the Restek Corp. of Bellefonte, Pa., United States.

This material is applied to the cutting accessory 40 so as to have a maximum thickness of 0.0001 inches. The material covers the whole of the cutting accessory 40, all of the head 42 and the shaft 44. In alternative embodiments of the invention, the coating is applied only to the shaft 44, not to the head 42.

Attachment 36 is coupled to the handpiece in the same manner in which conventional attachments are so fixed. The spring feet of the handpiece second coupling assembly engage the retainer 58 to releasably secure the attachment 36 to the handpiece 32. The handpiece first coupling assembly releasably locks around the stem section 64 of input drive shaft 60. Consequently, the input drive shaft 60 is locked to the motor rotor to rotate in unison with the rotor.

When a cutting accessory 40 is fitted to attachment coupling assembly 38, accessory stem 154 is at least partially seated in the outer drive shaft bore 86. More particularly, the accessory stem 54 is aligned in the bore 86 so that the diametrically opposed faces 158 of one of the retention features 156 are aligned with the opposed gripping surfaces 98 of collet feet 96. When the coupling assembly 58 is in the normal state, the run state, spring 142 exerts sufficient force on collet sleeve 92 to push the head, distal end of the sleeve forward. Consequently, the sleeve edge surface 116 is forced against the transition surfaces 108 of the collet heels 106. This action of the sleeve bearing against the collet heels 106 forces the collet feet inwardly. Consequently, the collet gripping surfaces 98 are forced against the adjacent faces 158 of the cutting accessory retention feature 156. Since the collet legs 94 and feet 96 are seated in the output drive shaft slots 88 and through bore 89, the collet rotates with the rotation of the output drive shaft 76. Thus, owing to the engagement of the cutting accessory shaft 44 by the collet 90, the cutting accessory 40 likewise rotates in unison with the output drive shaft. It is through arrangement that the rotational power developed by the handpiece motor 34 is transferred to the cutting accessory 40. Moreover, since the collet feet 96 fit relatively tightly in the through bore 89, there is little slippage of the feet 96 when they beer against the shaft retention feature 156. Owing to the collet feet 96 bearing against the faces 158 of the cutting accessory retention features 156, the forward thrust the surgeon applies to the handpiece 32/attachment 34 is transferred through the coupling assemble to the attachment 40 and, more particularly, the attachment head 44.

It should also be understood that when the handpiece is actuated, the pressing of the accessory head 42 against the surgical site results in some rotation of the accessory shaft 44 relative to the output drive shaft 76. The retention feature faces 158 will rotate relative to the adjacent collet feet gripping surfaces 98 that are pressed against the faces 158. This rotation results in the retention features 156 pushing the collet feet 96 and heels 106 radially outwardly as depicted by arrow 160 in FIG. 12A. The outward movement of the collet feet 96 and heels 106 displaces the adjacent collet sleeve 92 rearwardly as represented by arrow 161.

Figure 12B:
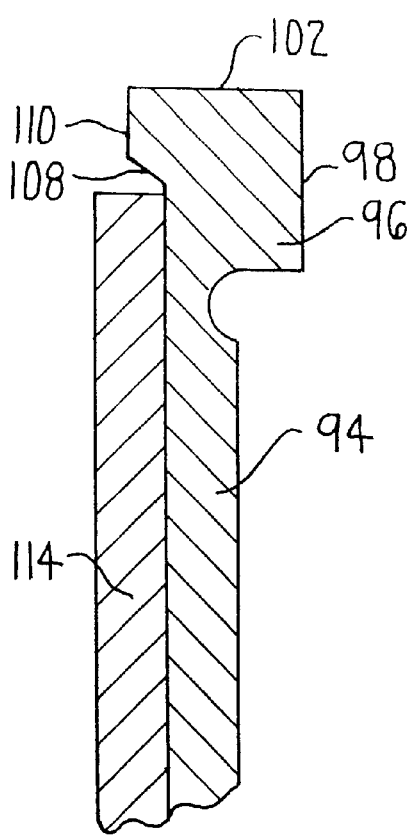

Eventually, as seen in FIG. 12B, the sleeve 92 is forced rearwardly to the level at which the inner surface of the sleeve will abut the outer surface of the collet legs 94. Once the collet 90 and sleeve 92 are so aligned, the lever action the collet legs 94 and heels 106 can impose against the collet sleeve drops to zero. Consequently, when the components of the coupling assembly 38 are so aligned, the outward movement of the collet legs 94 and feet 96 cannot overcome the force of spring 142 that holds the collet sleeve 92 in position. Since the collet sleeve 92 is itself held in position, the sleeve blocks the further outward displacement of the collet legs 94 and feet 96 which could result in the release of the cutting accessory 40 from the coupling assembly 38.

When the cutting accessory 40 is so coupled to the attachment 36, the two forwardmost bearing assemblies 143 provide a low friction interface between the accessory shaft main body 152 and the tubular front end 50 of the attachment.

It will also be understood that spring 144 works against the coupling actuator 120 to urge the actuator in the forward direction. Consequently, when the coupling assembly 38 is in the run state, the actuator 120 is spaced away from the coupling sleeve 92 so as to not longitudinally displace the coupling sleeve.

The coupling assembly is transitioned from the run state to the accessory load state by the rotation of collar 54. Prior to the rotation of the collar, the ball bearings 126 are positioned in the most forward end of the associated slots 124. The rotation of the collar 54 causes the ball bearings 126 to be displaced in the slots 124. More particularly, the ball bearings 126 undergo a rearwardly directed helical movement identical to the profile of the slots 124. Since the ball bearings 126 are fitted to actuator 120, the rearward displacement of the bearings results in a like displacement of the actuator. As a result of the rearward displacement of the actuator 120, actuator lip 122 eventually abuts the circumferential flange 118 of the collet sleeve 92. As the collar 54 continues its rotation, the actuator 120 continues to move rearwardly. This rearward movement of the actuator 120 thus forces the collet sleeve 92 to engage in a like path of travel. The rearward translation of the collet sleeve 92 results in the movement of the sleeve away from the collet feet 96 and the adjacent section of legs 94. Thus, the collet feet 96 are free to be flexed out of outer drive shaft bore 86. When the coupling assembly 38 is in this position, the assembly is considered to be in the accessory load state.

The continued rotation of the collar 54 causes the ball bearings to travel into the tail sections 134 of slots 124. When the coupling assembly 38 is in this state, the actuator 120 is still positioned to hold the collar sleeve 92 so that the collet feet 96 are free to flex out of the outer drive shaft bore 86. Also, when the coupling assembly 38 is in this state, spring 144 continues to urge the actuator 120 in the forward direction. When the coupling assembly 38 is in this state, it should be further understood that the collet sleeve flange 118 continues to abut actuator lip 122. Spring 142, it will be recalled, continually urges the collet sleeve 92 forwardly. Thus, the force spring 142 exerts on the collet sleeve 92 is imposed on the actuator 120. Thus, the forces generated by springs 142 and 144 collectively urge actuator 120 forward so that the ball bearings 126 lock in the upper ends of the slot tails 134. Thus, when the coupling assembly 38 is so set, the assembly is locked in the accessory load state.

When the coupling assembly 38 is in the load state, the accessory shaft stem 154 can be extended out of or pushed further into the outer drive shaft bore 86. Thus, the extent to which the accessory shaft 44 extends out of the front of the attachment 36 can be selectively set. Specifically, it can be set to a position in which the faces 158 of one of the shaft's retention features 156 is in registration with the collet gripping surfaces 98. Also, the cutting accessory 40 can be completely removed from the attachment 38 and a new accessory fitted to, loaded into, the attachment.

When the coupling assembly 38 is in the load state, the collet feet 96 may still extend a small distance into the outer drive shaft bore 86. During the extension and retraction of the cutting accessory 40, the feet will abut against the outer surface of the shaft stem 154. However, since the shaft is formed with flat, beveled surfaces, the feet 96 do not lock on planar surfaces formed on the outer surface of the shaft stem 154. Instead the feet ride along the beveled surface to allow the cutting accessory 40 to be fitted into and removed from the attachment 38.

Once a cutting accessory is properly fitted into the attachment 38, collar 54 is manually rotated to return coupling assembly 38 back to the run state. As a consequence of this movement of the collar 54, ball bearings 126 travel out of the tail sections 134 of the slots 124 and into the main sections of the slots. This displacement of the ball bearings 126 allows spring 144 to force the actuator 120 back to its fully forward position. The return of the actuator 120 to the fully forward position releases the blocking force the actuator placed on the collet sleeve 92. Spring 142, in turn, then forces the collet sleeve 92 forward so that the sleeve edge surface 116 abuts the collet heel transition surfaces 108. This action thus returns the collet and the rest of the coupling assembly 38 to the run state. It will be noted that, when the coupling assembly 38 is in the run state with a cutting accessory 40 in place, the distance between the butt surfaces 110 of the collet heels 106 is greater than the inner diameter of the forward end of the collet sleeve 92. Thus, the collet heels 106 prevent collet sleeve from riding up over the forward end of the collet 90.

The coupling assembly 38 and complementary accessory shaft 44 of the tool system 30 of this invention do more than simply allow different accessories to be used with a single handpiece 32. Coupling assembly 38 and accessory shaft 44 are designed so that the extent to which the accessory head 42 extends forward from the handpiece 32 can be selectively set. This feature eliminates the need to provide a number of different accessories that have the same type of head 42 and that differ only in the length of their shafts 44.

Still another feature of system 30 of this invention, is that the coupling assembly 38 can be locked in the accessory load state. Thus, when changing cutting accessories 40 or adjusting the extent to which an accessory extends forward from the handpiece 32, medical personnel do not need to apply force to hold the coupling assembly 38 in the load state. The ability to avoid having to perform this task simultaneously with the removal, insertion or adjustment of the cutting accessory 40 facilitates the quick execution of these latter tasks.

Still another feature of the system 30 of this invention is that the accessory shaft 44 is formed from two sections of differing diameter. The wide diameter main section 152 provides the shaft 152 with structural strength. Also, the shaft main section 152 is designed to fit with bearing assemblies 142 that have inner races that have a relatively wide inner diameter. These bearing assemblies 142 are more economical to provide than assemblies with narrower inner diameters. The narrow diameter stem section 154 of the accessory shaft 44 is dimensioned, however, to fit in a relatively narrow diameter outer drive shaft bore 86. Since the bore 86 is of narrow diameter the outer drive shaft as well as the surrounding components can be likewise shaped to have a relatively narrow overall width. The benefit of this feature of the invention will be discussed in more detail in regard to the below-described additional attachments of this invention.

The cutting accessories 40 of the system 30 of this invention are covered in a protective coating. If an accessory is not used, it may be exposed to autoclave sterilization; the coating will prevent the tool steel from which the accessory 40 is formed from discoloring. Thus, even though an accessory of this invention is taken out of its sterile package, the accessory can be sterilized so that it will be available for use in a later procedure. If the accessory is so sterilized, the protective coating does not discolor. Thus, after autoclave sterilization, the accessory of this invention does not have an aesthetically displeasing appearance that would make surgical personnel reluctant to use the tool.

An alternative attachment 170 of the system 30 of this invention is illustrated in FIG. 13. Attachment 170 has an extend-length head tube 172. This attachment 170 is used to position the head 42 of a cutting accessory 40 at locations that cannot be reached when the accessory is fitted to attachment 36. A detailed understanding of the components internal to attachment 170 is obtained by initial reference to FIGS. 14 and 15. Attachment 170 includes a housing 174 that forms the body of the attachment. Head tube 172 is attached to the front of the housing 174. A coupling assembly 176 is located in the head tube 172 for rotatably and releasably holding the accessory shaft 44 in the head tube. Coupling assembly 176 also transfers the rotational power developed by the rotor integral with the handpiece motor 34 to the cutting accessory 40. As described hereinafter, some components of the coupling assembly 176 are located in the housing 174.

The housing 174 has a base 178 similar in shape to the base section 56 of previously described and illustrated housing 48. A retainer 58 is fitted around the outside open end of attachment housing base 178. Located forward of base 178, housing 174 is formed to have a neck 180. Housing 174 is shaped so that neck 180 has a generally constant diameter cylindrical outer surface. Base 178 is shaped to have a frusto-conical section 182 located immediately rearward of the neck 180 and generally constant diameter cylindrical section 184 that extends rearwardly from frusto-conical section 184. An axially extending multi-section bore 187 extends through the housing from the front of the neck 180 to the rear end of the base 178.

Head tube 172 is seated in the front end of the housing bore 187 and extends forward from the housing 174. The head tube 172 is formed to have a flange 188 that extends radially outwardly and circumferentially around it rear end. When head tube 172 is seated in housing 178, flange 188 abuts the annular front face of housing neck 180 to limit the extent to which the head tube is seated in housing bore 187. A sleeve-like nut 190 is threadedly engaged with complementary threading formed on the housing neck 180 immediately rearward of the front face of the neck, (threading not identified). Nut 190 is formed with a lip 191 that extends over the forward facing surface of tube flange 188. Nut 190 thus presses against flange 188 to secure head tube 172 to housing 174.

An input drive shaft 192, now described by reference to FIGS. 15, 16A and 16B, is rotatably fitted in housing 174. Input drive shaft 192 has a solid cylindrical main body 194. Extending rearwardly from main body 194, the input drive shaft 192 has a hex-shaped stem section 196. Stem section 196 of input drive shaft 192 has the same shape and performs the same function as stem section 64 of previously described input drive shaft 60. The input drive shaft 192 is further formed to have an annular lip 198 that extends radially and circumferentially around the main body 194 a slight distance in front of the front end of the main body. Input drive shaft 194 also has a cylindrical neck 202 that is coaxial with and extends forward from the main body 194. The input drive shaft is formed so that the outer diameter of neck 202 is less than the outer diameter of the adjacent main body 194.

Input drive shaft 192 is also formed to have a bore 204 that extends axially rearward from the front end of the neck 202. Bore 204 extends through neck 202 and a short distance into the main body 194 of the shaft 192. It will be noted that the shaft 192 is formed so that lip 198 is located a slight distance rearwardly of the base of bore 204. The input drive shaft is further formed with a pair of diametrically opposed slots 208 that are located around bore 204. Slots 208 extend inwardly from the outer surface of shaft main body 194 and are in communication with bore 204.

A bearing assembly 209 rotatably couples input drive shaft 192 in bore 187 of attachment housing 174. Shaft lip 198 abuts the forward directed surface of the inner race of the bearing assembly 209, (races not illustrated). A bearing retainer 210 is fitted around the portion of shaft main body 194 located immediately rearward of the bearing assembly 209. The bearing retainer 210 is threadedly secured to an adjacent inner wall of the housing 174 that defines bore 187. The bearing retainer 210 holds the input drive shaft 192 in position.

Coupling assembly 176 includes an output drive shaft 214, now described by reference to FIGS. 15, 17 and 18, in which the accessory shaft stem 154 is releasably secured. The output drive shaft 214 is generally cylindrically shaped and is formed to have a tail section 216 that has a first outer diameter. A bore 218, depicted in phantom in FIG. 17, extends forward from the rear end of the tail section 216 partially through the tail section. Output drive shaft 214 is further formed so as to have a pair of opposed, elongated, oval-shaped grooves 220 in the tail section. Grooves 220 are located around bore 218 and are in communication with the bore 218. Output drive shaft 214 has a main section 222 located forward of tail section 216. Main section 222 has an outer diameter greater than that of the tail section. The output drive shaft 214 also has a neck 224 located forward of main section 222 and a head 226 located forward of the neck 224. Output drive shaft 214 is formed so that neck 224 has an outer diameter less than that of main section 222 and head 226 has an outer diameter less than that of the neck.

An elongated bore 228 extends axially and rearwardly through shaft 214 from the front end of head 226. Bore 228 extends through head 226 and neck 224 and partially through main section 222. Bore 228 is sized and shaped to receive the accessory shaft stem 154. The output drive shaft 214 is further formed to have two diametrically opposed slots 230. Slots 230 extend from a forward portion of shaft tail section 216, through main section 222 and partially through neck 224. The forward portions of slots 230 surround the longitudinal section of the shaft 214 in which the tail end of bore 228 is formed. Slots 230, however, do not directly communicate with the bore 228. The output drive shaft 214 is also formed with a through channel 231. The through channel 231 is located adjacent the front ends of the slots 230, extends diametrically through the shaft 214 and intersects bore 228.

Bearing assemblies 234 extend around shaft tail 216 and shaft head 226. The bearing assemblies rotatably hold the output drive shaft in the head tube 172.

FIG. 18 depicts how the output drive shaft 214, a collet 238 and a collet sleeve 240 cooperate to form the forward-located components of coupling assembly 176. Collet 238 is formed of the same material, and has the same general function, as the previously described collet 90. Collet 238 has a ring-shaped base 242. Two diametrically opposed legs 244 extend forward from base 242. An inwardly directed foot 246 is located at the end of each leg 244. Each foot 246 has a gripping surface 247. The collet 238 is formed so that gripping surfaces 246 are parallel with the longitudinal axis of the collet. The collet 238 is further formed to have a small heel 248 between the end of each leg 244 and the associated foot 246. Each heel 248 is shaped to have a first beveled surface 250 that extends diagonally outwardly and forwardly away from the outer surface of the associated leg 238. The heel 248 has a flat surface 252 that extends forward from the first beveled surface. Collectively, the flat surfaces 252 of the ankles 248 are parallel with each other. Each ankle 248 also has a second beveled surface 254. Beveled surfaces 254 extend forwardly and inwardly relative to the flat surfaces 252 with which the beveled surfaces 254 are contiguous. The beveled surfaces 254 terminate at the exposed, front-facing ends of the collet feet 246.

The collet base 242 is fitted over the tail section 216 of the output drive shaft 214. The collet 238 is fitted to the output drive shaft 214 so that collet base 242 is located forward of shaft grooves 220. The collet legs 244 are seated in the opposed slots 230 formed in shaft 214. The collet feet extend into the through channel 231 and project into shaft bore 228.

Collet sleeve 240 is a generally tube-shaped structure. As seen in FIGS. 18 and 19, coaxial holes 258 are formed in the rear end of the sleeve 240. The collet sleeve 240 is further shaped to have diametrically opposed windows 260 located rearward of the front end of the sleeve. Windows 260 are generally rectangular shaped and longitudinal axes that are parallel with the longitudinal axis of the sleeve 240. The collet sleeve 240 is further formed so that adjacent the front end of the sleeve, the inner wall has a lip surface 262. Lip surface 262 has a constant diameter that is less than the diameter of the remaining sections of the inner wall of the sleeve 240. A tapered transition surface 264 extends circumferentially around the sleeve 240 adjacent lip surface 262. The diameter of the inner wall of the sleeve located rearwardly of transition surface 264 is constant.

Collet sleeve 240 is slip fitted over both output arrive shaft 214 and collet 238. When the coupling assembly 176 is in the run state, the collet sleeve 240 is initially positioned so that transition surface 264 abuts the second beveled surfaces 254 of the collet 238. When the coupling assembly is in this state, as seen by FIG. 21A, there is a small interstitial gap 249 between the collet flat surfaces 252 and the adjacent, constant diameter inner wall of the collet sleeve 240. Owing to the dimensioning of the components, when the collet sleeve 240 is in this state, the sleeve thus holds the collet feet 246 in the shaft bore 228.

It will further be understood that the collet sleeve 240 is further positioned over the collet 238 so that the sleeve windows 260 are in registration with the collet legs 244. Also, the holes 258 located in the rear end of the collet sleeve 240 are in registration with grooves 220 formed in the drive shaft tail section 216.

A push rod 262, now described by reference to FIGS. 15 and 20, selectively displaces the collet sleeve when the coupling assembly 176 is in transition from the run state to the accessory load state. The push rod 262 is a generally solid cylindrical member that extends from the housing neck 180 into the head tube 172. The most rearwardly located section of the push rod 262 is the tail 263. The tail 263 is formed with a through hole 264 that extends laterally through the tail. Immediately forward of tail 263, push rod 262 is formed to have a first intermediate section 266. The longest section of the push rod 262 in terms of length, is the main section 268 which is located immediately forward of the first intermediate section 266. The push rod 262 is shaped so that the outer diameter of the first intermediate section 266 is greater than the outer diameter of the tail 262; the main section 268 has an outer diameter greater than that of first intermediate section 266. A second intermediate section 270 extends forward from the front of the main section 268. The push rod 262 is further formed to have a head 272 that extends forward from second intermediate section 270. The push rod 262 is further shaped so that the second intermediate section has an outer diameter less than that of the main section 268. The head 272 of the push rod has an outer diameter less than that of the adjacent second intermediate section 270. Push rod 262 is further formed so that a through hold 274 extends laterally through the center of the head 272.

The push rod 262 is assembled into attachment 170 so that the rod tail 263 is slideably fitted inside bore 204 of the input drive shaft 192. A pin 276 extends through the drive shaft slots 208 and rod through hold 264. Pin 276 thus connects the push rod 262 to the input drive shaft 192 so that the rod rotates with the shaft. However, pin 276 is dimensioned to be able to slide relative to slots 208. Thus, push rod 262 is capable of a limited degree of longitudinal movement relative to the input drive shaft 192. Pin 276 is dimensioned so that the ends of the pin extend beyond the outer surface of the drive shaft neck 202. The opposed ends of pin 276 are seated around an annular retaining ring 277. Ring 277 is fitted around the outside of drive shaft neck 202. The ring 277 is dimensioned so that it is able to move longitudinally relative to the input drive shaft 192. The retaining ring 277 is provided with diametrically opposed holes, (holes not identified). When the attachment 170 is assembled, the opposed ends of pin 276 are press fit into the holes of the retaining ring 277.

The head 272 of the push rod 262 is seated in the bore 218 formed in the tail section 216 of the output drive shaft 214. A pin 278 extends through collet sleeve holes 258, outer drive shaft grooves 220 and rod through hole 274. Pin 278 thus connects the push rod 262 to the drive shaft 214 so that these two components will rotate in unison and so that the rod is able to move longitudinally relative to the drive shaft. The pin 278 also connects the push rod 262 and the collet sleeve 240 together so that these components both rotate together in unison and engage in the same longitudinal movement.

An actuator 282 located in the housing neck 180 longitudinally displaces the push rod 262. Actuator 282 is similar in shape to previously described actuator 130. Actuator 282 typically will be smaller in diameter than actuator 120. Actuator 282, it will be observed, is fitted over the neck 202 of the input drive shaft 192 so as to surround the push rod tail 262 and pin 276. A forward facing lip surface 284 of the actuator 282 is located in close proximity to the retaining ring 277.

Housing neck 180 is formed with slots 286 similar to previously described slots 124 (FIGS. 8 and 8A). A collar 288 essentially identical to collar 54 is rotatably located over the housing neck 180. Nut 190 holds collar 288 onto the housing 174.

A ball bearing 287 is seated in each slot 286. Each ball bearing 287 has one end that is seated in the indentation formed in the actuator (indentation not identified). The opposed end of each bearing is seated in a groove 292 formed in the collar 288. Slots 286, it should be understood, are arranged so that when the coupling assembly 176 is in the run state, the ball bearings are located in close proximity towards the housing base 178. Slots 286 are further shaped so that, as the collar is rotated to move the coupling assembly to the accessory load state, the bearings 126 will be displaced forwardly towards the front end of the attachment 170.

Additional bearing assemblies 234 provide low friction, rotating interfaces between the components of the moving components of attachment 170 and head tube 172. One bearing assembly 234 extends between input drive shaft neck 202 and the head tube 172. Two spaced apart bearing assemblies 234 rotatably hold the push rod main section 268 in the head tube. Additional bearing assemblies 234 provide a low friction interface between the attachment shaft main section 152 and the head tube 172. Spacer sleeves 294 slip fit in the head tube 172 hold the bearing assemblies 234 apart from each other.

A spring 298 extends between the output drive shaft 214 and the push rod 262. More particularly, spring 298 extends between a first washer 299 disposed around push rod 298 that abuts the tail end of the drive shaft 214 and a second washer 302 seated against a stepped surface of the push rod between main section 268 and second intermediate section 270. A second spring 306 extends between an inwardly directed annular step 308 formed in the attachment neck 180 and the actuator 282. Specifically, spring 306 abuts the annular, front facing surface of the actuator 282.

Normally, spring 298 works against push rod 262 so as to push the push rod rearward, towards the input drive shaft 192. The push rod 298, in turn, forces the collet sleeve 240 to engage in a similar, rearward, displacement. Consequently, the surface 264 of the sleeve 240 is urged against the second beveled surfaces 254 of the collet ankles 248. This latching action serves to hold the collet feet 246 inside output drive shaft bore 248. When a cutting accessory 40 is seated in bore 228, the gripping surfaces 247 of the collet feet 246 thus bear against the adjacent faces 158 of the accessory stem 154 so as to hold the accessory in the output drive shaft 214. Spring 306, it will be noted, urges actuator 282 rearward. Consequently, the lip surface of the actuator 282 is held away from the retainer ring 277. Thus, the actuator 282 is prevented from unintentionally striking the retaining ring 277 which would cause the inadvertent longitudinal displacement of the push rod 298 and collet sleeve 240.

When the attachment 170 of this version of the invention is coupled to the handpiece 32, input drive shaft 192 is rotatably coupled to the rotor integral with the handpiece motor 34. The push rod 298 transfers the rotational movement of the input drive shaft 192 to both the output drive shaft 214 and collet sleeve 240. Owing to the seating of the collet legs 244 in the slots 230 and the seating of the collet feet 246 in the through channel 231, the collet 238 is forced into a likewise rotational motion. Thus, when a cutting attachment 40 is locked into the output drive shaft 214, it undergoes the same rotational motion experienced by the drive shaft 214.

When the cutting accessory 40 is pressed against the surgical site, there may be some rotation of the accessory shaft 44 relative to output drive shaft 214. When this occurs, the collet feet 246 may be pushed radially outwardly against the collet sleeve 240 as represented by arrow 311 of FIG. 21A. Owing to the relationship collet surface 254 to collet sleeve surface 264, the movement of the collet feet 246 results in the forward displacement of the collet sleeve 240, represented by arrow 312. The displacement of the collet sleeve 240 results in the constant diameter section of the inner wall of the sleeve adjacent surface 264 from going into registration with and abutting the flat surfaces of the collet 238 as seen in FIG. 21B. Once the components of the coupling assembly 176 are so aligned, the lever angle against which the collet feet 246 are pushing falls to zero. Thus, when the collet 238 and the sleeve 240 are in this orientation, the collet feet 246 are no longer able to exert a force on the sleeve that will result in the displacement of the sleeve to the accessory load state.

The coupling assembly 176 of this version of the invention is displaced from the run state to the accessory load state by the manual rotation of collar 288. The rotation of the collar 288 causes the ball bearings 126 to move in a generally forward direction in the slots 286 in which the ball bearings are seated. The movement of the ball bearings 126 forces a like, forward movement of the actuator 282. As a result of this forward movement, the actuator 282 strikes the retaining ring 277. As the actuator 282 continues to move forward, it causes the retaining ring 277 and therefore also the push rod 262 to engage in a like forward translational motion. The push rod 262, in turn, forces the collet sleeve 240 to move in the same general direction. As a result of the displacement of the collet sleeve 240, the sleeve windows 260 are displaced to the point at which they come into registration over the ends of the collet legs 244 and the feet 246. When the collet sleeve 240 is so positioned, the legs 244 and feet 246 are free to flex out of the drive shaft bore 228. Since the collet feet are not locked against one of the stem retention features 156, the accessory stem 154 can be removed from, inserted into or repositioned in the output drive shaft 214.

Attachment 170 of the system 30 of this invention is used when it is necessary to position the head 42 of the cutting accessory 44 more forward of the handpiece 32 than it can be positioned when using attachment 36. It will be noted that, while a portion of the attachment coupling assembly 176 is located in head tube 172, the mechanism that takes the assembly 176 in and out of the run state is mounted to the housing 174. This arrangement makes it possible to keep the diameter of the head tube relatively small. For example, in some preferred versions of the invention, the outer diameter of the head tube 172 is 0.313 inches or less, in more preferred versions of the invention, the outer diameter of the head tube 172 is 0.235 inches or less and, in still more preferred versions of the invention, the outer diameter of the head tube 172 is 0.125 inches or less. An advantage of the head tube 172 having such a small diameter is that it reduces the extent to which the head tube obstructs the surgeon's field-of-view of the surgical site.

Moreover, in some versions of the invention, the head tube 172 may be formed with a tapered profile. An advantage of these versions of the invention is that the extent to which the forward end of the attachment 170 obstructs the field-of-view of the surgical site is even further reduced.

Still another feature of this invention is that it will be recognized that collet 238 is positioned in head tube 172 a select distance from the distal end of the head tube. Specifically, this distance is such that it is possible for cutting accessory 40, with its single-length shaft 44, be held to attachment 36 by collet 90 and also held to attachment 170 by collet 238. Thus cutting accessories having shafts that have a single, common length can be used with both the medium and long length attachments of this invention.

Figure 22:
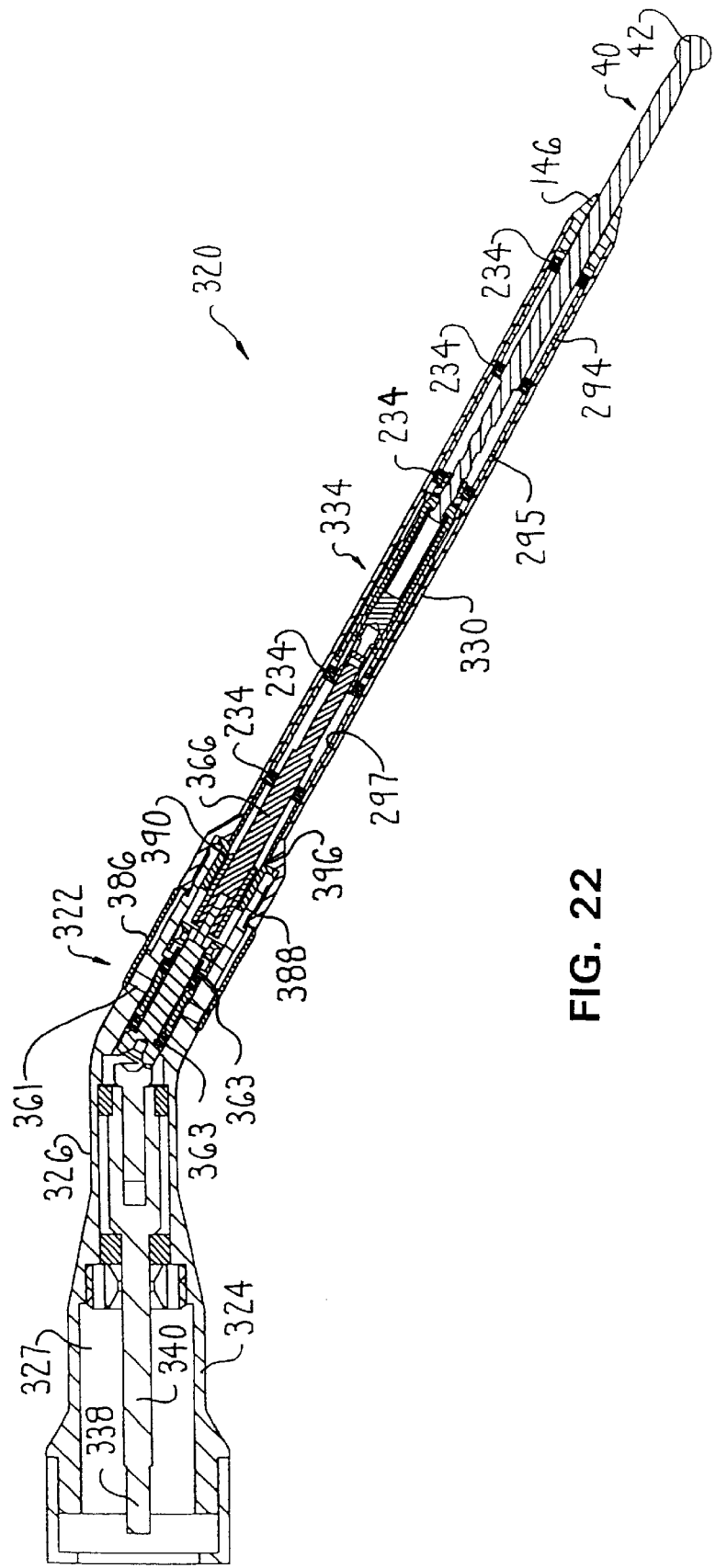
FIG. 22 is a cross-sectional view of an angled attachment of the tool system of this invention.
Figure 23:
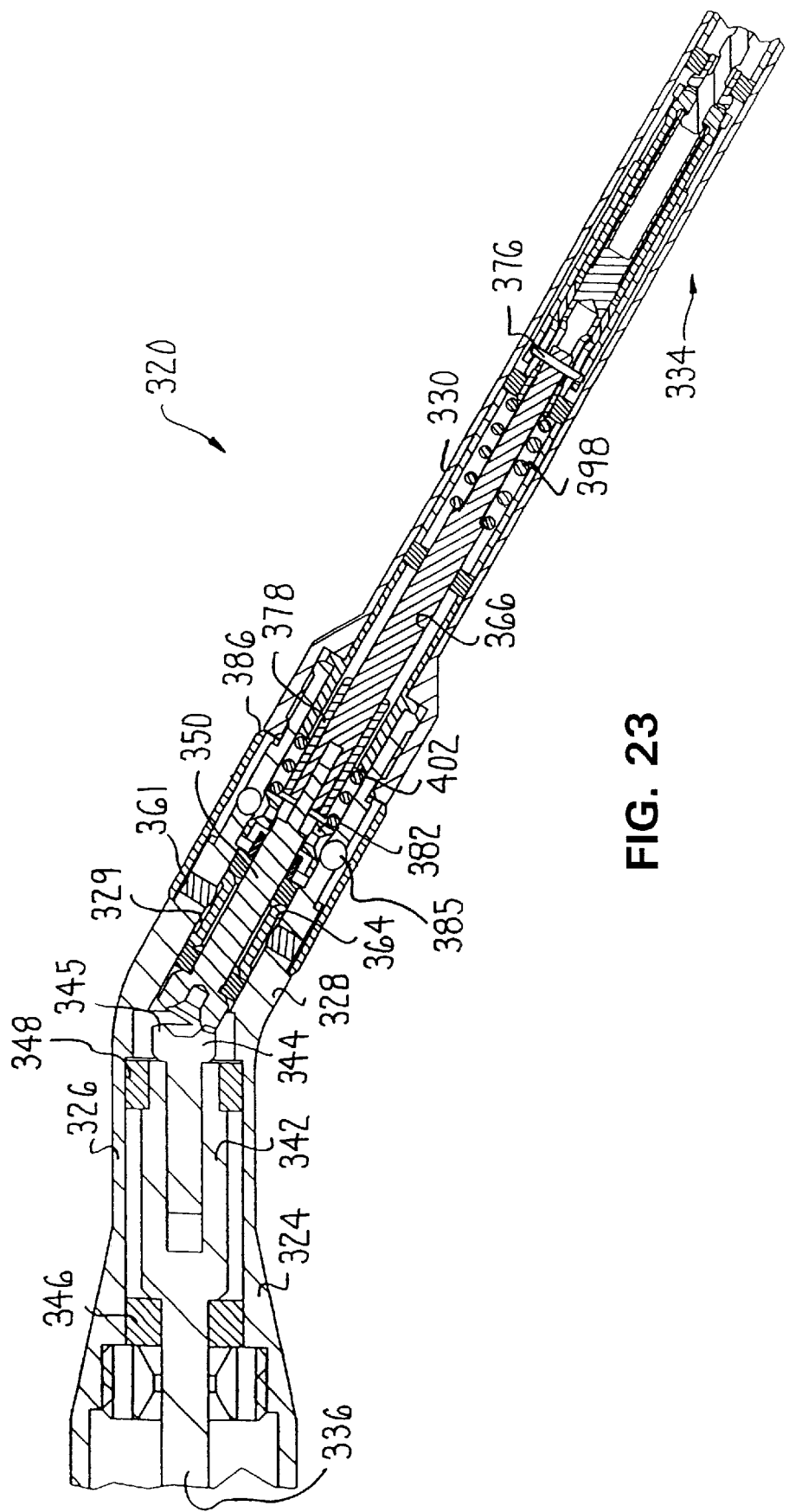
FIG. 23 is an enlarged cross-sectional view of the attachment of FIG. 22.

An angled attachment 320 of the system 30 of this invention is depicted in FIGS. 22 and 23. Attachment 320 is used by surgeons that want to apply the head 42 of the cutting accessory 40 to the surgical site along an axis that is angled from the longitudinal axis of the handpiece 32. Often a surgeon uses this type of attachment 320 for ergonomic reasons or to minimize the extent the handpiece obstructs the field-of-view of the surgical site.

Attachment 320 includes a housing 322. This housing may be formed from a single piece of metal or from plural workpieces that are secured together. Housing 322 is shaped to have a base 324 similar to base 178 of attachment 174. Not illustrated is the retaining ring that is fitted over the open end of the base 324. Housing 322 is further formed to have a shoulder 326 and a neck 398 that are located forward from the base 324. The shoulder 326 is located immediately forward of the base 324 and is coaxially aligned with the base. Neck 328 extends forward from shoulder 326 and is angularly offset from the shoulder. A multi-section bore 327 extends axially through housing base 324 and shoulder 326. A multi-section bore 329 extends axially through housing neck 328. Bores 327 and 329 are in communication with each other. A head tube 330 extends forward from the open end of housing neck 328. A coupling assembly 334 is mounted in the neck 328 and the head tube 330 for releasably and rotatably holding the cutting accessory 40 in the head tube.

An input drive shaft 336 is rotatably mounted in housing base 322. The input drive shaft 336 includes a stem section 338 similar in shape and identical in function to previously described stem section 196. Forward of stem section 338, input drive shaft 336 is formed to have a cylindrical leg 340. Forward of leg 340, the input drive shaft 336 has a cylindrical shoulder section 342. The input drive shaft 336 is formed so that shoulder section 342 is wider in diameter than leg 340. The input drive shaft also has a head 344 that extends forward from and is integrally attached to shoulder section 342. Drive shaft head 344 has a circular cross-sectional profile and a diameter less than the diameter of the shoulder section 342.

The stem section 338 and leg 340 of the input drive shaft 336 are located in the base 324 of attachment housing 322. The shoulder section 342 and head 344 of the shaft are located in the housing shoulder 326. Bearing assemblies 346 and 348 rotatably secure the input drive shaft 336 in the attachment housing 322. Bearing assembly 346 is fitted around the portion of shaft leg 340 located adjacent shoulder section 342. Bearing assembly 348 is located against a stepped surface of the shaft 336 between shoulder section 342 and head 344.

As will be discussed below, the drive shaft head 344 is provided with gear teeth 345.

An intermediate drive shaft 356 is rotatably secured in the bore 329 of housing neck 328. The intermediate drive shaft 356, seen best in FIGS. 23 and 24, is formed to have a large diameter base 358 that is located adjacent input drive shaft head 344. Base 358 is provided with teeth 359 that engage the gear teeth 345 of head 344. Gear teeth 345 and 359 are beveled to facilitate the transfer of rotational power from shaft 336 to shaft 356 even though the longitudinal axes of the shafts are angled relative to each other. Forward of base 358, the intermediate drive shaft 356 has a main body 360 that is cylindrical in shape and that has an outer diameter less than that of the base. The intermediate drive shaft 356 is also formed to have a head 362 that extends forward from the base 360. Shaft head 362 is shaped to have a tongue-like shape. That is while the sides of the head 362 have an arcuate profile, the top and bottom surfaces of the head are flat and coplanar.

In one preferred method of manufacturing the invention, the stem section 338, leg 340, shoulder section 342 and the rear portion of head 344 of the input drive shaft 336 are formed from a single workpiece. A bore, (not identified), is formed in the workpiece so as to extend rearwardly from the shoulder section 342. A second workpiece that could function as an intermediate drive shaft is press fit in the bore. As a result of this assembly process, the teeth, which would normally be the base teeth of the intermediate drive shaft, instead function as teeth 345 of the input drive shaft 336. An advantage of this method of manufacture is that it eliminates the expense of having to form teeth in the shaft head 344.

Two bearing assemblies 363 rotatably secure intermediate drive shaft 356 in bore 329. The inner race of the most rearward of the two bearing assemblies 363 is seated against the shoulder between the shaft base 358 and main body 360. The forward one of the bearing assemblies 363 extends around a more forward section of shaft main body 360. A tube-shaped spacer 364 holds the bearing assemblies apart from each other. The spacer 364 bears against the inner wall of the housing 322 that defines bore 329. Two set screws 361 bear against the spacer 364 to hold the spacer in place. Set screws 361 extend through openings in the housing shoulder 326, (openings not identified).

As discussed above, the attachment coupling assembly 334 is partially located in head tube 330. Coupling assembly includes the output drive shaft 214, the collet 238 and collet sleeve 240 previously described with respect to coupling assembly 176. Bearing assemblies 234 fitted around shaft tail 216 shaft head 226 provide a low-friction interface between the shaft 214 and the adjacent inner wall of head tube 330.

A push rod 366, now described by reference to FIGS. 23 and 25, rotatably connects intermediate drive shaft 356 to the associated output drive shaft 214. Push rod 366 is in the form of a solid, cylindrical rod. The push rod 366 is shaped to have a main section 368 that has a constant outer diameter. The push rod 366 is further formed so as to define an elongated rectangular slot 370 that extends forward from the rear end of main section 368. Extending forward from main section 366, push rod 366 is formed to have a head 372. Head 372 is cylindrical and has an outer diameter less than that of main section 368. Rod head 372 is formed with a hole 374 that extends axially therethrough.

The push rod 366 is mounted to the attachment 366 so that the head 362 of the intermediate drive shaft seats in rod slot 370. Rod head 372 seats in the bore 218 formed in the tail section 216 of the output drive shaft 214. A pin 376 extends through collet sleeve holes 258, outer drive shaft grooves 220 and rod hole 374. A bearing assembly 234 that extends between rod main section 368 and the inner wall of head tube 330 rotatably couples the push rod in the head tube. It will further be observed that a sleeve 378 extends around the rear end of the push rod 366.

An actuator 382 mounted in the housing neck 328 selectively, longitudinally displaces the push rod 366. Actuator 382 has the same general shape as the first-described actuator 130. However, actuator 382 is both smaller in diameter and length than actuator 130. Actuator 382 is normally positioned around the front end of the main body 360 of intermediate drive shaft 356. The actuator 382 is oriented so that the end of the actuator with the inwardly directed lip faces the push rod 366. Housing neck 328 is formed with opposed slots 384 in which ball bearings are seated. The ends of ball bearings 385 seat in the indentations formed in the actuator 382.

A collar 386 is rotatably fitted over housing neck 328. Collar 386 is similar in shape though smaller in diameter to previously described collar 288. The sections of the ball bearings 385 that extend out of slots 384 seat in the grooves formed along the inner wall of the collar 288, (grooves not identified). Normally, coupling assembly 334 is configured so that the ball bearings 385 are positioned in the ends of the slots 384 located closest to housing shoulder 326.

Head tube 330 has a base 388 with a diameter greater than that of the rest of the tube. Tube base 388 is threadedly secured to the portion of housing neck 328 located forward of collar 386, (threading not illustrated). The head tube base 388 thus holds collar 386 in position over the housing neck 328. Attachment 320 further includes an alignment sleeve 390. Sleeve 390, depicted best in FIGS. 23 and 26, has a rear end 392 with an outer diameter dimensioned to facilitate the snug securement of the sleeve in the open end of housing neck 328. The sleeve 390 also has a front end 394. The outer diameter of sleeve front end 394 is dimensioned so, when the head tube 330 is fitted over the end 394 to secure the tube to housing 322, the tube tightly fits against the sleeve 390. Sleeve 390 is also provided with a lip 395 that extends outwardly away from the outer surface of the sleeve. Lip 396 is located between the rear and front ends of the sleeve 392 and 394, respectively. When the sleeve 390 is mated to the housing 322, lip 396 limits the extent to which the sleeve is inserted in the neck bore 329.

A spring 398 extends between the rear face of the input drive shaft 214 and push rod 366. More specifically, the rear end of spring 398 seats against the annular shoulder of push rod 366 located between its main section 368 and the head 372. Spring 398 displaces the push rod 366 rearwardly so that push rod holds the collet sleeve 240 against the collet ankles 248. Thus, spring 98 latches the collet sleeve 240 so that the sleeve holds the collet feet 246 in the run position. A spring 402 extends between the rear end of the alignment sleeve 390 and the adjacent forward-directed face of actuator 382. Spring 402 urges actuator 382 away from the adjacent ends of push rod 366 and sleeve 378.

It will further be observed that additional bearing assemblies 234 are fitted in the head tube 330 forward of output drive shaft 214. Bearing assemblies 234 provide a rotating interface between the accessory shaft main body 152 and the adjacent inner wall of the head tube 330. Sleeves 294, 295 and 297 hold the bearing assemblies 234 apart from each other. A nose cap 146 is fitted into the open end of the head tube 330.

Attachment 320 is used in a manner similar to that in which attachment 170 is used. The rotational movement applied to the input drive shaft 336 from the handpiece motor 34 is transferred through the intermediate drive shaft 356 and the push rod 366 to the output drive shaft 214. Owing to the latching of the collet feet 246 in the drive shaft bore 228, the collet 238 transfers the rotational movement of the output drive shaft 214 to the cutting accessory 40 against which the feet abut.

Coupling assembly 334 of this version of the invention is moved from the run state to the accessory load state by the rotation of collar 386. The rotation of collar 386 causes ball bearings 385 to be displaced in the forward direction in the housings slots 384. The movement of the ball bearings 385 causes a like forward movement of the actuator 382. As a result of the forward movement, actuator 382 eventually strikes and displaces sleeve 378. The forward translation of sleeve 378 causes a like movement of the push rod 366. The displacement of the push rod 366 causes the forward movement of the collet sleeve 240 that results in the coupling assembly being placed in the accessory load position.

The attachment 320 of the system 30 of this invention provides an alternative means for the surgeon to apply the accessory head 42 to a surgical site. Head tube 330 of attachment 320 has the same narrow cross-sectional width of previously described head tube 174. Accordingly, the extent to which head tube 330 obstructs the field-of-view of the surgical site is minimized. Moreover, the outer diameter of the housing shoulder and neck sections 326 and 328, respectively, is likewise minimized. Specifically in some preferred versions of the invention the maximum diameter of the housing shoulder and neck sections 326 and 328, respectively, including collar 386, is 0.750 inches or less. In more preferred versions of the invention, the maximum diameter of these components is 0.400 inches or less. In still more preferred versions of the invention, the maximum diameter of these components is 0.350 inches or less. An advantage of these components having this relatively narrow diameter is that it means the extent to which the forward portions of the attachment 320, which contain the coupling assembly 334, obstruct the field-of-view of the surgical site is likewise minimized.

Figure 27:
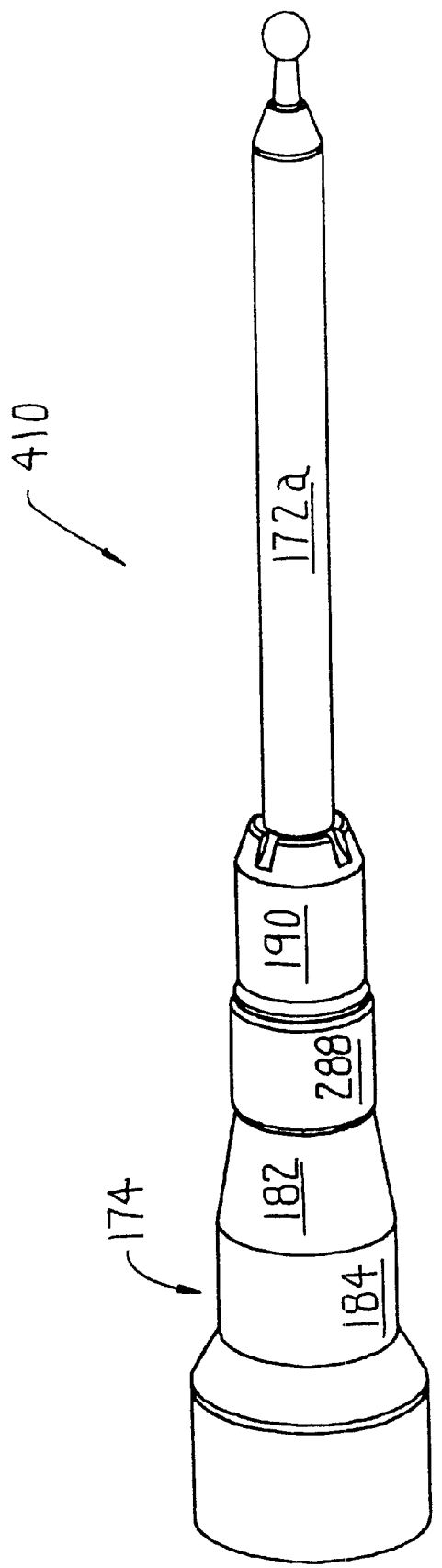
FIG. 27 is a perspective view of another attachment of this invention.
Figure 28:
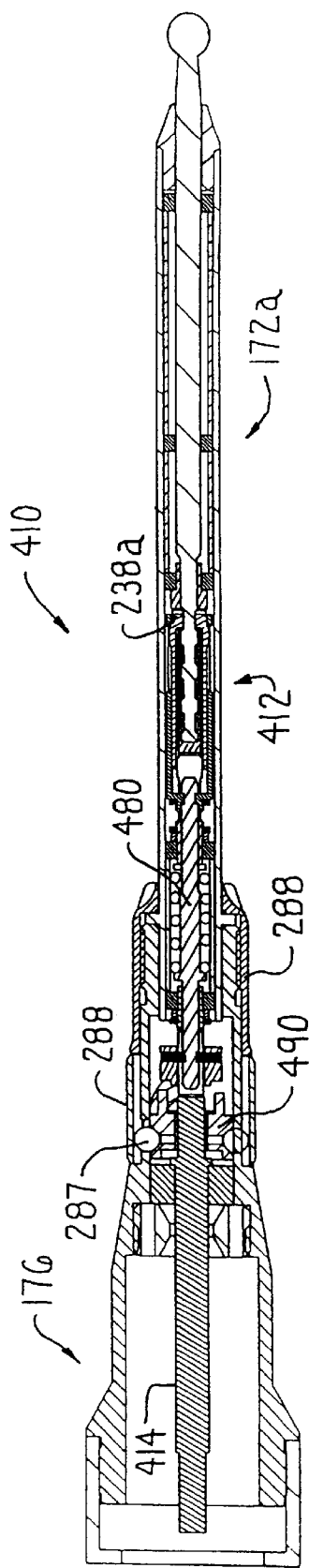
FIG. 28 is a cross-sectional view of the attachment of FIG. 27.
Figure 29:
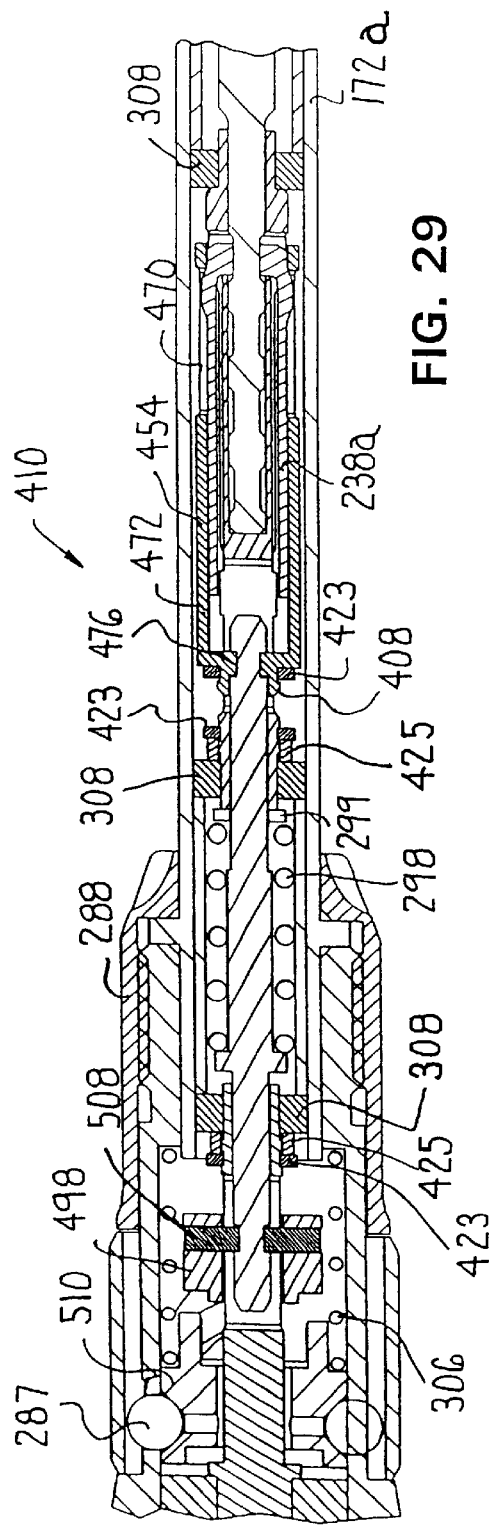
FIG. 29 is an enlarged cross-sectional view of the attachment of FIG. 29.

FIGS. 27–29 depict another attachment 410 of the system 30 of this invention. Attachment 410 is a medium length attachment that is used to position the cutting accessory 40 in situations in which attachment 36 is too short and attachment 170 is too long. Attachment 410 includes the previously described housing 174. A head tube 172*a*, which is a shortened version of head tube 172, extends outwardly from the front of housing 174. A coupling assembly 412 is located in the head tube 172*a* and housing 174 for rotatably and releasably holding the accessory shaft 44 in the head tube.

Attachment 410 has an input drive shaft 412 depicted in FIGS. 30A and 30B. Drive shaft 414 has the main body 194, the stem section 196 and annular lip 198 of previously described input drive shaft 192. Forward of annular lip 198, input drive shaft 414 is shaped to have a neck 416 that has a diameter less than that of the main body 194. A head 418, which has a diameter less than that of the neck 416, extends forward of the neck.

The input drive shaft 414 is shaped to have a bore 420 that extends from the front end of the head 418, through the head into the front of the neck 416. A rectangular-shaped opening 422 extends diametrically through the neck 416. The rear end of bore 420 is in communication with the front end of opening 422. The input drive shaft 414 is further formed to have an annular groove 424 that is located immediately behind the front end of neck 416. Specifically, groove 424 is located between the front end of neck 416 and slots 422.

Input drive shaft 414 is rotatably fitted in housing 174 in the same manner in which drive shaft 192 is fitted in the housing. Shaft head 418 extends into the open rear end of head tube 172*a*. A bearing assembly 308 rotatably holds the shaft head 418 in the head tube 172*a*. A retention clip 423 holds bearing assembly 308 in position. The retention clip 423 is seated in the groove 426 formed in the front of the shaft neck 416. A small spacer ring 425 is fitted around the shaft neck and head 416 and 418, respectively. Spacer ring 425 holds the bearing assembly 308 away from retention clip 423.

An output drive shaft 426, now described by reference to FIGS. 31 and 31A, is rotatably fitted in head tube 172*a*. The output drive shaft 426 includes a tail section 428 that has a first diameter. An intermediate section 430 that has a diameter greater than that of the tail section 428 extends forward from the tail section. The output drive shaft 426 also has a main section 432 that is located forward of the intermediate section 430. Main section 432 has a diameter that is greater than that of the tail section 430. A head 434, that has a diameter approximately equal to that of the intermediate section 430, extends forward from the main section 432.

The output drive shaft 426 has a circular bore 436 that extends forward from the rearwardly directed face of tail section 428. Bore 436 extends through the tail section 428 and into intermediate section 430. Output drive shaft 426 also has a rectangularly shaped opening 438 that is located immediately forward of bore 436. The output drive shaft 426 is formed so that opening 438 is located in the intermediate section 430. Immediately rearward of opening 438, the output drive shaft 426 so as to have an annular groove 440 that extends circumferentially around the outer surface of the shaft intermediate section 430.

A bore 442 extends axially rearwardly through the output drive shaft 426 through the head 434 and partially through the main section 432. Bore 442 is sized and shaped to receive accessory shaft stem 154. Slots 444 are formed in diametrically opposed sections of the outer surface of the shaft intermediate and stem sections 430 and 432, respectively. Slots 444 are not in communication with bore 442. A through channel 446 extends diametrically through the shaft main section 432. Through channel 448 is contiguous with the front ends of slots 444 and intersects bore 442.

From FIG. 29 it can be seen how output drive shaft 426 is rotatably held in head tube 172*a*. A bearing assembly 308 is fitted over the shaft head 434 to provide a first rotatable coupling between the shaft 426 and the head tube 172*a*. A second bearing assembly 308 is fitted over the shaft tail section 428. The second bearing assembly 308 likewise providing a low friction interface between the shaft 426 and the head tube 172*a* so as to allow the shaft to rotate relative to the head tube. A retention clip 423 is snap fitted in the annular interstitial space in output drive shaft groove 440. Retention clip 423 prevents the bearing assembly 308 disposed around the shaft tail section 428 from moving in the forward direction. A spacer ring 425 disposed around the tail section 428 holds the bearing assembly 308 away from the retention clip 423.

A collet 238*a* and collet sleeve 454 that form part of the coupling assembly 412 are fitted over the output drive shaft 426. As seen in FIG. 31, collet 238*a* has a base 246, legs 244 and feet 246 geometrically similar to the like features of collet 238. Collet 238*a* is further formed to have a small ankle 458 between the end of each leg 244 and the associated foot 246. Each ankle 453 is shaped to have a first beveled surface 460 that extends diagonally outwardly and forwardly away from the outer surface of the associated leg 238. The ankle 458 has a flat surface 462 that extends forward from the first beveled surface 460. Collectively, the flat surfaces 462 of ankles 458 are parallel with each other. Each ankle 458 also has a second beveled surface 464. Beveled surfaces 464 extend forwardly and inwardly relative to the flat surfaces 462 with which the second beveled surfaces 464 are contiguous. The outer surface of each collet foot 246, it will be noted, is aligned with the outer surfaces of the leg 244 with which the foot is associated.

Collet sleeve 454 is shaped to have a generally cylindrical body 468. Body 468 is formed to define two diametrically opposed generally rectangularly shaped windows 470. The collet sleeve 454 has two diametrically opposed legs 472 that extend rearwardly from the rear end of body 468. An inwardly directed foot 474 is located at the end of each leg 472. Feet 474 are each shaped to have a foot pad 476 that is the most inwardly located portion of the foot. Each foot 474 also has a toe 478 that is located rearwardly of the foot pad 476 and extends outwardly relative to the adjacent foot pad.

FIG. 32 illustrates a push rod 480 that is integral with coupling assembly 412. Push rod 480 includes a tail 482. While the tail 482 has a generally circular cross sectional profile, it has an end section with opposed flat surfaces 481. The tail 482 is further formed so that there are opposed indentations 484 in the arcuate side surfaces of the tail that extend between the flat surfaces 481. Extending forward from tail 482, the push rod 480 has a main body 486 with a generally cylindrical profile. The main body 486 has an outer diameter greater than that of the tail 482. A flange 488 extends circumferentially and outwardly around the interface between the push rod tail 482 and the main body 486.

Extending forward from the front end of main body 486, the push rod 480 is formed to have a cylindrical neck 490. Neck 490 has an outer diameter slightly less than that of main body 486. The push rod 480 has a head 492 that extends forward from neck 490. Head 492 has a generally rectangular profile and is coaxial with the rod tail 482, main body 486 and neck 490. The side surfaces of head 492 are, however, curved and flush with the outer surface of neck 490. Two diametrically opposed indentations 494 are formed in the side surfaces of head 492.

Push rod 480 is rotatably mounted in head tube 172a. The end section of the push rod tail 482 is seated in opening 422 formed in the input drive shaft 414. More particularly, the input drive shaft 414 and the push rod 480 are shaped so that tail 482 is not able to rotate relative to the opening 422 but the tail is able to longitudinally slide in the opening.

Figure 33:
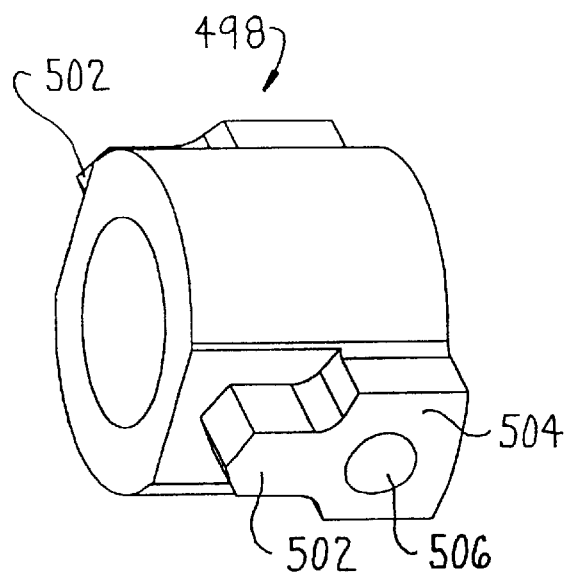
FIG. 33 is a perspective view of the pusher ring of the attachment of FIG. 27.

A pusher ring 498, depicted in FIG. 33, is fitted around the outside of the input drive shaft neck 416. Pusher ring 498 is generally tubularly shaped and is dimensioned so as to be slideable over the drive shaft neck 416. The pusher ring 498 is formed so that on the outer surface of the ring there are two rearwardly directed teeth 502. Each tooth 502 has a base 504 with a bore 506 that extends inwardly towards the center of the pusher ring 498. The rearward-directed end of each tooth 502 is pointed. Pins 508, seen in FIG. 29, are press fit into the ring bores 506. The inner ends of pins 508 seat in indentations 484 formed in input drive shaft tail 482. Owing to the abutment of pins 508 against tail 482, the push rod 480 and pusher ring 498 engage in like rotational and translating motion.

Figure 34:
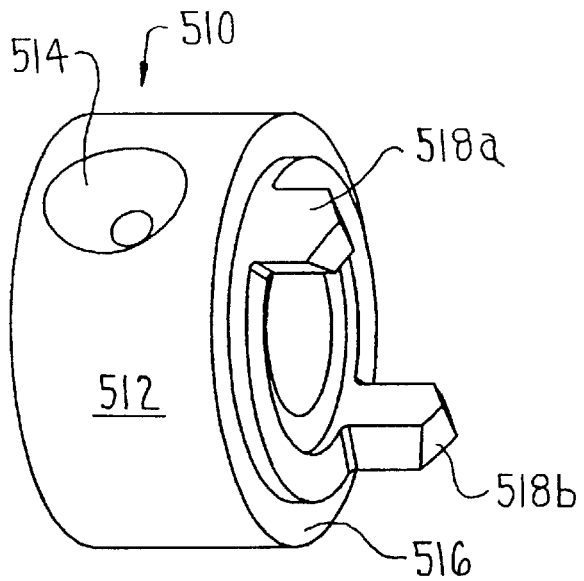
FIG. 34 is a perspective view of the actuator of the attachment of FIG. 27.

An actuator 510, seen in FIG. 34, forces the push ring 498 forward so as to cause a like motion in the push rod 480. Actuator 510 includes a main body 512 that is generally ring-shaped. The actuator is positioned so that the main body 512 extends around the portion of the input drive shaft 410 located forward of lip 198. The outer surface of actuator main body 512 is formed with indentations 514 in which ball bearings 287 (FIG. 28) are seated. The front annular face of main body 512 is formed to have an annular rib 516 that extends forward from the main body. Rib 516 is located between the inner and outer perimeters of the main body 512. Two teeth 518a and 518b extend forward from rib 516. Teeth 518a and 518b are diametrically opposed from each other. Both teeth are provided with pointed front faces. While the teeth are generally identical in shape, tooth 518b is, however, longer than tooth 518a.

As in the previously described versions of the invention, ball bearings 287 seat in slots 286 formed in housing 174. The rotation of collar 288 fitted over housing 174 results in the forward and rotational movement of the ball bearings 287. The displacement of the ball bearings 287 results in the like displacement of the actuator 510.

Returning to FIG. 29, it can be seen that the push rod head 492 is seated in opening 438 of the output drive shaft 426. The body 468 of collet sleeve 454 is seated over the collet 238a. The legs 472 of sleeve 454 extend rearwardly relative to the collet 238a. The sleeve feet 474 extend into the opposed ends of opening 438 formed in the output drive shaft 426. The foot pads 476 of the sleeve feet 474 seat in the indentations 494 formed in the push rod head 492. A retention clip 423 holds the sleeve feet seated immediately forward of the sleeve to the push rod 480. The retention clip 423 extends around the sleeve feet 474 immediately forward of the associated toes 478.

Spring 298 extends between the output drive shaft 426 and push rod 480. More particularly, the spring 298 extends between a washer 299 disposed around the push rod 480 that abuts the shaft tail section 428 and the forward facing surface of the rod flange 488. Spring 298 displaces the push rod 480 rearwardly so that the push rod holds the collet sleeve 454 in the run state. A spring 306 extends between the inwardly directed annular step 308 formed in the housing 174 and the actuator 510. Spring 306 prevents unintended forward movement of the actuator that could result in the inadvertent transition of the coupling assembly 412 from the run state to the accessory load state.

Figure 35:
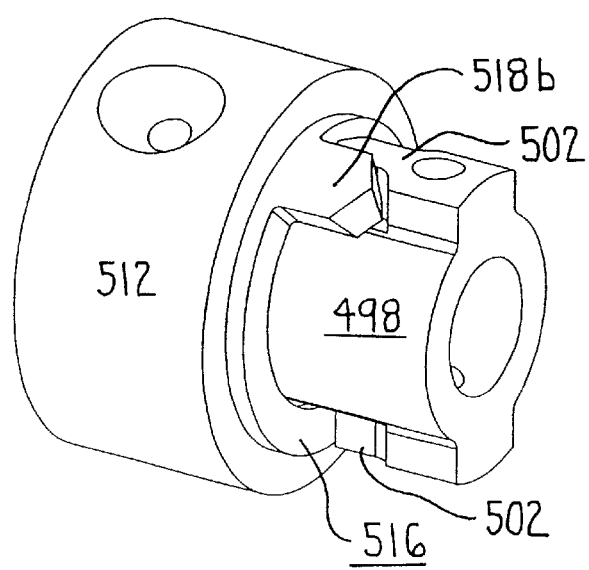
FIG. 35 is a perspective view illustrating how the pusher ring of FIG. 33 and the actuator of FIG. 34 mate.
Figure 36:
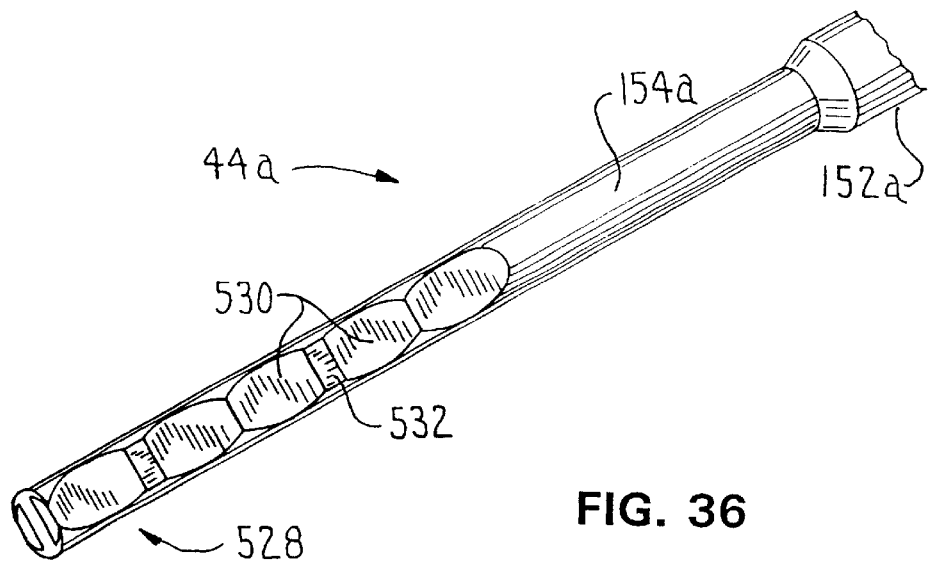
FIG. 36 is a perspective view of the proximal end of an alternative shaft of the cutting accessory of this invention.

FIG. 35 illustrates how the actuator 510 works against the pusher ring 498 to force the forward displacement of the pusher ring and push rod 480. Eventually, as result of the forward and rotational displacement of the actuator 510, rib 516 of the actuator abuts teeth 502 of the pusher ring 498. The continued forward displacement of the actuator 510 results in the like motion of the pusher ring 498 and the push rod 480.

The forward movement of the push rod 480 causes like translational motion of the collet sleeve 454. As a result of the forward movement of the sleeve 454, the windows 470 formed in the sleeve come into registration over the collet feet 246. Thus, when the coupling assembly 412 is in this state, the accessory load state, the feet 246 are free to flex out of the output drive shaft bore 442 to allow the insertion, removal or adjustment of the accessory shaft stem 154 fitted in the bore.

One advantage of the coupling assembly 412 of this version of the invention is that the interfaces between the input drive shaft 414 and the push rod 480, between the push rod and the output drive shaft 426 and between the push rod and the collet sleeve 454 are accomplished without the need for providing through holes through the push rod. Thus, this coupling assembly is designed in such a way that the structural features of the push rod 480 do not appreciably weaken the mechanical strength of the push rod.

Still another feature of coupling assembly 412 is that when the assembly is in the accessory load state, teeth 502 of the pusher ring 498 abut teeth 518a and 518b of the actuator 510. At this time, it should be understood, that the actuator 510 is locked in a static state. Owing to the engagement of teeth 450 against teeth 518a and 518b, the pusher ring 498, and therefore the push rod 480, are blocked from rotation. Thus, the coupling assembly 412 of this invention prevents the rotation of the drive shafts 414 and 426 when the assembly is in the accessory load state. Since the drive shafts 414 and 426 are unable to rotate, this assembly 412 likewise is designed to prevent an accessory 40 seated in the output drive shaft 426 from being rotated when the assembly is in the accessory load state.

Another feature of coupling assembly 412 is that actuator teeth 518a and 518b are of unequal size. Normally, when the actuator 510 is moved forwardly, the tips of teeth 518a and 518b will strike diametrically opposed surfaces of the adjacent teeth 502. However, due to manufacturing tolerances, there is a remote possibility that the tips of teeth 518a and 518b could strike adjacent beveled surfaces of the opposed teeth 502. If teeth 518a and 518b were to strike these surfaces simultaneously, the actuator 510 would be locked out from further forward motion relative to the pusher ring 498. The actuator 510 would be prevented from driving the rest of the coupling assembly 412 into the release. However, since tooth 518b is longer than tooth 518a, tooth 518b is the first tooth to strike the beveled surface of an adjacent tooth 502. The continued forward movement of the tooth 518b causes sufficient rotational movement of the pusher ring 498 to ensure that tooth 518a then strike a beveled surface of the complementary pusher ring tooth 502 that is diametrically opposed to the surface against which tooth 518b abuts. Thus, this feature of assembly 412 prevents the assembly of inadvertently being locked out from being displaced into the accessory load state.

It should also be understood that the same set of cutting accessories 40 that have shafts 44 of a common length that are used with attachment 36 may be used with attachments 170, 320 and 410. This feature of the system 30 of this invention further minimizes the number of different types of accessories 40 that need to be provided.

FIGS. 36–39 depict an alternative shaft 44a of the cutting accessory 40 of this invention. Shaft 44a includes the previously described main body 152 that extends rearwardly from attachment head 42. A stem 154a extends coaxially rearwardly from main body 152. The section of the stem 154a adjacent the main body 152 has a circular cross sectional profile that has a diameter less than the diameter of the main body 152.

The section of the stem 154a distal from the main body 152, section 528, is shaped to have the retention features of the shaft 44a. More particularly, section 528 of the stem 154a is shaped so as to have a plurality of diametrically opposed concave faces 530 that extend inwardly from the outer surface of the section of the stem. adjacent the main body. The faces 530 are in two sets. In each set, the faces are longitudinally aligned and longitudinally spaced apart from each other.

Figure 38:
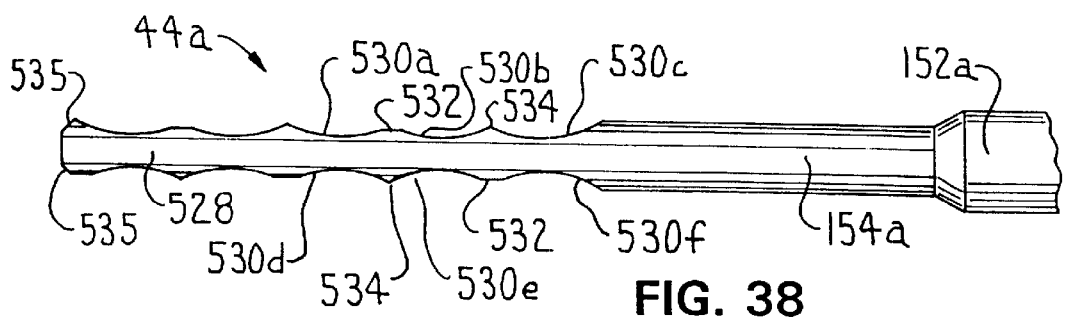
FIG. 38 is a plan view of the shaft of FIG. 36 wherein one the side surface of the shaft between the diametrically opposed surfaces that form face surfaces is seen in plan view.
Figure 39:
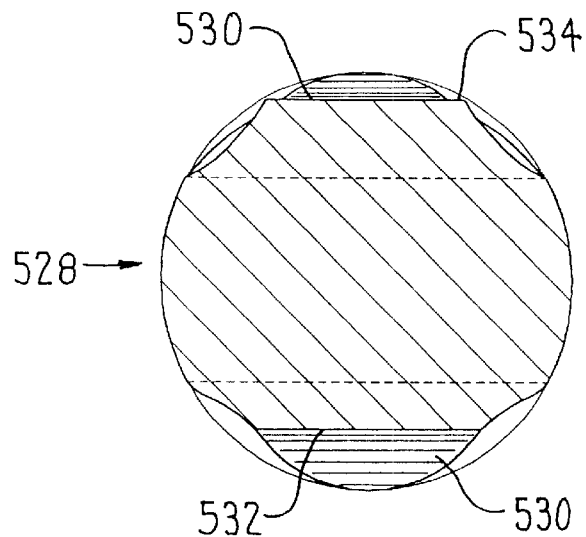
FIG. 39 is a cross sectional view taken along line 39—39 of FIG. 37.

It will be observed that shaft section 528 is formed so the slices of the section where diametrically opposed adjacent pairs of faces 530 meet are asymmetrically formed relative to the longitudinal axis of the shaft 44a. For example, in the depicted embodiment of the invention, as seen in FIG. 38, the slice of the shaft section where the two faces 530a and 530b in the top of the drawing closest to main body 152 is formed to have a flat surface 532. Opposite flat surface 532, the portion of section 528 that forms faces 530d and 530e, the faces diametrically opposite faces 530a and 530b, respectively, is shaped to define a line-shaped crest 534. Crest 534, as best seen in FIG. 39, projects further away from the longitudinal axis of stem 154a than the distance flat 532 extends from the same axis. The crest 534 can be considered to be formed by the ends of adjacent faces 530d and 530e.

Extending distally along stem 154a, it will be seen that between the second and third top-located faces, faces 530b and 530c, section 528 is formed to have a crest 534. Diametrically opposite this crest 534, in the slice space between downwardly directed faces 530e and 530f, there is a flat 532. Thus, on one side of section 528 the slices between the faces are shaped to have an alternating flat-crest-flat-crest pattern; on the opposite side of the section the slices are shaped to have an alternative crest-flat-crest-flat pattern.

Figure 37:
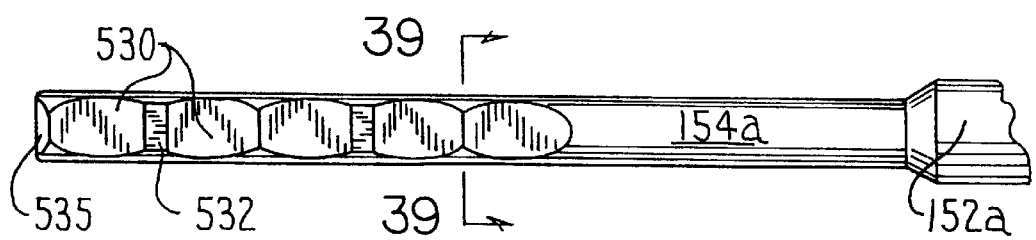
FIG. 37 is a plan view of the shaft of FIG. 36 wherein the faces on one side of the shaft are seen in plan view.

It will further be observed from FIGS. 37 and 38 that the proximal end tip of stem 154a is formed to have two symmetrically opposed beveled surfaces 535. Each surface 535 is in line with a separate one of the sets of the linearly arranged faces 530. Surfaces 535 function as tapered surfaces that allow the proximal end of the stem 154 to be slip fitted between the collet feet 541, FIG. 40, internal to the handpiece 32 with which the accessory of this invention is used.

Figure 40:
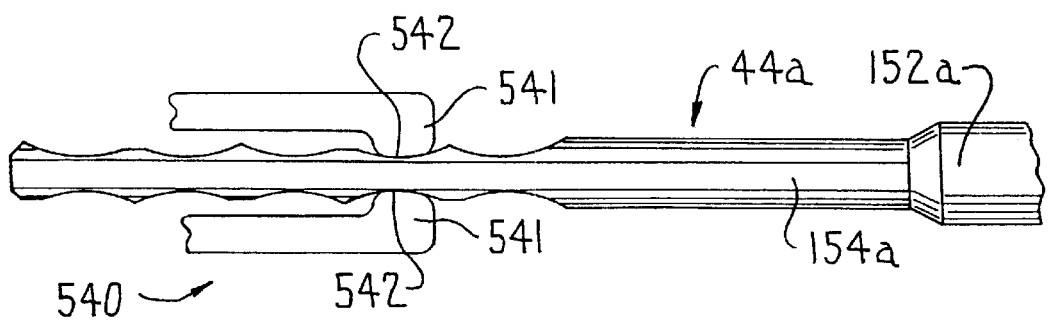
FIG. 40 is a side view depicting how a collet holds the shaft of FIG. 36 to a surgical handpiece.

As seen by reference to FIG. 40, a generic collet 540 of the coupling assembly in which shaft 44a is inserted is shaped to have feet 541 with opposed toe surfaces 542 that face each other. More particularly, the collet is shaped so that the toe surfaces 542 have a radius of curvature equal to the radius of curvature of the faces 530 that form the retention features of the shaft 44a. When the collet feet 541 are pressed against the shaft section 528, and the collet toe surfaces 542 are seated in opposed faces 530, the collet feet clamp the shaft 44a to the collet so that the collet and shaft will rotate in unison.

Figure 41:
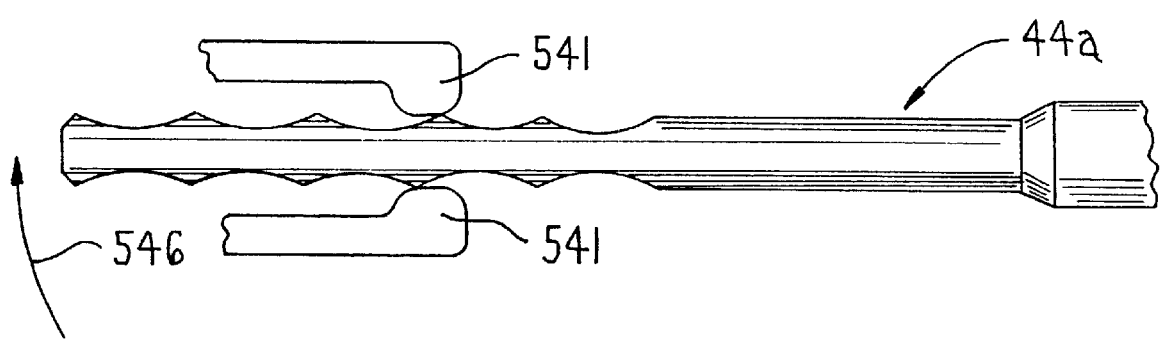
FIG. 41 is a side view illustrating how, due to manufacturing tolerances a cutting accessory can possibly bind the feet of the collet employed to hold the accessory in place. In this Figure, the offset in alignment of the retention features is exaggerated for purposes of illustration.

The reasons why slices of shaft section 528 are asymmetric formed is best understood by reference to FIGS. 40 and 41. Statistically, most often when the collet feet 541 pressed against stem section 528, the toe surfaces 542 strike the curved surfaces of a pair of diametrically opposed faces 530. The continued urging of the collet feet 541 together causes a minor longitudinal displacement of the shaft 44a. This displacement occurs until the collet toe surfaces 542 are pressed against the shallowest sections, the troughs, of the opposed faces 530.

However, due to manufacturing tolerances, if the cutting accessory is formed to have opposed crests 534, these crests may not be precisely aligned. In some instances, as illustrated in FIG. 41, when the collet feet 541 are moved together, depending on the position of the toe surface 542 relative to the crests, the feet could bind the accessory shaft. Once the shaft is so caught, the collet feet 541 are no longer able to displace, auto-align, the shaft so that the toe surfaces seat in the troughs of one of the pairs of faces 530.

Figure 42:
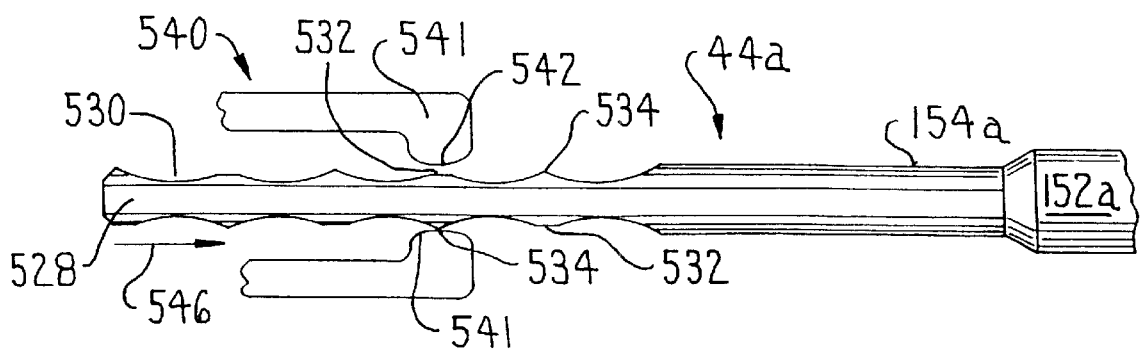
FIG. 42 is a side view depicting how the shaft of FIG. 36 engages the feet of the complementary collet so as to avoid the binding illustrated in FIG. 41.

The provision of the asymmetrically shaped sections between adjacent pair of longitudinally spaced apart faces 530 in the shaft of this invention substantially eliminates the likelihood that the above event can occur. With shaft 44a, when collet feet 541 move towards a section between the faces 530, the toe surface 542 of one foot strikes the adjacent shaft crest 534 before the opposed toe surface strikes the complementary flat 532. As a result of the one collet foot 541 striking the crest 534 without an opposing contact occurring, the shaft is longitudinally displaced as represented by curved arrow 546 in FIG. 42. This longitudinal displacement of the shaft 44a longituinally aligns the shaft with the collet 540 so that the collet feet 541 will then bear against diametrically opposed shaft faces 530. Thus, the asymmetric shaping of the shaft 44a facilitates the longitudinal auto-alignment of the shaft with the coupling assembly in which the shaft is inserted.

Still another feature of shaft 44a, is that there are no large constant diameter sections between adjacent retention features. Consequently there is no likelihood that the grasping members of a coupling assembly could inadvertently hold one of these inter-retention feature sections and give a false feel to surgical personnel that the shaft is clamped in place when, in fact, it is not so securely held.

It should be recognized that the above-described version of the shaft may vary from what has been described. For example, in the described version, the retention features are diametrically opposed faces that are circumferentially spaced apart from each other. In other versions of the invention the retention features may circumferentially abut each other.

Also, in other versions of the invention, on each section of the shaft 44a on which the retention features are formed there may be more than the two retention features shown in the illustrated embodiment of the invention. Similarly, in some versions of the invention, the retention features may comprise a single set of longitudinally linearly aligned faces that extend down the length of one arcuate portion of the shaft stem. It should likewise be recognized that, in the auto alignment process, depending on the position of the shaft 44a relative to the collet 540, there may be situations in which as the collet feet press against the shaft, the shaft is displaced in a direction opposite the direction depicted in FIG. 42.

Similarly, it should be recognized that the surface geometry of the disclosed retention features is understood to be exemplary, not limiting. For instance it may be desirable to form some retention features so that their surfaces have both curved and planar sections or wholly planar sections. For example, in some versions of the invention, each retention feature may be a pair of angled faces formed in the shaft stem. Collectively, the set of linearly arranged retention features would have a sawtooth pattern.

Also, the lateral sections located between the longitudinally spaced apart retention features may have different cross-sectional geometries that what has been illustrated. In some versions of the invention, it may not even be necessary to provide the shaft stem with the asymmetrically shaped sections between adjacent retention features.

Similarly, in some versions of the invention, it may be desirable to form the proximal end of the stem 154a so that it has a geometry different than the opposed beveled surfaces 535. For example, it may be desirable to form this portion of the cutting accessory so that it has a frusto-conical shape. The inclined surface of this section would provide the same functional result as the beveled surface 535.

It should be understood that the foregoing description is directed to specific versions of the surgical tool system 30 of this invention. Other versions of the invention may differ from what has been described. For example, it may not always be necessary to form input drive shaft 336 out of two components as has been described. It should, of course, be understood that the ball bearing slots 286 and 384 associated with attachments 170 and 320, respectively, are typically formed with tails so that coupling assemblies 176 and 334 can be locked in the accessory load state. However, in some versions of the invention, the coupling assemblies may not be provided with means to be locked in the accessory load state.

Moreover, the components forming the individually described coupling assemblies 38, 176, 334 and 412 nay be interchanged with each other as necessary.

Figure 44:
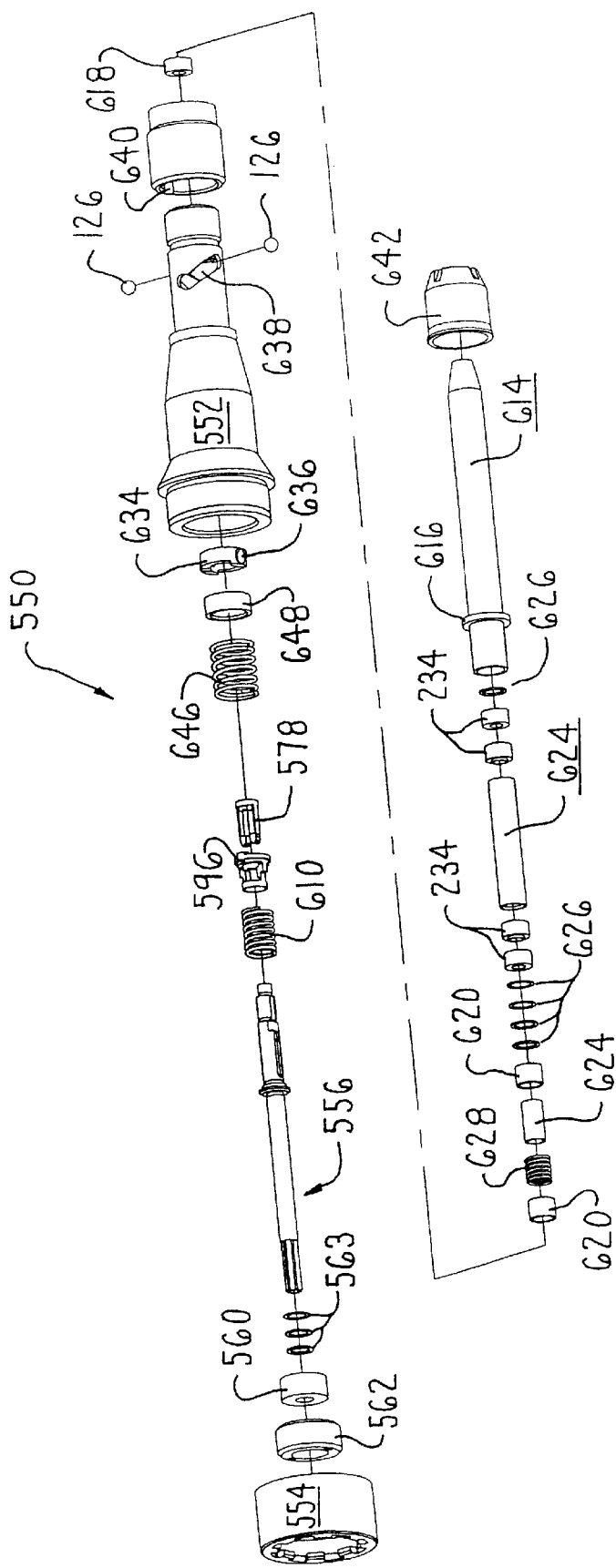
FIG. 44 is an exploded view of the attachment of FIG. 43.

FIGS. 43 and 44 illustrate an alternative removable attachment 550 of this invention. Attachment 550 includes a housing 552 and base 554 similar, if not identical to previously described housing 48 and base 56. A drive shaft 556 is rotatably fitted in housing 552 with a bearing assembly 560. A bearing retainer 562 holds the bearing assembly 560 in the counter bore in which the assembly is seated. One or more shim washers 563 may be fitted between the proximal end of bearing assembly 560 and the adjacent surface of the housing 552 to account for manufacturing tolerances.

Figure 45:
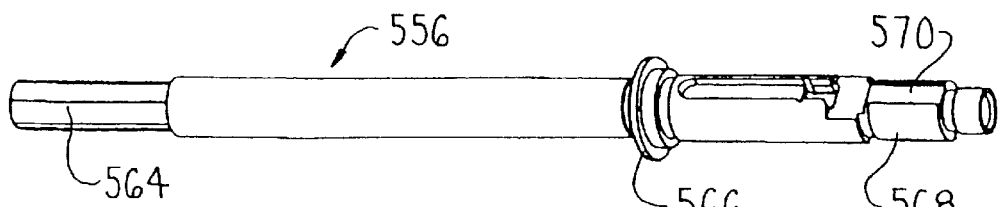
FIG. 45 is a perspective view of the drive shaft internal to the attachment of FIG. 43.
Figure 46:
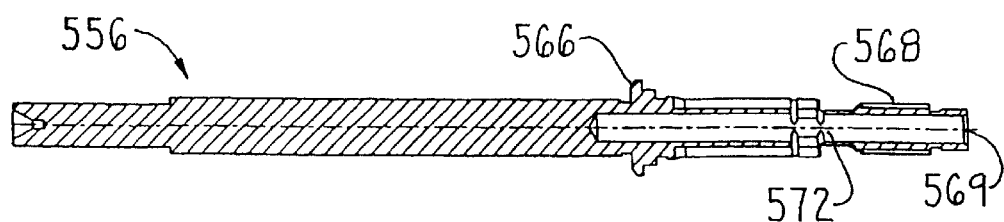
FIG. 46 is a cross sectional view of the drive shaft of FIG. 45.

Drive shaft 556, seen best in FIGS. 45 and 46, has a proximal end 564 with a hex shaped cross sectional profile for the purposes previously described. Extending forward from the main cylindrical portion of the driver shaft, it is observed that the drive shaft is formed to have a circumferentially extending flange 566. The distal end of the drive shaft 556 is formed to have a round head 568 that has a reduced outer diameter relative to the ruin body of the drive shaft.

A constant diameter bore 569 extends axially through the drive shaft 556 from the distal front end of the head 568 to a position slightly rearward of flange 566. The distal end of the main body of the drive shaft 556, the portion located immediately rearward of head 568, is formed to have two diametrically opposed slots 570. Slots 570 are each defined by a flat base and parallel side walls that extend perpendicularly upwards from the base. Drive shaft 556 is further formed to have a laterally extending channel 572 that extends between the slots 570. Channel 572, it will be understood, also intersects bore 569.

Figure 47:
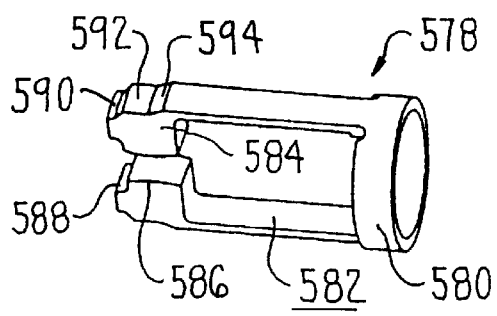
FIG. 47 is a perspective view of the collet internal to the attachment of FIG. 43.

A collet 578, seen best in FIG. 47, is fitted over the drive shaft 556. Collet has a ring-shaped base 580. When attachment 550 is assembled, the collet 578 is positioned so that base 580 is fitted over the portion of the main body of the drive shaft 556 immediately distal to the head 568. Two diametrically opposed legs 582 extend rearwardly from the base 580. Each leg 582 is seated in a separate one of the slots 570. A foot 584 extends inwardly from the free end of each leg 582. Each foot 584 seats in a separate end of channel 572. Each foot 584 has a toe surface with a main section 586 that has a convex profile. More particularly, the curvature of the toe surface main section matches that of the faces 530 of the complementary shaft 44a. Extending distally from main section 586, the toe surface is shaped to form a notch 588 that has a curved profile. The toe surfaces of feet 584 are seated in the opposed ends of channel 572.

The outer surface of each foot 564 is shaped to have an ankle. A first part of the ankle, at the distal end of the associated foot 564, is a curved notch 590. Extending proximally, towards collet base 580, the ankle has a main surface 592 that forms the outer surface of the foot 564. This ankle main surface is located inwardly of the outer surface of the associated collet leg 582. Between the main surface 592 and the collet leg 582, the ankle has a beveled surface 594 that is transition surface between the main surface 592 and the leg 582.

Figure 48:
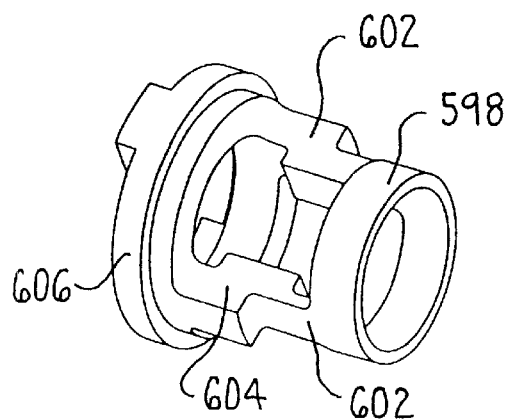
FIG. 48 is a perspective view of the collet sleeve internal to the attachment of FIG. 43.

A collet sleeve 596 is slidably fitted over the drive shaft 556 adjacent the collet feet 584. The collet sleeve, as seen in FIG. 48, has a circular base 598. Two diametrically opposed webs 602 extend proximally forward from the base 598. Each web 602 is formed to have a rectangular tab 604 that extends inwardly towards the center axis of the sleeve 596. Each web 602 terminates at a head ring 606. The inner diameters of sleeve base 598 and head ring 602 are identical. Head ring 606 has an outer diameter that is greater than the outer diameter of the base 598. Collet sleeve 596 is fitted to the drive shaft so that tabs 604 seat in the portions of slots 570 that are located proximal to channel 572.

A coil spring 610 pushes the collet sleeve 596 in the forward direction, towards collet feet 584. Spring 610 seats against the drive shaft flange 556. The proximal end of the spring 610 seats against a laterally extend circumferential step surface of the collet sleeve between webs 602 and head ring 606.

Extending forward from housing 552, attachment 550 has a nose tube 614. The nose tube 614 has an outer surface that is generally cylindrical. Nose tube 614 is, however, formed to have an annular flange 616 that is located forward of the distal end of the tube. When the attachment 550 is assembled, the portion of the nose tube 614 distal to flange 616 seats in the housing 552. Flange 616 seats against the proximal end of the housing 552. More particularly, nose tube 614 is dimensioned so that the distal end of the tube extends over the drive shaft head 568 and the adjacent portion of the main body of the drive shaft over which the collet base 580 is seated. The inner diameter of the nose tube 614, it is understood, is greater than the outer diameter of the drive shaft 556. A bearing assembly 618 provides a low-friction interface between the drive shaft head and the adjacent inner surface of the nose tube 614.

Inside nose tube 614, forward of bearing assembly 618 are a pair of preload rings 620. The preload rings are held apart by a tube-shaped preload spacer 622. Forward of the most proximal preload rings 620 are four bearing assemblies 234. A tube-shaped bearing spacer 624 is positioned between the second and third bearing assemblies 234. Shims 626 are located adjacent some of the bearing assemblies 234. It should also be recognized that there might be some variations in the individual bearing assemblies 234. For example, when two bearing assemblies 234 are adjacent, one of the bearing assemblies may have an inner race that is slightly longer in length than the complementary outer race. This component selection is to ensure proper loading of the bearing assemblies and the other components and/or to prevent contact between opposed races adjacent bearing assemblies.

A coil spring 628 extends around preload spacer 622. Spring 628 biases the distal preload ring 620 and the components forward that preload ring in the forward direction. Movement of these components internal to the nose tube 614 is stopped by the abutment of the forward most bearing assembly 234 against an annular step internal to the nose tube 614.

A rotating collar 632 and an actuator 634 cooperate to selectively displace urge the collet sleeve 586 rearwardly away from the collet feet 584. Actuator 634 is generally ring shaped and extends around the collet legs 582 and the adjacent portion of the drive shaft 556. Actuator 634 is formed with diametrically opposed indentations 636 designed to accommodate complementary ball bearings 126. The ball bearings 126 extend through slots 638 formed in the housing 556 that are similar to slots 124 of housing 48.

Collar 632 is rotatably fitted over the portion of the housing 552 in which slots 638 are formed. The collar is formed with opposed grooves 640 that have an arcuate cross section profile. When the collar is fit over housing, the sections of ball bearings 126 that extend beyond slots 638 seat in grooves 640. A collar ring 642 is threaded secured to the section of the housing 552 that is forward of collar 632. Collar ring 642 thus releasably holds the collar 632 over the housing 552. The proximal end of collar ring 642 has an inwardly directed annular step 644. When collar ring 642 is secured to the housing 552, step 644 bears against the forward facing surface of nose tube flange 616 so as to hold the nose tube 614 to the housing.

A coil spring 646 acts against actuator 634 to ensure that the actuator 634 is normally spaced from the collet sleeve 596. One end of spring 646 bears against the outer race of bearing assembly 560, race not identified. The opposed end of spring 646 bears against the proximal end of a spacer ring 648. The distal end of spacer ring 648 bears against actuator 634.

In the absence of external force, spring 646 and spacer ring 648 cooperate to hold actuator 634 away from collet sleeve 596. When the coupling assembly of attachment 550 is in this state, spring 610 pushes the collet sleeve 596 in the forward direction. As a result of this positioning of the collet sleeve 596, the portions of the sleeve webs 602 forward of the tabs 604 bear against the collet ankle main surfaces 592. The forward movement of the collet sleeve 596 is stopped by the abutment of the sleeve tabs 604 against the bottom, rearwardly facing surfaces of the collet feet 584. When the coupling assembly is in this state, the accessory run state, movement of the collet toe sections out of drive shaft bore 569 is blocked. Thus, the collet feet 584 will bear against the opposed faces 530 of the cutting accessory shaft 44a seated in the bore 569. This action ensures that the cutting accessory shaft 44a will rotate in unison with the rotation of the drive shaft.

The coupling assembly is displaced from the accessory run state to the accessory load state by the manual rotation of collar 632. This movement causes the helical displacement of ball bearings 126 in slots 638. The longitudinal rearward displacement of the ball bearings 126 results in a like displacement of actuator 634. As a result of the movement of the actuator 634 to the distal end of the attachment 550, the distal end face of the actuator abuts the adjacent proximal end face of the collet sleeve 596. The continued movement of the actuator 634 results in the actuator overcoming the force of spring 610 and moving the spring distally, away from the collet feet 582. Thus, when the coupling assembly is in this state collet feet 582 are free to flex outwardly away from shaft bore 569. Thus, when the coupling assembly is in this state the stem 154a of the cutting accessory can be removed from the shaft bore 569, inserted into the shaft bore, or its position selectively set in the shaft bore.

Figure 49:
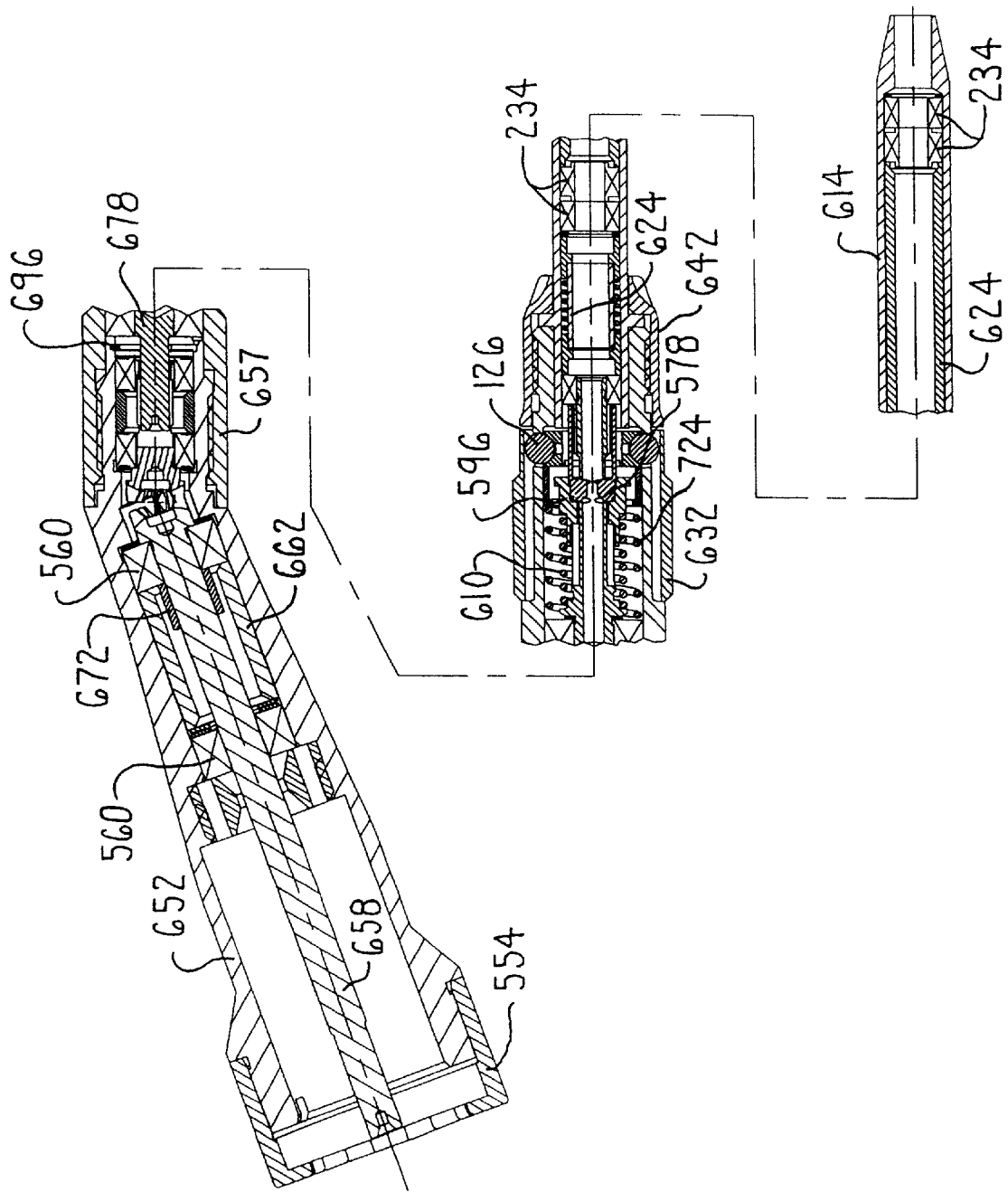
FIG. 49 is a multi-section cross sectional view of an alternative angled attachment.
Figure 50:
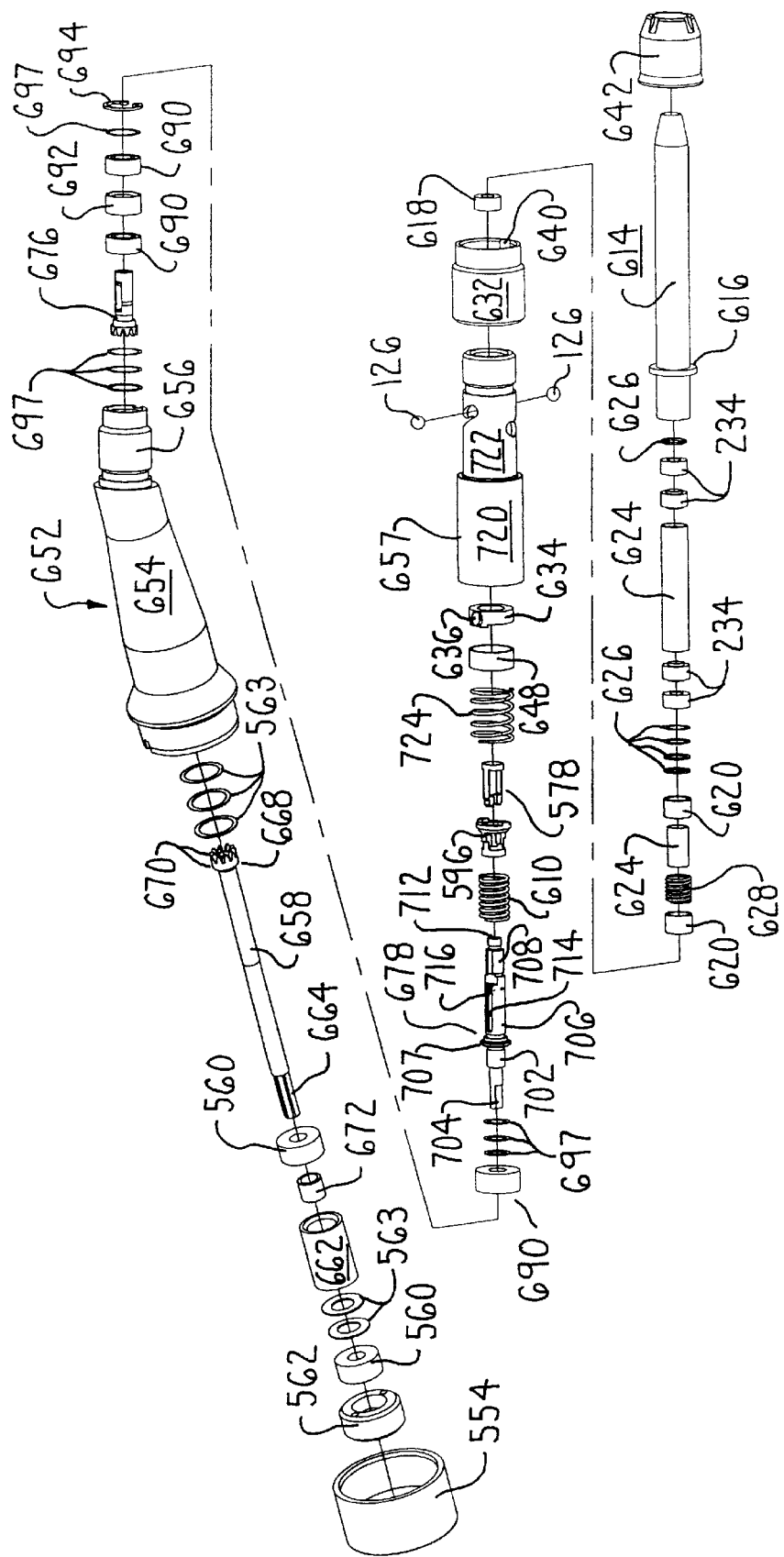
FIG. 50 is an exploded view of the attachment of FIG. 49.
Figure 52:
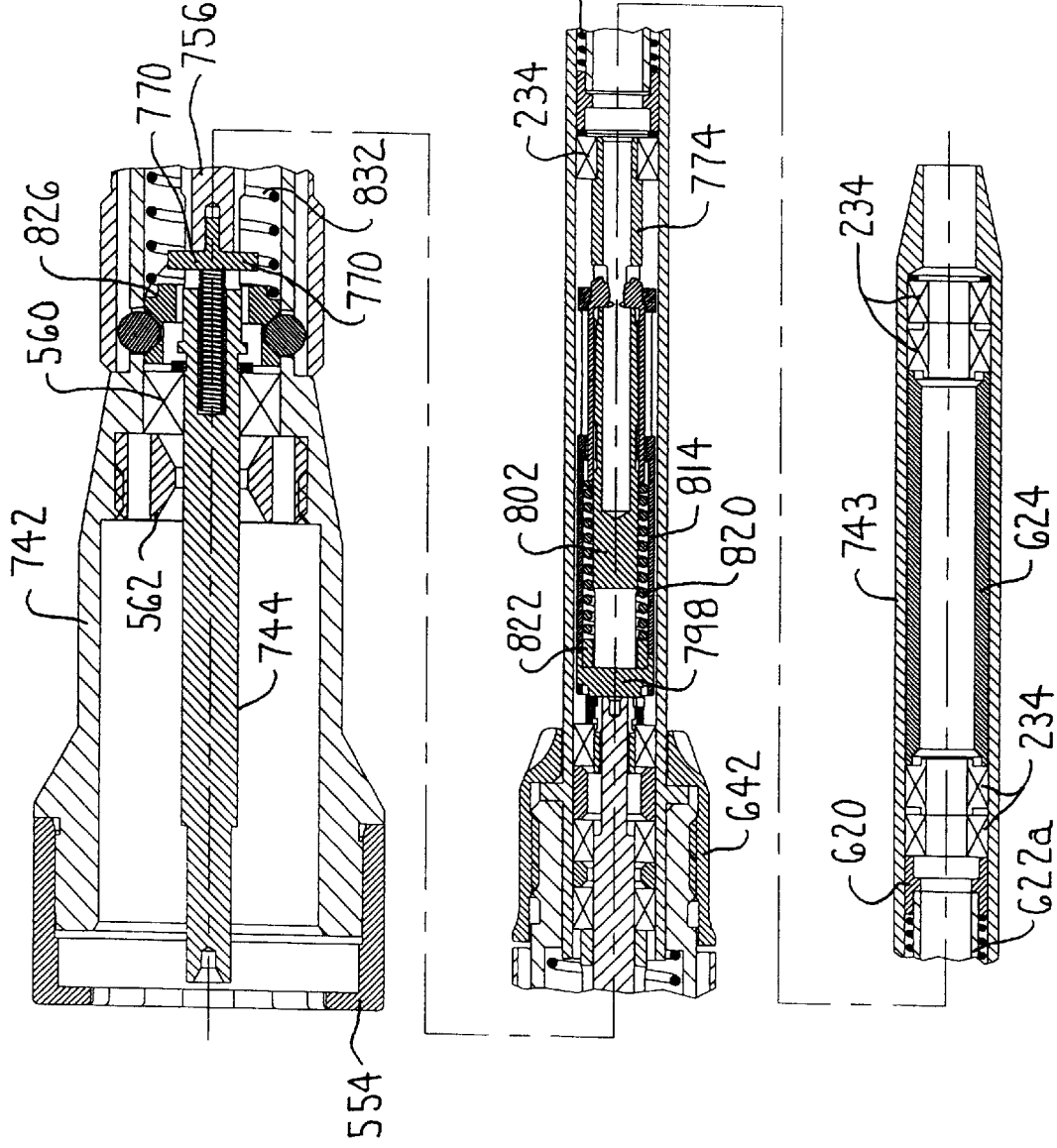
FIG. 52 is a multi-section cross sectional view of an alternative straight long attachment of this invention.

An alternative angled attachment 650 of this invention is now described by initial reference to FIGS. 49 and 50. Angled attachment 650 includes base 554 to which an angle housing 652 is attached. Angle housing 652 has a main body 654 that is coaxial with base 554. Forward from main body 654, angle housing 652 is shaped to have a constant diameter neck 656. Neck 656 is axially offset from main body by angle between 15 and 450. Attachment 650 also has an elongated generally cylindrical front housing 657. The distal end of front housing 557 extends over and is threadedly secured to the outer surface of angle housing neck 656. Front housing 657 thus extends coaxially forward from neck 656.

An input drive shaft 658 is rotatably mounted in angle housing main body 654. Two bearing assemblies 560 rotatably hold the input drive shaft to the angle housing 652. A proximal one of the two bearing assemblies 560 is seated in the base of a counterbore 660 formed in the main body 654. A distal one of the bearing assemblies 560 extends between the drive shaft 658 and the wall at the distal end of the counterbore 660. A tube-shaped spacer 662 holds the bearing assemblies 560 apart from each other. Bearing retainer 562 holds the bearing assemblies 560 and the spacer in the angle housing 652. Shims 563 may be located between the distal bearing assembly 560 and the surface of housing 652 against which the assembly seats.

The input drive shaft 658 is formed with a proximal end 664 that has a hex-shaped profile. Input drive shaft 658 also has a large diameter head 668 that is located forward of the distal bearing assembly 560. Head 668 is formed with gear teeth 670 that extend axially forward. In order to prevent longitudinal movement of drive shaft 658, a tube-shaped lock ring 672 is press fit over the shaft 658. More particularly, lock ring 672 is positioned to bear against the inner race of the proximal most bearing assembly 560. Lock ring 672 thus prevents unwanted forward movement of the input drive shaft.

Figure 51:
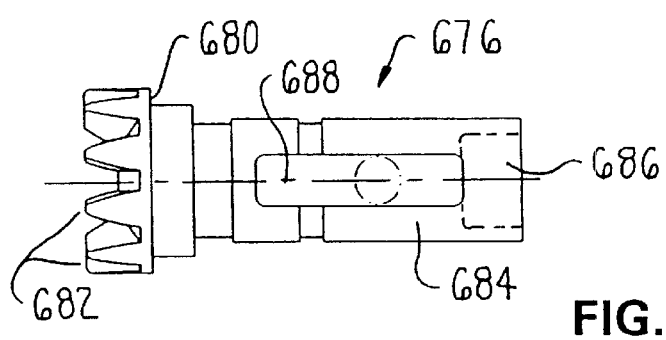
FIG. 51 is a plan view of the transfer gear internal to the attachment of FIG. 49.

A transfer gear 676 and an output drive shaft 678 are rotatably fitted to the angle housing neck 656 to transfer the rotational moment applied to the input drive shaft 658 to the cutting accessory 40 fitted to attachment 650. The transfer gear 676, seen in FIG. 51, has a large diameter base 680. Base 680 has rearwardly extending teeth 682. Transfer gear teeth 682 engage input drive shaft teeth 670 so the rotation of the drive shaft 658 results in the like movement of transfer gear 676. Transfer gear 676 is further formed to have a reduced diameter stem 684 that extends axially forward of base 680. The stem 684 is formed to have an axially extending circular bore 686, shown in phantom, that extends rearwardly from its proximal end. Located distal to and contiguous with bore 686, an axially extending rectangular bore 688 is formed in stem. For manufacturing reasons, in the depicted version of the invention bore 688 is seen as a rectangular slot that extends through opposed sides of the stem.

Two spaced apart bearing assemblies 690 rotatably hold transfer gear 676 in angle housing neck 656. Both bearing assemblies 690 extend between the transfer gear stem 684 and the adjacent inner wall of the neck 656. A first bearing assembly 690 has an inner race, not illustrated, that seats against a shoulder surface between base 680 and stem 684. A second bearing 690 assembly is fitted around the proximal end of stem 684. A tube-shaped spacer 692 holds the bearing assemblies 690 apart. A C-shaped retaining ring 694 holds the transfer gear 676, the bearing assemblies 690 and spacer 692 in neck 656. More particularly, retaining ring 694 is snap fitted in a groove 696 formed in the inner wall of neck 656. One or more shims 697 may be provided between bearing assemblies 690 and the members adjacent the bearing assemblies 690.

The output drive shaft 678 is formed to have a tail 702 of relatively small diameter. The proximal end of the tail 702, which is the proximal end of the outer drive shaft 678, has two diametrically opposed flats 704. More particularly, the proximal end of the tail is formed to be press fit into bore 688 of transfer gear 676 so that the drive shaft 678 and transfer gear are essentially a single unit. Extending forward from tail 702, output drive shaft 678 has a main body 706. A circular flange 707 extends around the outer surface of the main body 706 a small distance forward of tail 702. A reduced diameter shoulder section 708 is located forward of the main body 706. A head 710, with a diameter less than that of shoulder section 708, forms the proximal end of the output drive shaft 678.

A bore 712 extends axially rearwardly from head 710. Opposed slots 714 are formed in the shaft main body 706 and shoulder sections 708. A channel 716 extends laterally through the main body. Bore 712, slots 714, and channel 716 are geometrically similar to bore 569, slots 570 and channel 572 of previously-described drive shaft 556.

Collet 578 is fitted over the proximal end of output drive shaft 678. Collet feet 584 thus seat in the opposed ends of channel 716. Collet sleeve 596 is slidably fitted over the shaft main body 706 rearwardly of the collet feet 584. Spring 610 extends between shaft flange 707 and the collet sleeve 596.

Front housing 657 it should be understood has a main section 720 and a shoulder section 722 that is coaxial with the main section 720. Main section 720 is the portion of the front housing 657 that is threadedly secured to angled housing neck 656. Front housing shoulder section 722 encases the forward portion of the output drive shaft 678, collet 578, collet sleeve 596 and spring 610.

Nose tube 614 extends forward from the proximal end of front housing shoulder section 722. Nose tube flange 616 seats against an adjacent proximal end surface of the front housing shoulder section 722. Previously described preload rings 620, preload spacer 622, spring 628, bearing assemblies 234, bearing spacer 624 and shims 626 are fitted in the nose tube 614.

Collar 632 is fitted over the front housing 657 and actuator 634 is disposed in the front housing in order to selectively displace collet sleeve 596. Actuator 634 is fitted around the portion of the output drive shaft 678 over which the collet legs 582 are seated. A spring 724 and spacer ring 648 are provided in order to ensure that actuator 634 is normally spaced away from collet sleeve 596. Spring 724 extends between the outer race of the proximal bearing assembly 690, outer race not illustrated, and spacer ring 648.

Collar 632 is rotatably fitted to the front housing shoulder section 722. Ball bearings 126 transfer the rotational movement of the collar 632 to the actuator 634. In order for the collar's movement to be transferred to the actuator as helical movement, the ball bearings 126 extend through slot 726 formed in the housing shoulder section 722. Slots 726 are similar in shape to slots 638.

Collar ring 642 is threaded to the proximal end of the front housing 722 to secure the nose tube 614 and collar 632 to the front housing 722.

The coupling assembly internal to attachment 650 works in the same general manner as the coupling assembly internal to attachment 550. Collet sleeve 596 normally presses against collet feet 584. This interaction holds the collet feet 584 in bore 712 of the output drive shaft 678. Thus, the collet feet 584 hold the associated shaft 44a in the bore 712 so that the cutting accessory shaft 44a rotates in unison with the output drive shaft 678. The rotation of collar 632 results in the longitudinally displacement of the collet sleeve 596 away from the collet feet 584. When the collet sleeve 596 is so positioned, the collet feet 584 are able to flex away from the output drive shaft to allow the removal, insertion or repositioning of the cutting accessory in the drive shaft bore 712.

Owing to its angled configuration, attachment 650 can, in some situations, allow the surgeon to have a less-obstructed view of the surgical site.

Figure 53:
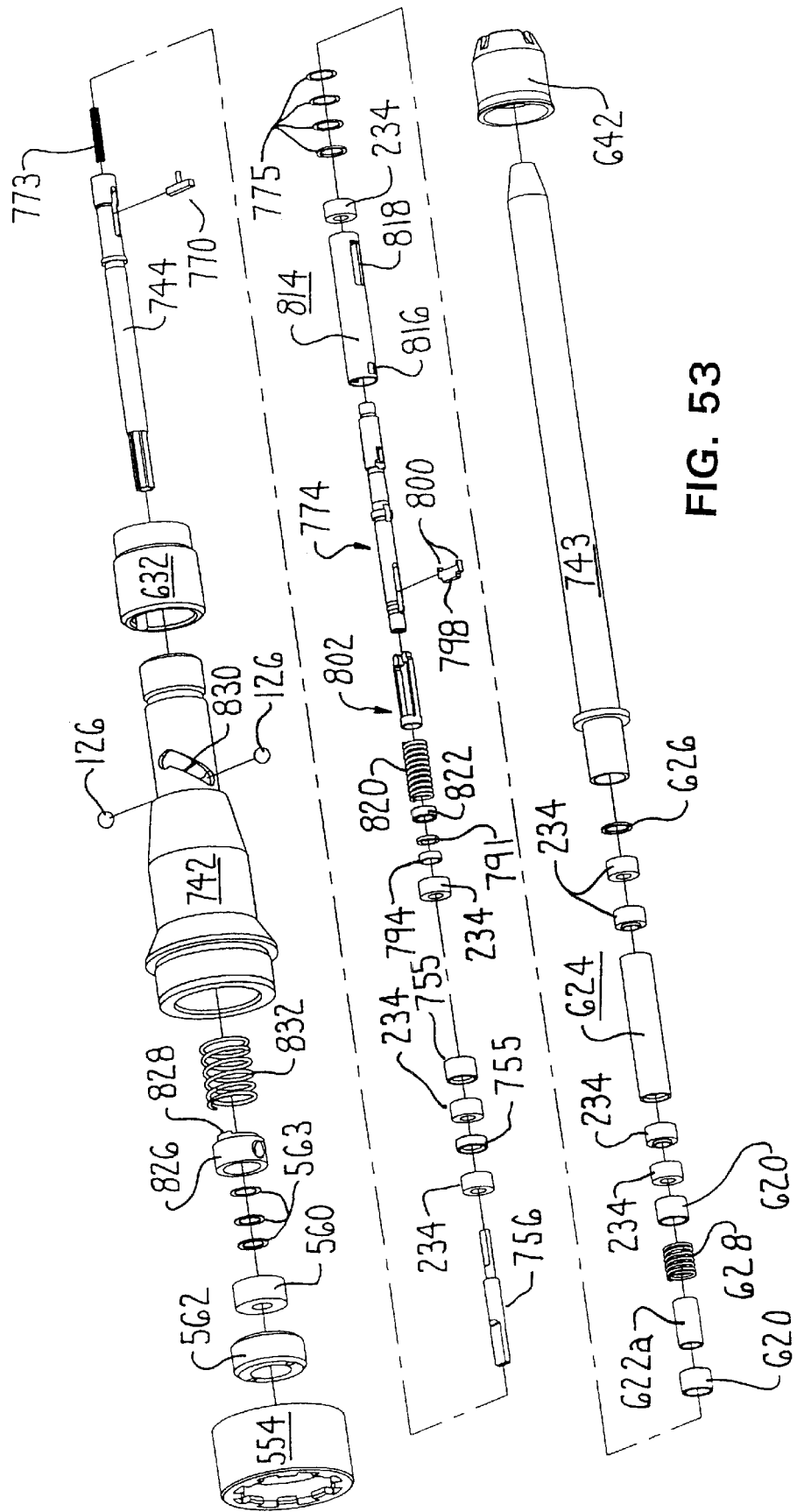
FIG. 53 is an exploded view of the attachment of FIG. 52.
Figure 54:
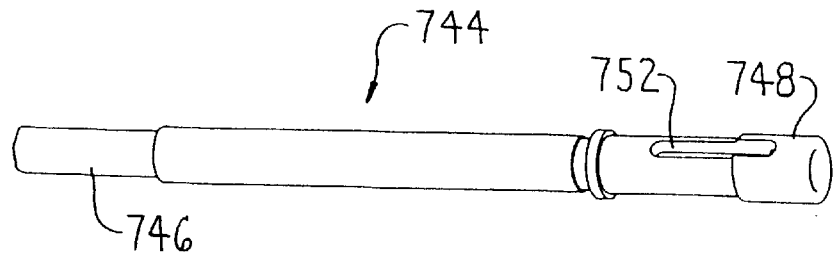
FIG. 54 is a perspective view of the drive shaft internal to FIG. 52.

An alternative long attachment 740 of this invention is now described with initial reference to FIGS. 53 and 54. Long attachment 740 includes a housing 742 to which base 554 is attached Housing 742 is similar to housing 552 except for one significant difference which is discussed below. An elongated nose tube 743 extends forward from the distal end of housing 742. Bearing assembly 560 rotatably holds an input drive shaft 744 in housing 742. Bearing retainer 562 holds bearing assembly 560 in position.

Figure 55:
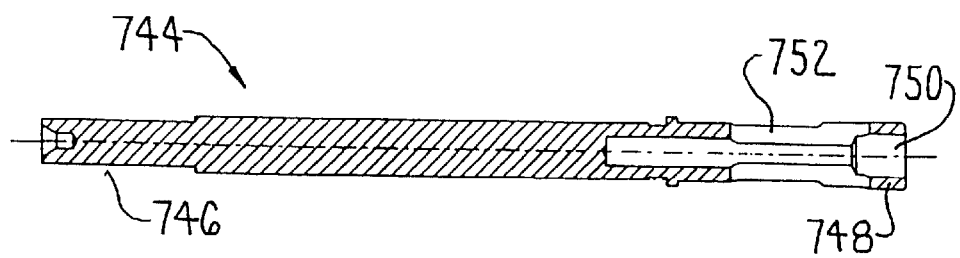
FIG. 55 is a cross sectional view of the drive shaft of FIG. 54.
Figure 56:
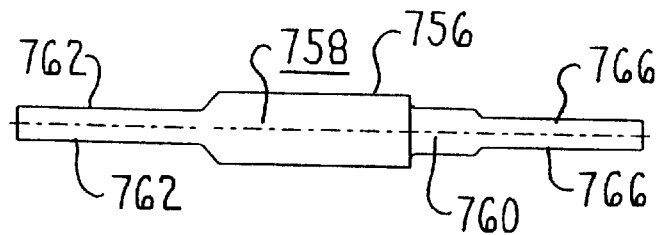
FIG. 56 is a plan view of the push rod internal to the attachment of FIG. 52.

As seen best in FIGS. 54 and 55, input drive shaft 744 includes a proximal end 746 with a hex shaped profile. The distal end of shaft 744 has a head 748 with a relatively large diameter relative to the rest of the shaft. An axially extending bore 750 extends rearwardly from the distal end of the head 748. Input drive shaft 744 is further formed to have an elongated slot 752 that is located a slight distance rearwardly from the distal end of the head. Slot 752 extends laterally through shaft 744 and intersects bore 750.

Figure 57:
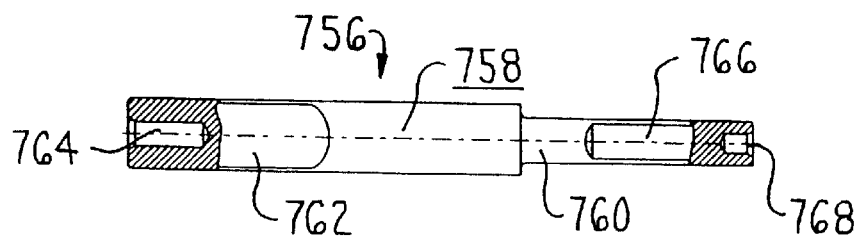
FIG. 57 is a cross sectional view of the push rod of FIG. 56.

A push rod 756 is seated in shaft bore 750. As seen best in FIGS. 57 and 58, push rod 756 is formed to have a cylindrical main body 758 that has a relatively wide diameter. A cylindrical neck 760 of narrow diameter extends coaxially forward of the main body 758. The main body 758 is formed to have two diametrically opposed flats 762. A small bore 764 is formed in the proximal end of the main body. Push rod neck 760 is likewise formed so that the distal end thereof has two opposed flats 766. The planes in which flats 766 are oriented are parallel to the planes in which flats 762 are oriented. A bore 768 extends rearwardly a short distance through the forward facing distal end face of push rod 756.

Shaft bore 750, shaft slot 752 and push rod flats 762 are collectively dimensioned so that the proximal end of the push rod 756 is slidably fitted in the bore 750 and slot 752. Input drive shaft 744 and push rod 756 are further dimensioned so that, when the proximal end of the rod is seated in the drive shaft, the two components engage in like rotation. Bearing assemblies 234 rotatably hold push rod 756 in the proximal end of nose tube 743. A spacer 755 separates the bearing assemblies 234.

Located within the base of shaft bore 750 is a T-pin 770. The longitudinal cross bar of T-pin 770, bar not identified, is dimensioned to extend through and is slidably fitted in the opposed open ends of slot 752. The center post of T-pin 770, post not identified, is securely press fit into proximal end bore 764 of the push rod 756. A small spring 773 is seated in the base of shaft bore 750. Spring 773 pushes against T-pin 772 so as to urge the T-pin and push rod 756 in the forward direction. T-pin 770, as discussed below, is used to affect the longitudinal displacement of the push rod 756.

Figure 58:
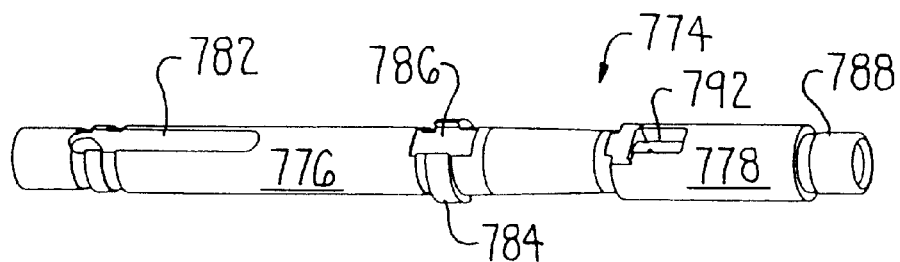
FIG. 58 is a perspective view of the output drive shaft of the attachment of FIG. 52.
Figure 59:
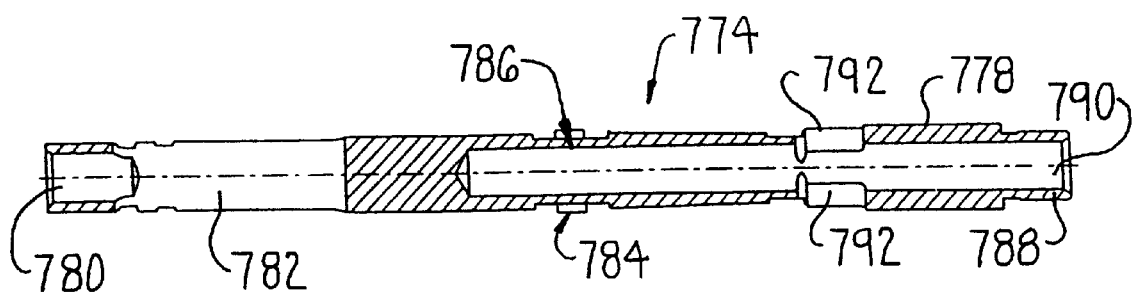
FIG. 59 is a cross sectional view of the drive shaft of FIG. 58.

Push rod 756 rotates an output drive shaft 774 that is rotatably fitted in the nose tube 743. The output drive shaft 774, as seen in FIGS. 58 and 59, has a cylindrical main body 776. A cylindrical head 778, with an outer diameter greater than the diameter of the main body 774 extends axially forward from the main body. The proximal end of the main body 776 has a forwardly extending bore 780. The main body 776 is further formed have an elongated slot 782 that is located forward of bore 780. Bore 780 and slot 782 are contiguous. Located forward of slot 782, the output drive shaft 774 is formed to have An outwardly extending circumferentially extending flange 784. Flange 784 is formed to have two spaced arcuately spaced apart sections so as to define cutout spaces 786 between the flange sections.

The output drive shaft 774 is formed so that its most distal section is a nose 788. The nose 788 is coaxial with and has a smaller outer diameter than head 778. A bore 790 extends axially rearwardly from the front end of the shaft nose 788, through the head and into the distal portion of the main body 776. The proximal end of the shaft head 778 is formed to have diametrically opposed openings 792 adjacent head 778. Openings 792 are contiguous with bore 790.

Bearing assemblies 234 rotatably hold the output drive shaft 774 in nose tube 742. A first bearing assembly 234 is fitted over the proximal end of the drive shaft 774. A ring shaped bearing spacer 794 located immediately forward of the proximal bearing assembly 234 extends around the output drive shaft 774. Spacer 794 prevents the proximal bearing assembly 234 and the output drive shaft 774 from moving relative to each other. A retaining ring 791 holds spacer 794 in place. It will also be observed that there is a spacer 755 located between the bearing assembly 234 associated with the proximal end of the output drive shaft 774 and the adjacent bearing assembly 234 associated with the push rod 756.

The distal bearing assembly 234 extends between the shaft nose 788 and the adjacent inner wall of nose tube 743. Shims 775 separate the distal bearing assembly 234 from an adjacent pre-load ring 620 in the nose tube 743.

When the drive shaft 774 is seated in the nose tube 743, push rod neck 760 is seated in shaft bore 780 and slot 782. Push rod 756 and output drive shaft 774 are collectively dimensioned so that the two components will rotate in unison and the push rod is able to move longitudinally within the shaft bore 780 and slot 782.

A cross pin 798 is seated in shaft bore 780. The cross pin 798 rests on the distal end surface of the push rod neck 760.

The cross pin 798 is dimensioned so that its opposed ends extend out of shaft slot 782. Cross pin 798 is further formed so at each end there is a forward facing finger 800.

Figure 60:
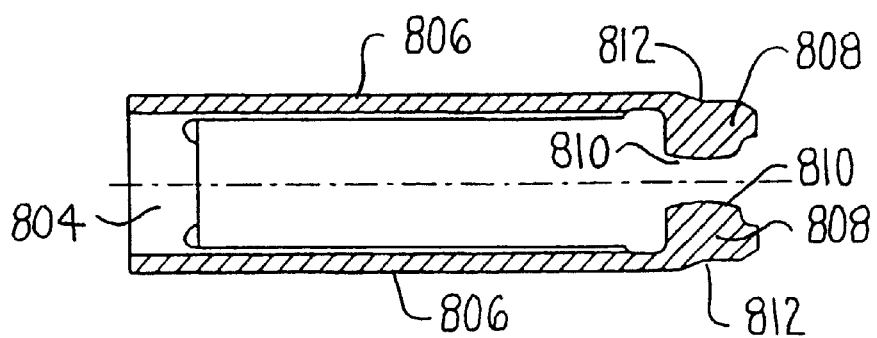
FIG. 60 is a cross sectional view of the collet internal to the attachment of FIG. 52.

A collet 802 is fitted around the output drive shaft 774. The collet 802, now described by reference to FIG. 60, includes a circular base 804 from which two diametrically opposed legs 806 extends. A foot 808 extends inwardly from each leg 806. Each foot 808 has a toe surface 810 located proximal to the longitudinal axis of the collet 802 and an ankle 812 distal from the axis. Collet feet 808 toe surfaces 810 and ankles 812 have the same surface geometry as the toe and ankle surfaces of collet feet 584.

Collet 802 is fitted around the output drive shaft 774 so that base 804 abuts the rearwardly facing face of flange 784. The collet legs 806 extend in the forward direction so that the legs extend through spaces 786. Collet feet 808 thus seat in shaft openings 792. When the collet feet 808 are so seated, the toe surfaces 810 are located within shaft bore 790.

Figure 61:
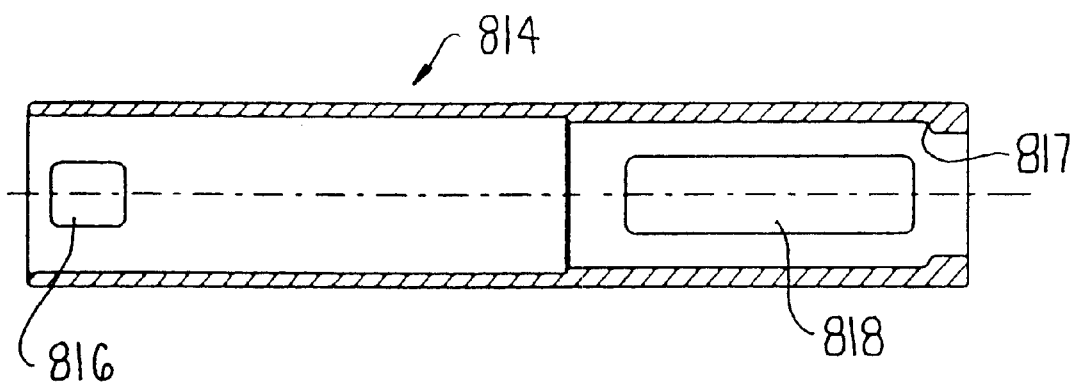
FIG. 61 is a cross sectional view of the collet sleeve internal to the attachment of FIG. 52.

A tube shaped collet sleeve 814 regulates the ability of the collet feet 808 to flex away from the shaft bore 790. As seen in FIG. 61, the collet sleeve is shaped so that immediately forward of the proximal end there are two diametrically opposed openings 816 that have approximately a rectangular cross sectional profile. Rearward of the distal end of the sleeve 814 there are two diametrically opposed elongated openings 818. Each opening 816 is longitudinally aligned with a separate one of the openings 818. The distal end of the collet sleeve 814 is formed to have an annular lip 817 that extends inwardly towards the longitudinal axis of the sleeve.

The collet sleeve 814 slidably fits over the collet 802 and the output drive shaft 774. More particularly, it will be observed that when attachment 740 is assembled, fingers 800 of cross pin 798 each seat in an opposed one of the openings 816. The cross pin 798 thus transfers the rotational moment of push rod 756 to the collet sleeve 814. The collet sleeve 814 is further aligned so that collet legs 806 and ankles 812 are disposed within sleeve openings 818.

A coil spring 820 located between the collet 802 and the collet sleeve 814 urges the sleeve in the rearward direction. The distal end of spring 820 seats against the rearward facing annular surface of the collet base 804. The proximal end of the spring 820 presses against a pilot ring 822 that is fitted around the outside of the proximal end of the output drive shaft 774. The rearwardly directed face of pilot ring 822 bears against the forward facing portions of the cross pin 798 body that extend beyond the perimeter of the output drive shaft 774.

An actuator 826 disposed inside housing 742 is displaced in order to force like longitudinal displacement of the collet sleeve 814 away from the collet feet 808. Actuator 826 is generally similar to actuator 634. However, actuator 826 is longer in height than actuator 634. Actuator 826 is also formed with a pair of forward facing, diametrically spaced apart teeth 828.

Attachment 740 is also provided with collar 632. The collar 632 is rotatably fitted to a constant diameter section of housing 742. Ball bearings 126 are seated in helical slots 830 formed in the housing. Slots 830 are similar to slots 638. However, slots 638 are designed so that clockwise rotation of collar 632 results in rearward displacement of the ball bearings and actuator 634. Slots 830 are shaped so that the same motion of collar 632 of attachment 740 results in forward displacement of the ball bearings 126 and actuator 826.

A coil spring 832 extends around the proximal end of input drive shaft 744. Spring 832 is seated against an annular step at the base of a counter bore inside housing 742. Spring 832 bears against actuator 826 so that the actuator is normally held away from T-pin 770.

Preload rings 620, spring 628 bearing assemblies 234, bearing spacer 624 and shims 62 are fitted in nose tube 743. A preload spacer 622a, which may be slight longer than preload spacer 622 is located between preload rings 620.

In the absence of external force, spring 820 pushes pilot ring 822 and the cross pin 798 rearwardly. The rearward displacement of the cross pin 798 results in a like motion of push rod 756 and collet sleeve 814. As a result of the rearward displacement of the collet sleeve 814, sleeve lip 817 abuts complementary surfaces in the collet feet ankles 812. This contact holds the collet feet 808 in bore 780 of the output drive shaft 774. Thus, when the collet feet 808 are so locked in position they hold any cutting accessory 40 fitted in the bore to the drive shaft 774 so that the accessory rotates with the drive shaft.

Spring 832 normally holds the actuator 826 away from T-pin 770. Thus spring 832 prevents the actuator from inadvertently contact the T-pin that could, in turn, result in the displacement of the collet sleeve 814.

Collar ring 642 secures collar 632 and nose tube 743 to the housing.

When it is desired to place attachment 740 in the accessory load state, collar 632 is rotated. The rotation of the collar 632 causes the actuator 826 to overcome the force of spring 832 and move in the forward direction. As a result of its forward displacement, actuator 826 eventually strikes the opposed end portions of T-pin 770 that extend beyond the outside of input drive shaft 744.

The continued forward movement of the actuator 826 causes the actuator to force the T-pin 770, and therefore push rod 756, in the forward direction. The forward displacement of the push rod 756 results in the like displacement of cross pin 798. The forward movement of the cross pin 798 causes the collet sleeve 814 to engage in a like longitudinal transition. As result of the longitudinal transition of the collet sleeve 814 relative to the output drive shaft 774, the sleeve windows go into registration with the collet feet 808. When the attachment 740 is in this state, the accessory load state, the collet feet 808 are free to flex out of the bore 790 of the output drive shaft. This makes it possible for an accessory 40 to be removed from, inserted in or adjustably positioned in the output drive shaft 774.

Figure 63:
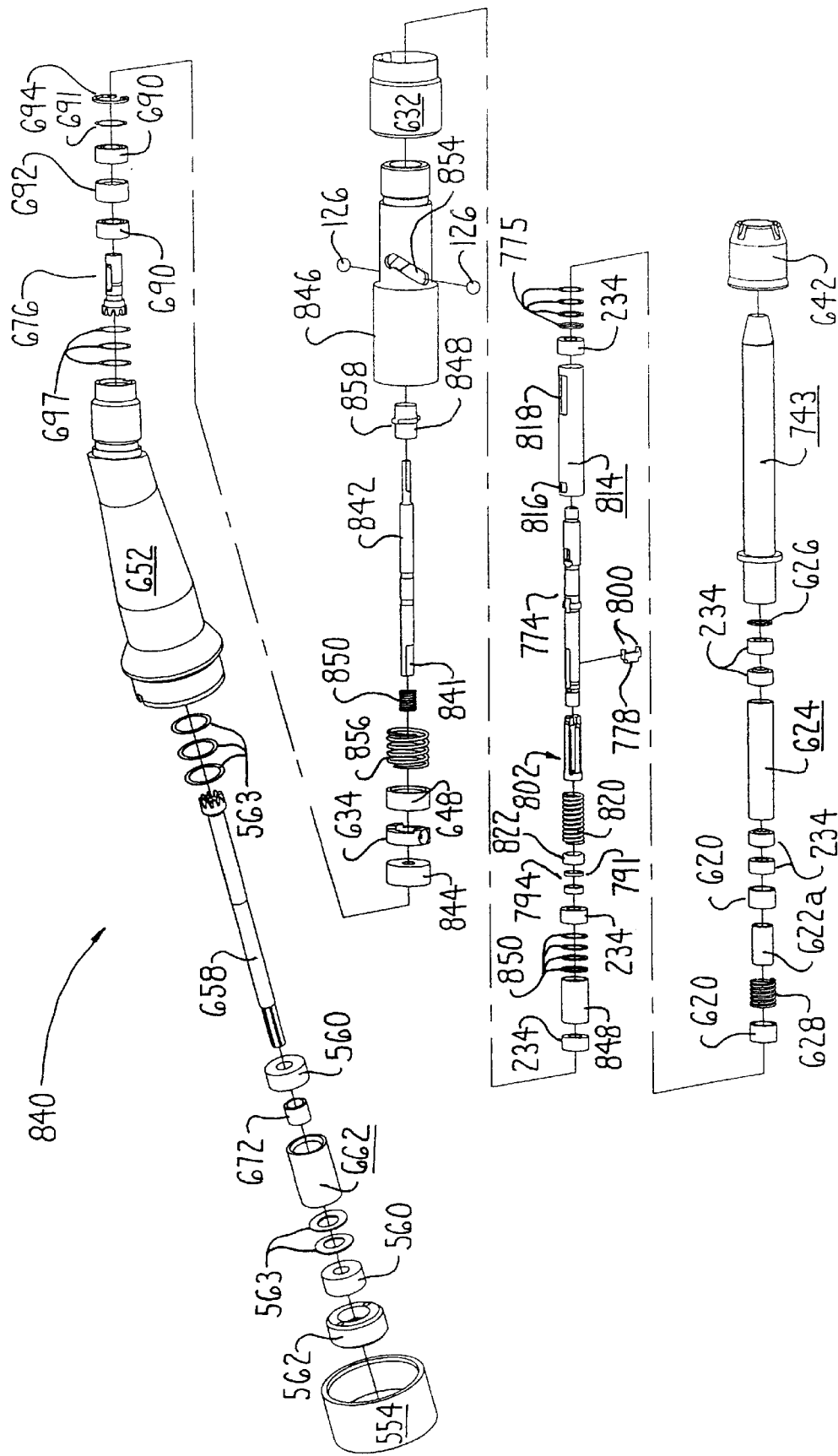
FIG. 63 is an exploded view of the attachment of FIG. 62.

FIGS. 63, 64 and 65 illustrate an angled long attachment 840 of this invention. Attachment 840 includes housing 652, input drive shaft 658, transfer gear 676 and the associated components used to hold the drive shaft and gear in position.

An elongated push rod 842 extends forward from transfer gear 676. The proximal end of push rod 842 is formed with flats 841. Consequently, when the proximal end of the push rod 842 is fitted in the transfer gear bore 688 the push rod both rotates in unison and is able to move longitudinally relative to the transfer gear 676.

A front housing 846, similar to front housing 657, extends forward from angle housing neck 656. Push rod 842 is substantially located in front housing 846. A bearing assembly 844 rotatably holds the proximal end of the push rod in front housing 846.

Nose tube 743 extends forward from the front end of front housing 657. The nose tube 743 surrounds the forward portion of push rod 842. A bearing assembly 234 provides a low friction interface between the push rod 842 and the adjacent inner surface of nose tube 743.

Previously described output drive shaft 774, collet 802 and collet sleeve 814 are rotatably mounted in nose tube 743. When attachment 840 is assembled flats located at the distal end of the push rod, flats not identified seat in bore 780 of the output drive shaft 774. Collectively, the drive shaft 774 and the push rod 842 are formed so that rotation of the push rod will cause like motion of the output drive shaft and the push rod is able to move relative to longitudinally fixed drive shaft.

A tube-shaped spacer 848 is also seated in the proximal end of nose tube 743. Spacer 848 serves to hold the bearing assembly 234 fitted to the push rod 842 and the bearing assembly fitted to the proximal end of the output drive shaft 774 apart from each other. Shims 850 are provided to accommodate for manufacturing tolerances.

It will further be observed that a small sleeve 854 is press fitted or otherwise securely fitted to push rod 842. Sleeve 848 is shape to define a small, rearwardly directed annular chamber 849 between an inner wall of the spring and the outer surface of the push rod 842. A compression spring 850 is seated in chamber 849. Spring 850 works against bearing assembly 844 to impose a small forward force on sleeve 848 and push rod 842.

Actuator 634 is disposed around the push rod 842 and is located rearwardly of sleeve 848. Collar 632 extends around a constant diameter section of front housing 846. Ball bearings 126, seated in front housing slots 854 couple the actuator 634 to the collar 632. Slots 854 are dimensioned so that the manual rotation of the collar 632 results in the forward displacement of the actuator 634.

A spring 856 is located around sleeve 848. The distal end of spring 856 is seated against an annular step formed inside front housing 846. The distal end of spring 848 works against spacer ring 648 that abuts the forward facing face of the actuator 634.

When attachment 840 is in the run state, spring 820 generates the force that serves to position the collet sleeve 814 of the collet ankles 812. Spring 856 prevents the unintended forward movement of the actuator 634.

Attachment 840 is placed in the accessory load state by the rotation of collar 632. The rotation of the collar 632 results in the forward movement of actuator 634. Eventually, actuator 634 abuts an outwardly extending lip 858 integral with sleeve 848. Thus, as the actuator 634 continues to move forward, it pushes sleeve 848 and, therefore push rod 842, in the same direction. The forward displacement of the push rod 842 results in the like translation of the collet sleeve 814 away from collet ankles 812. Once the collet sleeve 814 and collet ankles 812 are so positioned relative to each other, an accessory 40 can be removed replaced or reset as previously described.

In the described version of the system of this invention the overall length of attachment 740 may be 2.5 cm or more than the length of attachment 550. In still other versions of this invention, this difference in length may by 3.5 cm or more or even 4.5 cm or more. This difference in length is primarily because nose tubes 614 and 743 of attachments 550 and 740, respectively, are of different length. (Housings 552 and 742 are of similar length.)

However, owing to the placement and dimensioning of the components internal to the attachments 550 and 742, the levels at which the collet feet internal to the attachments grasp the complementary accessories 40 are substantially identical relative to the distal ends of the nose tubes 614 and 743. In some versions of the invention, this difference in distances relative to this most distal position along the attachments is 1.0 cm or less. In other versions of the invention, the difference in distances is 0.5 cm or less. In preferred version of the invention, this difference in distances is 0.25 cm or less. In still other preferred versions of the invention, the distance between the distal end of the attachments and the collet feet internal to these attachments is the same regardless in variations in length between attachments.

An advantage of this arrangement is that cutting accessories 40 having shafts of common length can each be used in each one of the attachments regardless of the difference in overall length between the attachments. Thus, this further minimizes the need to have a number of different cutting accessories available in which the only difference between the accessories is the length of their shafts.

It should also be understood that the arrangement of bearings in the nose tubes minimizes the likelihood that lateral stress imposed on the cutting accessories will result in either shafts biding against the nose tubes or "shaft whip" (the flexing back and forth of the shaft.

It should also be realized that the placement of the construction of this invention makes it possible to provide nose tubes that have a relatively narrow outer diameter. In some versions of the invention, this diameter is less than 0.313 inches. In other versions of the invention, this diameter is 0.260 inches or less. In other versions of the invention, this diameter is 0.240 inches or less. In even still other versions of the invention, this diameter is 0.180 inches or less. In versions of this invention in which the nose tube bearings are replaced by low friction bushings, it is anticipated that this diameter may be 0.13 inches or less. A benefit gained by this feature of the invention is that the minimization in nose tube diameter increases the surgeon's field of view.

Still another feature of this invention is that the rearward facing positioning of collet 578 in attachments 550 and 650 contribute to making it possible to using a single common collar 632 for each of attachments 550, 650, 740 and 840. In many preferred versions of the invention collar 632 has an outer diameter of 0.57 inches or less. In still more preferred versions of the invention, this dimension is 0.4 inches or less. An advantage of this construction of the invention is that, by holding the diameter of the collar as well as the components distal to this size, it further ensures that that the extent to which the attachment obstructs the surgeon's field of view is kept to a minimum.

Also, it should be realized that, in other versions of the invention, one or more of coupling assemblies 38, 176, 334, and 412 might not be built into a removable attachment. In these versions of the invention, the coupling assembly may be integrally built into the surgical handpiece designed to actuate the cutting accessories 40. The same is, of course true for attachments 550, 650, 740 and 840.

Furthermore, the shape of the various components of this invention may vary from what has been described. For example, this invention is not limited to collets that only have two feet. In some versions of the invention one or three more retractable members may serve as the locking element or elements that grip the cutting accessory. It should likewise be recognized that the components of the various versions of the invention may be substituted with each other as necessary. Members other than the described collets may be used as the holding members for releasably securing the cutting accessories to the attachments. These members include retractable tongues.

Similarly, the retention features 156 integral with the cutting accessory shaft 44 may have different profiles than described. For example, surfaces 160 and 162, instead of being straight, may be curved. The angle of surfaces 160 and 162, relative to faces 158 may be steep, for example, perpendicular, or shallow, greater than 135°. Also, the cross sectional profile of the faces forming the retention features may not always be square. Clearly the size and shape of faces 158 may change with the profile of the coupling assembly gripping surfaces intended to abut these faces. For the reasons set forth in U.S. Pat. No. 5,888,200, the retention features may be formed so that the edge corners where the retention features meet are differing distances from the longitudinal axis of the shaft stem 154. Also, there is no requirement that, in all versions of the invention, the faces of the retention features be recessed relative to the outer surface of the shaft stem 154. In some versions of the invention, the retention features 156 may consist of members that extend beyond the outer surface of the associated shaft stem 154.

Moreover, preload springs may be disposed within the head tubes of the attachments of this invention. As discussed in U.S. Pat. No. 5,888,200, this type of spring imposes forces on the bearing assemblies internal to the head tube so as to reduce bearing chatter.

Therefore, it is an object of the appended claims to cover all such modifications and variations as come within the true spirit and scope of this invention.

What is claimed is:

1. A cutting accessory for a use with a surgical tool, said cutting accessory including:

a head;

an elongated shaft that extends from said head, said shaft having a longitudinal axis;

a plurality of retention features formed in said shaft at longitudinally spaced apart locations along said shaft; and a laterally extending section formed in said shaft between each pair of adjacent, longitudinally spaced apart retention features, said shaft being formed so that said laterally extending section is shaped asymmetrically relative to the longitudinal axis of said shaft.

2. The cutting accessory of claim 1, wherein:

said shaft is formed to have: a main body located adjacent said head, said main body having a first cross sectional diameter; and a stem that extends from said main body that is spaced from said head and said stem has a second cross sectional diameter that is less than the first cross sectional diameter; and said retention features are formed in said stem of said shaft.

3. The cutting accessory of claim 2, wherein said stem is formed with a plurality of linearly aligned, longitudinally spaced apart faces that extend inwardly relative to an outer surface of said stem and said faces are said retention features.

4. The cutting accessory of claim 2, wherein said stem is formed with longitudinally spaced apart sets of inwardly directed faces, each said set of faces comprising a plurality of faces that are arranged circumferentially around said stem and each said set of faces forms one said retention feature.

5. The cutting accessory of claim 1, wherein:

first and second longitudinally spaced apart retention features are formed on a first arcuate section of said shaft;

third and fourth longitudinally spaced apart retention features are formed on a second arcuate section of said shaft wherein, the first and third retention features are laterally aligned with each other and the second and fourth retention features are laterally aligned with each other;

the first and second retention features define a crest that defines a first side of the laterally extending section, said crest being located a first distance from the longitudinal axis of said shaft; and a flat is located between the third and fourth retention features wherein the flat is a second side of the laterally extending section and said flat is located a second distance from the longitudinal axis of said shaft, the second distance being less than the first distance.

6. The cutting accessory of claim 1, wherein said shaft is formed with longitudinally spaced apart sets of inwardly directed faces, each said set of faces comprising a plurality of faces that are arranged circumferentially around said shaft and each said set of faces forms one said retention feature.

7. The cutting accessory of claim 6, wherein the faces forming each said set of faces are circumferentially spaced apart from each other.

8. The cutting accessory of claim 6, wherein said shaft is formed so that each said set of faces comprises two faces that are circumferentially spaced apart from each other.

9. The cutting accessory of claim 1, wherein said shaft is formed with a plurality of linearly aligned, longitudinally spaced apart faces that extend inwardly relative to an outer surface of said shaft and said faces are said retention features.

10. The cutting accessory of claim 1, wherein said shaft is formed with a plurality of linearly aligned, longitudinally spaced apart faces that extend inwardly relative to an outer surface of said shaft and that have curved profile and said faces are said retention features.

11. The cutting accessory of claim 1, wherein said shaft is formed with a plurality of linearly aligned, longitudinally spaced apart, curved profile faces and said faces are said retention features.

12. A cutting accessory for use with a surgical tool, said cutting accessory including:

a head;

an elongated shaft that extends from said head, said shaft having a longitudinal axis;

first, second, third and fourth retention features formed on said shaft, wherein the first and second retention features are longitudinally aligned with and longitudinally spaced apart from each other, the third and fourth retention features are longitudinally aligned and spaced apart from each other, the first retention feature is laterally aligned with and circumferentially displaced from the third retention feature and the second retention feature is laterally aligned with and circumferentially displaced from the fourth retention feature; and a first lateral section formed in said shaft at an interstitial location between the first and second retention features and the third and fourth retention features and said first lateral section is formed to have a first surface located between the first and second retention features that is located a first distance from the longitudinal axis of said shaft and a second surface located between the third and fourth retention features that is located a second distance from the longitudinal axis of said shaft, the second distance being less than the first distance.

13. The cutting accessory of claim 12, wherein said retention features are inwardly directed faces formed in said shaft.

14. The cutting accessory of claim 13, wherein said retention features are inwardly directed curved faces formed in said shaft.

15. The cutting accessory of claim 10, wherein the first and third retention features are circumferentially spaced apart from each other and the second and fourth retention features are circumferentially spaced apart from each other.

16. The cutting accessory of claim 10, wherein said first lateral section is shaped so that at least one of the first or second surfaces of said lateral section is a flat surface.

17. The cutting accessory of claim 12, wherein said first lateral section is shaped so that the first surface is a crest-shaped face located between the first and second retention features and said second surface is a flat face located between the third and fourth retention features.

18. The cutting accessory of claim 10, further including:

a fifth retention feature formed on said shaft, the fifth retention feature being longitudinally aligned with and longitudinally spaced apart from the second retention feature and a sixth retention feature formed on said shaft, the sixth retention feature being longitudinally aligned with and longitudinally spaced apart from the fourth retention feature and fifth retention feature is laterally aligned with the sixth retention feature; and a second lateral section formed on said shaft at an interstitial location between the second and fifth retention feature and the fourth and sixth retention feature, said second lateral section formed to have a first surface located between the second and fifth retention features that is located the second distance from the longitudinal axis of said shaft and a second surface located between the third and sixth retention features that is located the first distance from the longitudinal axis of said shaft.

19. The cutting accessory of claim 10, wherein, said shaft is shaped to have: a main section that extends from said head, said main section having a first diameter; and a stem section that extends from an end of said main section distal from said head, said stem section having a second diameter that is less than the first diameter and the retention features and said first lateral section are formed in said stem section.

20. The cutting accessory of claim 12, wherein said retention features are curved faces formed in said shaft.

21. A cutting accessory for use with a surgical tool, said cutting accessory including:

a head;

a shaft that extends from said head, said shaft having a longitudinal axis;

at least two sets of retention features formed on said shaft, each set of retention features comprising at least two longitudinally aligned, longitudinally spaced apart faces that are formed on said shaft wherein said sets of retention features are circumferentially offset from each other around said shaft and are aligned with each other so that each said face of a first said set of retention features is laterally aligned with a face of a second said set of retention features; and at least one lateral section formed on said shaft, said lateral section being located between the longitudinally spaced apart faces of said sets of retention features and said lateral section is formed to have a first surface located between the faces of the first said set of retention features and a second surface located between the faces of the second said set of retention features and said lateral section is formed so that the first and second surfaces provide said lateral section with an asymmetric cross sectional profile relative to the longitudinal axis of said shaft.

22. The cutting accessory of claim 21, wherein said sets of retention features are circumferentially spaced apart from each other.

23. The cutting accessory of claim 21, wherein said shaft has two said sets of retention features and said sets of retention features are diametrically arranged relative to the longitudinal axis of said shaft.

24. The cutting accessory of claim 21, wherein said lateral section is shaped so that at least one of the first or second surfaces is a flat surface.

25. The cutting accessory of claim 21, wherein said lateral section is shaped so that the first surface is a crest-shaped face and said second surface is a flat face.

26. The cutting accessory of claim 21, wherein:

each said set of retention features includes at least three said faces that are longitudinally aligned with and longitudinally spaced apart from each other; and said shaft includes at least two said lateral sections, wherein:

a first one of said lateral sections is located between adjacent first and second faces of said sets of retention features and is shaped so that the first surface of said first lateral section is located between the first and second faces of the first said set of retention features and the second surface of said first lateral section is located between the first and second faces of the second said set of retention features; and a second one of said lateral sections is located between adjacent second and third faces of said sets of retention features and is shaped so that second surface of said second lateral section is located between the second and third faces of the first said set of retention features and the first surface of said second lateral section is located between the second and third faces of the second said set of retention features.

27. The cutting accessory of claim 21, wherein said faces have a curved profile.

28. The cutting accessory of claim 21, wherein, said shaft is shaped to have: a main section that extends from said head, said main section having a first diameter; and a stem section that extends from an end of said main section distal from said head, said stem section having a second diameter that is less than the first diameter and the retention features and said lateral section are formed in said stem section.

29. The cutting accessory of claim 21, wherein said shaft is formed so that said faces forming said retention features are inwardly directed relative to an outer circumference of said shaft.

30. The cutting accessory of claim 21, wherein said shaft is formed so that said faces forming said retention features are inwardly directed relative to an outer circumference of said shaft and have curved profiles.

31. The cutting accessory of claim 19, wherein said shaft is formed so that said faces forming said retention features are curved faces.

* * * * *

UNITED STATES PATENT AND TRADEMARK OFFICE
CERTIFICATE OF CORRECTION

PATENT NO. : 6,562,055 B2  Page 1 of 1
DATED : May 13, 2003
INVENTOR(S) : James G. Walen It is certified that error appears in the above-identified patent and that said Letters Patent is hereby corrected as shown below:

<u>Column 42,</u>
Line 4, change "claim 10" to -- claim 12 --
Line 8, change "claim 10" to -- claim 12 --
Line 15, change "claim 10" to -- claim 12 --
Line 34, change "claim 10" to -- claim 12 --

<u>Column 44,</u>
Line 25, change "claim 19" to -- claim 21 --

Signed and Sealed this

Sixteenth Day of September, 2003

JAMES E. ROGAN
*Director of the United States Patent and Trademark Office*